(12) United States Patent
Davids et al.

(10) Patent No.: US 7,622,555 B2
(45) Date of Patent: Nov. 24, 2009

(54) CYTOKINE ANTAGONIST MOLECULES

(75) Inventors: Andrew Robert Davids, London (GB); Richard Joseph Fagan, London (GB); Christopher Benjamin Phelps, London (GB); Christine Power, Thoiry (FR); Yolande Chvatchko, Confignon (CH); Ursula Boschert, Troinex (CH)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 10/706,691

(22) Filed: Nov. 12, 2003

(65) Prior Publication Data

US 2004/0204352 A1  Oct. 14, 2004

Related U.S. Application Data

(63) Continuation-in-part of application No. PCT/GB03/01851, filed on Apr. 30, 2003.

(30) Foreign Application Priority Data

Apr. 30, 2002  (GB) ................................. 0209884.6

(51) Int. Cl.
| | |
|---|---|
| C07K 17/00 | (2006.01) |
| A61K 38/16 | (2006.01) |
| C07K 14/00 | (2006.01) |
| C07K 16/00 | (2006.01) |
| C12P 21/08 | (2006.01) |

(52) U.S. Cl. ..................... 530/351; 530/380; 530/350; 530/387.1; 530/387.9; 530/388.23

(58) Field of Classification Search ........................ None
See application file for complete search history.

(56) References Cited

U.S. PATENT DOCUMENTS 6,420,526 B1 * 7/2002 Ruben et al. ................ 530/350
6,783,961 B1 * 8/2004 Edwards et al. ............ 435/91.1

FOREIGN PATENT DOCUMENTS

| EP | 1 033 401 A3 | 4/2004 |
|---|---|---|
| WO | WO 01 54477 A | 8/2001 |
| WO | WO 02 34783 A | 5/2002 |
| WO | WO 02 40671 A | 5/2002 |
| WO | WO 0240671 A2 * | 5/2002 |
| WO | 2004/007672 | 1/2004 |
| WO | 2004/080148 | 9/2004 |

OTHER PUBLICATIONS

Marks, et al Atherosclerosis 168:1-14, 2003 'A review on the diagnosis, natural history, and treatment of familial hypercholesterolaemia'.*
Ju, et al Proc. Natl. Acad. Sci. 88:2658-2662, 1991 'Conversion of the interleukin 1 receptor antagonist into an agonist by site-specific mutagenesis'.*
Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 491-495.*
Vilcek 2003. in Chapter 1, The Cytokine Handbood, 4th edition.*
Nordmann et al. 2002. Clinica Chimica Acta 325:17-37.*
Batey et al 2002. Frontiers in Bioscience 7:1662-1675.*
Edwards J.B.D.M: "Sequence Tag and encoded human protein" retrieved from HTTP://www.EBI.AC.UK, Database accession No. BD511416 XP002259339.
Tang, et al.: Isolated polypeptides for treatment of diseases, diagnostics, raising antibodies and research use. XP 002259341.
Sugano, et al., "NEDO human cDNA Sequencing project" Database accession No. AK098396; XP 002259340.
International Search report for Ares Trading S.A. dated May 12, 2003; PCT/GB03/01851 filed Apr. 30, 2003.

* cited by examiner

*Primary Examiner*—Manjunath N Rao
*Assistant Examiner*—Shulamith H Shafer
(74) *Attorney, Agent, or Firm*—Frommer Lawrence & Haug LLP; Thomas J. Kowalski; Ljiljana Minwalla

(57) ABSTRACT

This invention relates to a novel protein (INSP052), herein identified as an immunoglobulin domain-containing cell surface recognition molecule and to the use of this proteins and nucleic acid sequences from the encoding gene in the diagnosis, prevention and treatment of disease. The invention also relates to the identification of the extracellular domain of INSP052.

18 Claims, 22 Drawing Sheets

FIG. 1

BLASTP 2.2.1 [Jul-12-2001]

Reference: Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.

Query= genscan2
    (416 letters)

Database: ncbi-nr
    897,014 sequences; 280,886,335 total letters

Searching....................................................done

- - - - - - - - - - - - - - - - - - - - - - - - - - - - - - - - -

| Sequences producing significant alignments: | Score (bits) | E Value |
|---|---|---|
| pir‖JC1512 biliary glycoprotein H - mouse | 81 | 2e-14 |
| pir‖JC1506 biliary glycoprotein B - mouse | 81 | 2e-14 |
| pir‖A39037 carcinoembryonic antigen mmCGM2 precursor - mouse >g... | 79 | 9e-14 |
| ref|NP_036056.1| (NM_011926) CEA-related cell adhesion molecule ... | 79 | 9e-14 |
| pir‖JC1509 biliary glycoprotein E - mouse | 73 | 5e-12 |
| ref|NP_001758.1| (NM_001767) CD2 antigen (p50), sheep red blood ... | 73 | 6e-12 |
| ref|NP_113943.1| (NM_031755) carcinoembryonic antigen-related ce... | 72 | 8e-12 |
| pir‖RWHUC2 T-cell surface glycoprotein CD2 precursor - human >g... | 72 | 8e-12 |
| gb|AAA51946.1| (M16336) CD2 surface antigen [Homo sapiens] | 72 | 8e-12 |
| ref|NP_291021.1| (NM_033543) hypothetical protein R29124_1 [Homo... | 72 | 1e-11 |
| pir‖JC1507 biliary glycoprotein C - mouse | 71 | 2e-11 |
| emb|CAA47697.1| (X67280) biliary glycoprotein [Mus musculus] | 71 | 2e-11 |
| pir‖S34338 biliary glycoprotein F - mouse >gi|312586|emb|CAA476... | 71 | 2e-11 |
| pir‖JC1511 biliary glycoprotein G - mouse | 71 | 2e-11 |

>pir||JC1512 biliary glycoprotein H - mouse

Length = 341

Score = 80.9 bits (198), Expect = 2e-14

Identities = 54/168 (32%), Positives = 86/168 (51%), Gaps = 9/168 (5%)

```
Query:  73  RDKPVTVVQSIGTEVIGTLR----PDYRDRIRLFENGSLLLSDLQLADEGTYEVEISITD  128
             + PV+   I +V GT +    P + R ++ NGSLL+ + + D G Y +E+  TD
Sbjct:  69  KGNPVSTNAEIVHQVTGTNKTTTGPAHSGRETVYSNGSLLIQRVTVKDTGVYTIEM--TD  126

Query: 129  DTFTG-EKTINLTVDVPISRPQVLVASTTVLELSEAFTLNCSHENGTKPSYTWLKDGKPL  187
             + F   E T+   V P+++P + V +TTV EL ++ TL C  N    + WL + + L
Sbjct: 127  ENFRRTEATVQFHVHQPVTQPSLQVTNTTVKEL-DSVTLTCL-SNDIGANIQWLFNSQSL  184

Query: 188  LNDSRMLLSPDQKVLTITRVLMEDDDLYSCMVENPISQGRSLPVKITV  235
                 RM LS +  +L I +  ED   Y C + NP+S  RS +K+ +
Sbjct: 185  QLTERMTLSQNNSILRIDPIKREDAGEYQCEISNPVSVKRSNSIKLDI  232
```

FIG. 3

| Sequences producing significant alignments: | Score (bits) | E Value |
|---|---|---|
| gi\|483306\|pir\|\|JC1506  biliary glycoprotein B - mouse | 79 | 1e-13 |
| gi\|111207\|pir\|\|A39037  carcinoembryonic antigen mmCGM2 precu... | 77 | 3e-13 |
| gi\|483312\|pir\|\|JC1512  biliary glycoprotein H - mouse | 77 | 4e-13 |
| gi\|13937381\|ref\|NP_036056.1\|  (NM_011926) CEA-related cell a... | 75 | 1e-12 |
| gi\|228710\|prf\|\|1809184A  pregnancy-specific glycoprotein [Ra... | 70 | 5e-11 |
| gi\|483307\|pir\|\|JC1507  biliary glycoprotein C - mouse | 70 | 6e-11 |
| gi\|16117775\|ref\|NP_291021.1\|  (NM_033543) hypothetical prote... | 69 | 8e-11 |
| gi\|483309\|pir\|\|JC1509  biliary glycoprotein E - mouse | 69 | 9e-11 |
| gi\|312582\|emb\|CAA47695.1\|  (X67278) biliary glycoprotein [Mu... | 69 | 1e-10 |
| gi\|483311\|pir\|\|JC1511  biliary glycoprotein G - mouse | 68 | 2e-10 |

FIG. 4

>gi|483306|pir||JC1506 biliary glycoprotein B - mouse

Length = 278

Score = 78.6 bits (192), Expect = 1e-13

Identities = 54/168 (32%), Positives = 86/168 (51%), Gaps = 9/168 (5%)

Query: 73  RDKPVTVVQSIGTEVIGTLR----PDYRDRIRLFENGSLLLSDLQLADEGTYEVEISITD 128
             + PV+    I +V GT +    P + R ++ NGSLL+ + + D G Y +E +TD
Sbjct: 69  KGNPVSTNAEIVHQVTGTNKTTTGPAHSGRETVYSNGSLLIQRVTVKDTGVYTIE--MTD 126

Query: 129 DTF-TGEKTINLTVDVPISRPQVLVASTTVLELSEAFTLNCSHENGTKPSYTWLKDGKPL 187
             + F  E T+   V  P+++P + V +TTV EL ++ TL C  N    + WL + + L
Sbjct: 127 ENFRRTEATVQFHVHQPVTQPSLQVTNTTVKEL-DSVTLTCL-SNDIGANIQWLFNSQSL 184

Query: 188 LNDSRMLLSPDQKVLTITRVLMEDDDLYSCVVENPISQVRSLPVKITV 235
             RM LS + +L I +  ED   Y C + NP+S  RS +K+ +
Sbjct: 185 QLTERMTLSQNNSILRIDPIKREDAGEYQCEISNPVSVKRSNSIKLDI 232

FIG. 5

```
  1 ATGAAGAGAG AAAGGGGAGC CCTGTCCAGA GCCTCCAGGG CCCTGCGCCT TGCTCCTTTT
    m  k  r  e  r  g  a  l  s  r  a  s  r  a  l  r  l  a  p  f

61 GTCTACCTTC TTCTGATCCA GACAGACCCC CTGGAGGGGG TGAACATCAC CAGCCCCGTG
    v  y  l  l  l  i  q  t  d  p  l  e  g  v  n  i  t  s  p  v

121 CGCCTGATCC ATGGCACCGT GGGGAAGTCG GCTCTGCTTT CTGTGCAGTA CAGCAGTACC
    r  l  i  h  g  t  v  g  k  s  a  l  l  s  v  q  y  s  s  t

181 AGCAGCGACA GGCCTGTAGT GAAGTGGCAG CTGAAGCGGG ACAAGCCAGT GACCGTGGTG
    s  s  d  r  p  v  v  k  w  q  l  k  r  d  k  p  v  t  v  v

241 CAGTCCATTG GCACAGAGGT CATCGGCACC CTGCGGCCTG ACTATCGAGA CCGTATCCGA
    q  s  i  g  t  e  v  i  g  t  l  r  p  d  y  r  d  r  i  r

301 CTCTTTGAAA ATGGCTCCCT GCTTCTCAGC GACCTGCAGC TGGCCGATGA GGGCACCTAT
    l  f  e  n  g  s  l  l  l  s  d  l  q  l  a  d  e  g  t  y

361 GAGGTCGAGA TCTCCATCAC CGACGACACC TTCACTGGGG AGAAGACCAT CAACCTTACT
    e  v  e  i  s  i  t  d  d  t  f  t  g  e  k  t  i  n  l  t

421 GTAGATGTGC CCATTTCGAG GCCACAGGTG TTGGTGGCTT CAACCACTGT GCTGGAGCTC
    v  d  v  p  i  s  r  p  q  v  l  v  a  s  t  t  v  l  e  l

481 AGCGAGGCCT TCACCTTGAA CTGCTCACAT GAGAATGGCA CCAAGCCCAG CTACACCTGG
    s  e  a  f  t  l  n  c  s  h  e  n  g  t  k  p  s  y  t  w

541 CTGAAGGATG GCAAGCCCCT CCTCAATGAC TCGAGAATGC TCCTGTCCCC CGACCAAAAG
    l  k  d  g  k  p  l  l  n  d  s  r  m  l  l  s  p  d  q  k

601 GTGCTCACCA TCACCCGCGT GCTCATGGAG GATGACGACC TGTACAGCTG CATGGTGGAG
    v  l  t  i  t  r  v  l  m  e  d  d  d  l  y  s  c  m  v  e

661 AACCCCATCA GCCAGGGCCG CAGCCTGCCT GTCAAGATCA CCGTATACAG AAGAAGCTCC
    n  p  i  s  q  g  r  s  l  p  v  k  i  t  v  y  r  r  s  s

721 CTTTACATCA TCTTGTCTAC AGGAGGCATC TTCCTCCTTG TGACCTTGGT GACAGTCTGT
    l  y  i  i  l  s  t  g  g  i  f  l  l  v  t  l  v  t  v  c

781 GCCTGCTGGA AACCCTCCAA AAGGAAACAG AAGAAGCTAG AAAAGCAAAA CTCCCTGGAA
    a  c  w  k  p  s  k  r  k  q  k  k  l  e  k  q  n  s  l  e
```

```
 841  TACATGGATC AGAATGATGA CCGCCTGAAA CCAGAAGCAG ACACCCTCCC TCGAAGTGGT
       y  m  d    q  n  d    d  r  l    k  p  e    a  d  t    l  p  r  s  g

901  GAGCAGGAAC GGAAGAACCC CATGGCACTC TATATCCTGA AGGACAAGGA CTCCCCGGAG
       e  q  e    r  k  n    p  m  a    l  y  i    l  k  d    k  d  s  p  e

961  ACCGAGGAGA ACCCGGCCCC GGAGCCTCGA AGCGCGACGG AGCCCGGCCC GCCCGGCTAC
       t  e  e    n  p  a    p  e  p    r  s  a    t  e  p    g  p  p  g  y

1021  TCCGTGTCTC CCGCCGTGCC CGGCCGCTCG CCGGGGCTGC CCATCCGCTC TGCCCGCCGC
       s  v  s    p  a  v    p  g  r    s  p  g    l  p  i    r  s  a  r  r

1081  TACCCGCGCT CCCCAGCGCG CTCCCCAGCC ACCGGCCGGA CACACTCGTC GCCGCCCAGG
       y  p  r    s  p  a    r  s  p    a  t  g    r  t  h    s  s  p  p  r

1141  GCCCCGAGCT CGCCCGGCCG CTCGCGCAGC GCCTCGCGCA CACTGCGGAC TGCGGGCGTG
       a  p  s    s  p  g    r  s  r    s  a  s    r  t  l    r  t  a  g  v

1201  CACATAATCC GCGAGCAAGA CGAGGCCGGC CCGGTGGAGA TCAGCGCCTG AGCCGCCTCG
       h  i  i    r  e  q    d  e  a    g  p  v    e  i  s    a

1261  GGATCCCCTG AGAGGCGCCC GCGGTCTGCG GCCAGTGGCC CGGGGGAAAG CTGGGGCTGG
1321  GAAGCCCGGG CGCGGCGCGC TGGGGACGAG GGGAGGTCCC GGGGGGGCGC TGGTGTCTCG
1381  GGTGTGAACG TGTATGAGCA TGCGCAGACG GAGGCGGGTG CGCGGAGGCG GCAGTGTTGA
1441  TATGGTGAAA CCGGGTCGCA TTTGCTTCCG GTTTACTGGC TGTGTCCTCA CTTGGTATAG
1501  GTTGTGCCCT CTTAGGACCA CATAGATTAT TACATTTCTG GCCCAATACC CAAAAGGGTT
1561  TTATGGAAAC TAACATCAGT AACCTAACCC CCGTGACTAT CCTGTGCTCT TCCTAGGGAG
1621  CTGTGTTGTT TCCCACCCAC CACCCTTCCC TCTGAACAAA TGCCTGAGTG CTGGGGCACT
1681  TTTTTTTTTT TTTTTTTTTT TTTTTTTTTT GCAAGTTCAG ATTAGAGAGG CCACTTTCCC
1741  AGAATCCACA GCTGCACTAA GCTAAGGAGA AGCCAGATGC CGGTTACTGG GTGTGCAGGG
1801  GCTGTTCTGA GCTGGGGGGA TCATTGTGAA GGCCTTCTTC CCTGGGCACC TGGTACCTGG
1861  GGACCTACAA GGTGGTGAGG GAAGGGTACG AGTACATTCC TTTTCCCTCT GACCTGGGCG
1921  CTAGCAAGGG CAAAGAACCC GAGCCTGCCA GCTTGGCCTC CTCCCACAGC CTCCCTCGGA
1981  GGCATGCCAT GCCAAGCACT CTTTCTGTCT CTGTTCATGA ATAAA
```

```
gi 115886 ATGAAGAGAGAAAGGGGAGCCCTGTCCAGAGCCTCCAGGGCCCTGCGCCT 115935
          ||||||||||||||||||||||||||||||||||||||||||||||||||
        1 ATGAAGAGAGAAAGGGGAGCCCTGTCCAGAGCCTCCAGGGCCCTGCGCCT       50
          ─────────────────────────▶
             INSP052-BIP-exon1F
                               ─────────────────▶
                                  INSP052-exon2F gi 115936 TGCTCCTTTTGTCTACCTTCTTCTGATCCAGACAGgtagg.......cac 115970
          |||||||||||||||||||||||||||||||||||>>>>> 10852 >>>
       51 TGCTCCTTTTGTCTACCTTCTTCTGATCCAGACAG...............       85
                                    ◀──────────────────
                                       INSP052-exon1R cont
    INSP052-exon2F cont
    ─────────────────▶
gi 115970 agACCCCCTGGAGGGGGTGAACATCACCAGCCCCGTGCGCCTGATCCATG 126870
          >>||||||||||||||||||||||||||||||||||||||||||||||||
       85 ..ACCCCCTGGAGGGGGTGAACATCACCAGCCCCGTGCGCCTGATCCATG      133
                   ◀────────────────
                     INSP052-exon1R gi 126871 GCACCGTGGGGAAGTCGGCTCTGCTTTCTGTGCAGTACAGCAGTACCAGC 126920
          ||||||||||||||||||||||||||||||||||||||||||||||||||
      134 GCACCGTGGGGAAGTCGGCTCTGCTTTCTGTGCAGTACAGCAGTACCAGC      183 gi 126921 AGCGACAGGCCTGTAGTGAAGTGGCAGCTGAAGCGGGACAAGCCAGTGAC 126970
          ||||||||||||||||||||||||||||||||||||||||||||||||||
      184 AGCGACAGGCCTGTAGTGAAGTGGCAGCTGAAGCGGGACAAGCCAGTGAC      233 gi 126971 CGTGGTGCAGTCCATTGGCACAGAGGTCATCGGCACCCTGCGGCCTGACT 127020
          ||||||||||||||||||||||||||||||||||||||||||||||||||
      234 CGTGGTGCAGTCCATTGGCACAGAGGTCATCGGCACCCTGCGGCCTGACT      283 gi 127021 ATCGAGACCGTATCCGACTCTTTGAAAATGGCTCCCTGCTTCTCAGCGAC 127070
          ||||||||||||||||||||||||||||||||||||||||||||||||||
      284 ATCGAGACCGTATCCGACTCTTTGAAAATGGCTCCCTGCTTCTCAGCGAC      333 gi 127071 CTGCAGCTGGCCGATGAGGGCACCTATGAGGTCGAGATCTCCATCACCGA 127120
          ||||||||||||||||||||||||||||||||||||||||||||||||||
      334 CTGCAGCTGGCCGATGAGGGCACCTATGAGGTCGAGATCTCCATCACCGA      383
```

FIG. 6(contd.)

```
                                        INSP052-exon3F
                                       ─────────────▶
gi 127121  CGACACCTTCACTGGGGAGAAGACCATCAACCTTACTGTAGATGgtaaa.  127164
           ||||||||||||||||||||||||||||||||||||||||||||>>>>>
      384  CGACACCTTCACTGGGGAGAAGACCATCAACCTTACTGTAGATG......      427
                                       ◀─────────
                                       INSP052-exon2R cont
             INSP052-exon3F cont
           ─────────────▶
gi 127164  ....ctcagTGCCCATTTCGAGGCCACAGGTGTTGGTGGCTTCAACCACT    127922
           717 >>>>>|||||||||||||||||||||||||||||||||||||||||
      427  .........TGCCCATTTCGAGGCCACAGGTGTTGGTGGCTTCAACCACT      468
                    ◀─────────
                    INSP052-exon2R gi 127923  GTGCTGGAGCTCAGCGAGGCCTTCACCTTGAACTGCTCACATGAGAATGG    127972
           ||||||||||||||||||||||||||||||||||||||||||||||||||
      469  GTGCTGGAGCTCAGCGAGGCCTTCACCTTGAACTGCTCACATGAGAATGG      518 gi 127973  CACCAAGCCCAGCTACACCTGGCTGAAGGATGGCAAGCCCCTCCTCAATG    128022
           ||||||||||||||||||||||||||||||||||||||||||||||||||
      519  CACCAAGCCCAGCTACACCTGGCTGAAGGATGGCAAGCCCCTCCTCAATG      568 gi 128023  ACTCGAGAATGCTCCTGTCCCCCGACCAAAAGGTGCTCACCATCACCCGC    128072
           ||||||||||||||||||||||||||||||||||||||||||||||||||
      569  ACTCGAGAATGCTCCTGTCCCCCGACCAAAAGGTGCTCACCATCACCCGC      618 gi 128073  GTGCTCATGGAGGATGACGACCTGTACAGCTGCATGGTGGAGAACCCCAT    128122
           ||||||||||||||||||||||||||||||||||||||||||||||||||
      619  GTGCTCATGGAGGATGACGACCTGTACAGCTGCATGGTGGAGAACCCCAT      668 gi 128123  CAGCCAGGGCCGCAGCCTGCCTGTCAAGATCACCGTATACAgtgag....    128163
           ||||||||||||||||||||||||||||||||||||||||||>>>>> 295
      669  CAGCCAGGGCCGCAGCCTGCCTGTCAAGATCACCGTATACA.........      709
                                           ◀─────────
                                           INSP052-exon3R cont gi 128163  .cctagGAAGAAGCTCCCTTTACATCATCTTGTCTACAGGAGGCATCTTC    128502
                >>>>>|||||||||||||||||||||||||||||||||||||||||
      709  ......GAAGAAGCTCCCTTTACATCATCTTGTCTACAGGAGGCATCTTC      753
                  ◀─────────
                  INSP052-exon3R gi 128503  CTCCTTGTGACCTTGGTGACAGTCTGTGCCTGCTGGAAACCCTCCAAAAG    128552
           ||||||||||||||||||||||||||||||||||||||||||||||||||
      754  CTCCTTGTGACCTTGGTGACAGTCTGTGCCTGCTGGAAACCCTCCAAAAG      803
```

FIG. 6(contd.)

```
gi 128552 gtctg.....cacagGAAACAGAAGAAGCTAGAAAAGCAAAACTCCCTGG 129108
          >>>>> 521 >>>>>||||||||||||||||||||||||||||||||||
      803 ...............GAAACAGAAGAAGCTAGAAAAGCAAAACTCCCTGG     838 gi 129109 AATACATGGATCAGAATGATGACCGCCTGAAACCAGAAGgtgag.....t 129147
          |||||||||||||||||||||||||||||||||||||||>>>>> 286 >
      839 AATACATGGATCAGAATGATGACCGCCTGAAACCAGAAG...........  877 gi 129147 gcagCAGACACCCTCCCTCGAAGTGGTGAGCAGGAACGGAAGAACCCCAT 129479
          >>>>|||||||||||||||||||||||||||||||||||||||||||||
      877 ....CAGACACCCTCCCTCGAAGTGGTGAGCAGGAACGGAAGAACCCCAT  923 gi 129480 GGCACTCTATATCCTGAAGGACAAGgtgag.....tgcagGACTCCCCGG 130461
          |||||||||||||||||||||||||>>>>> 947 >>>>>|||||||||
      924 GGCACTCTATATCCTGAAGGACAAG...............GACTCCCCGG  958 gi 130462 AGACCGAGGAGAACCCGGCCCCGGAGCCTCGAAGCGCGACGGAGCCCGGC 130511
          ||||||||||||||||||||||||||||||||||||||||||||||||||
      959 AGACCGAGGAGAACCCGGCCCCGGAGCCTCGAAGCGCGACGGAGCCCGGC 1008 gi 130512 CCGCCCGGCTACTCCGTGTCTCCCGCCGTGCCCGGCCGCTCGCCGGGGCT 130561
          ||||||||||||||||||||||||||||||||||||||||||||||||||
     1009 CCGCCCGGCTACTCCGTGTCTCCCGCCGTGCCCGGCCGCTCGCCGGGGCT 1058 gi 130562 GCCCATCCGCTCTGCCCGCCGCTACCCGCGCTCCCCAGCGCGCTCCCCAG 130611
          ||||||||||||||||||||||||||||||||||||||||||||||||||
     1059 GCCCATCCGCTCTGCCCGCCGCTACCCGCGCTCCCCAGCGCGCTCCCCAG 1108 gi 130612 CCACCGGCCGGACACACTCGTCGCCGCCCAGGGCCCCGAGCTCGCCCGGC 130661
          ||||||||||||||||||||||||||||||||||||||||||||||||||
     1109 CCACCGGCCGGACACACTCGTCGCCGCCCAGGGCCCCGAGCTCGCCCGGC 1158 gi 130662 CGCTCGCGCAGCGCCTCGCGCACACTGCGGACTGCGGGCGTGCACATAAT 130711
          ||||||||||||||||||||||||||||||||||||||||||||||||||
     1159 CGCTCGCGCAGCGCCTCGCGCACACTGCGGACTGCGGGCGTGCACATAAT 1208 gi 130712 CCGCGAGCAAGACGAGGCCGGCCCGGTGGAGATCAGCGCCTGA 130754
          |||||||||||||||||||||||||||||||||||||||||||
     1209 CCGCGAGCAAGACGAGGCCGGCCCGGTGGAGATCAGCGCCTGA    1251
```

FIG. 7

```
  1  ACAAGTTTGT ACAAAAAAGC AGGCTTCGCC ACCATGAAGA GAGAAAGGGG AGCCCTGTCC
                                             m  k  r  e  r  g  a  l  s

61  AGAGCCTCCA GGGCCCTGCG CCTTGCTCCT TTTGTCTACC TTCTTCTGAT CCAGACAGAC
      r  a  s  r  a  l  r  l  a  p  f  v  y  l  l  l  i  q  t  d

121  CCCCTGGAGG GGGTGAACAT CACCAGCCCC GTGCGCCTGA TCCATGGCAC CGTGGGGAAG
      p  l  e  g  v  n  i  t  s  p  v  r  l  i  h  g  t  v  g  k

181  TCGGCTCTGC TTTCTGTGCA GTACAGCAGT ACCAGCAGCG ACAGGCCTGT AGTGAAGTGG
      s  a  l  l  s  v  q  y  s  s  t  s  s  d  r  p  v  v  k  w

241  CAGCTGAAGC GGGACAAGCC AGTGACCGTG GTGCAGTCCA TTGGCACAGA GGTCATCGGC
      q  l  k  r  d  k  p  v  t  v  v  q  s  i  g  t  e  v  i  g

301  ACCCTGCGGC CTGACTATCG AGACCGTATC CGACTCTTTG AAAATGGCTC CCTGCTTCTC
      t  l  r  p  d  y  r  d  r  i  r  l  f  e  n  g  s  l  l  l

361  AGCGACCTGC AGCTGGCCGA TGAGGGCACC TATGAGGTCG AGATCTCCAT CACCGACGAC
      s  d  l  q  l  a  d  e  g  t  y  e  v  e  i  s  i  t  d  d

421  ACCTTCACTG GGGAGAAGAC CATCAACCTT ACTGTAGATG TGCCCATTTC GAGGCCACAG
      t  f  t  g  e  k  t  i  n  l  t  v  d  v  p  i  s  r  p  q

481  GTGTTGGTGG CTTCAACCAC TGTGCTGGAG CTCAGCGAGG CCTTCACCTT GAACTGCTCA
      v  l  v  a  s  t  t  v  l  e  l  s  e  a  f  t  l  n  c  s

541  CATGAGAATG GCACCAAGCC CAGCTACACC TGGCTGAAGG ATGGCAAGCC CCTCCTCAAT
      h  e  n  g  t  k  p  s  y  t  w  l  k  d  g  k  p  l  l  n

601  GACTCGAGAA TGCTCCTGTC CCCCGACCAA AAGGTGCTCA CCATCACCCG CGTGCTCATG
      d  s  r  m  l  l  s  p  d  q  k  v  l  t  i  t  r  v  l  m

661  GAGGATGACG ACCTGTACAG CTGCATGGTG GAGAACCCCA TCAGCCAGGG CCGCAGCCTG
      e  d  d  d  l  y  s  c  m  v  e  n  p  i  s  q  g  r  s  l

721  CCTGTCAAGA TCACCGTATA CAGAAGAAGC TCCCACCATC ACCATCACCA TTGAAACCCA
      p  v  k  i  t  v  y  r  r  s  s  h  h  h  h  h  h  -

781  GCTTTCTTGT ACAAAGTGGT
```

FIG. 8

Molecule: pENTR-INSP052- EC-6HIS, 3005 bps DNA Circular
File Name: pENTR-INSP052-6HIS.cm5, dated 21 Feb 2003

Description: Ligation of Cons-6His.SEQ into pENTR-attL1-attL2

Molecule Features:

| Type | Start | End | Name | Description |
|---|---|---|---|---|
| MARKER | 21 | | | pENTR-F1 primer |
| MARKER | 110 | C | attL1 | |
| GENE | 136 | 873 | INSP052-EC-6HIS | |
| MARKER | 888 | | attL2 | |
| MARKER | 1001 | C | | pENTR-R1 primer |
| GENE | 1100 | 1909 | KanR | |
| REGION | 2030 | 2669 | ori | |

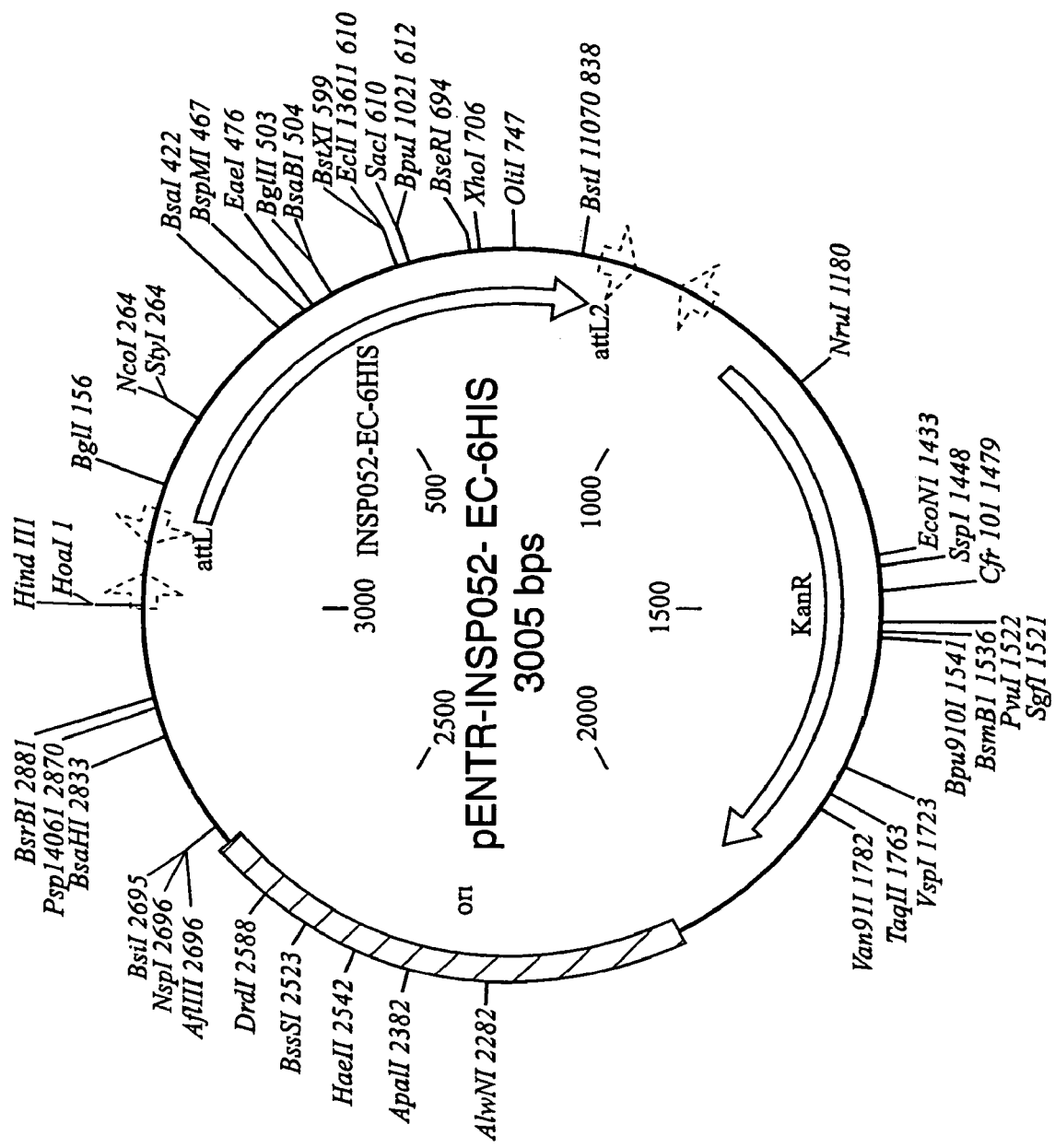
FIG. 8(contd.)

FIG. 9

Molecule:      pEAK12d-INSP052-EC-6HIS,  7687 bps DNA Circular
File Name:     pEAK12d-INSP052-6HIS.cm5,  dated 21 Feb 2003

Description:   Ligation of Cons-6His.SEQ into pEAK12d-attB1-attB2

Molecule Features:

| Type   | Start | End    | Name   | Description         |
|--------|-------|--------|--------|---------------------|
| REGION | 2     | 595    |        | pmb-ori             |
| GENE   | 596   | 1519   | AmpR   |                     |
| REGION | 1690  | 2795   | EF-1a  |                     |
| MARKER | 2703  |        |        | pEAK12F primer      |
| REGION | 2855  | 2887   | attB1  |                     |
| GENE   | 2888  | 3625   |        | INSP052-EC-6HIS (aa1-240) |
| REGION | 3629  | 3654   | attB2  |                     |
| MARKER | 3656  | C      |        | pEAK12R primer      |
| REGION | 3661  | 4089   |        | poly A/splice       |
| GENE   | 4708  | 4090 C |        | PUROMYCIN resistance |
| REGION | 4932  | 4709 C | tK     | tK promoter         |
| REGION | 5427  | 4933 C | Ori P  |                     |
| GENE   | 7479  | 5427 C | EBNA-1 |                     |
| REGION | 7480  | 7679   | sv40   |                     |

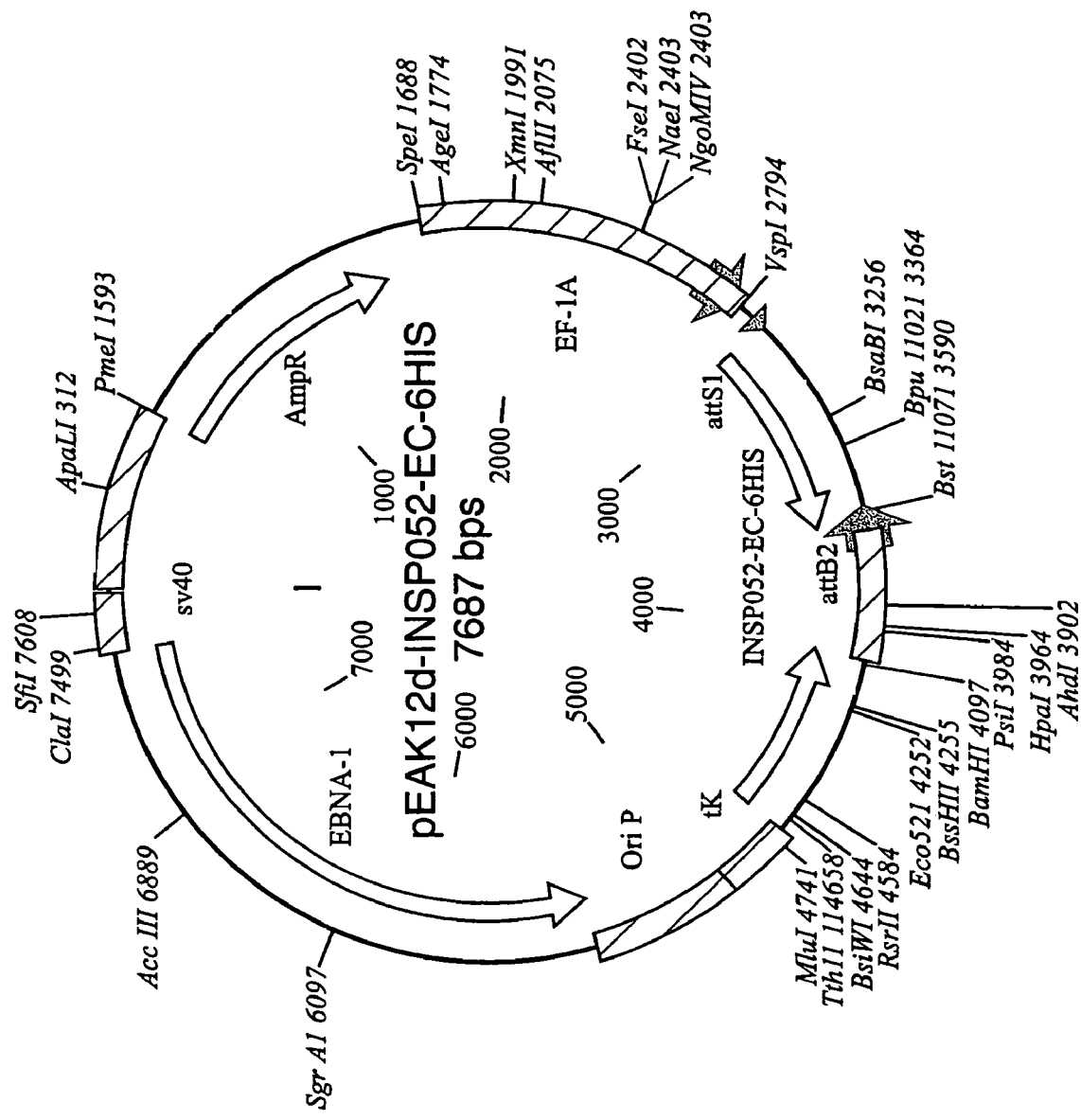
FIG. 9(contd.)

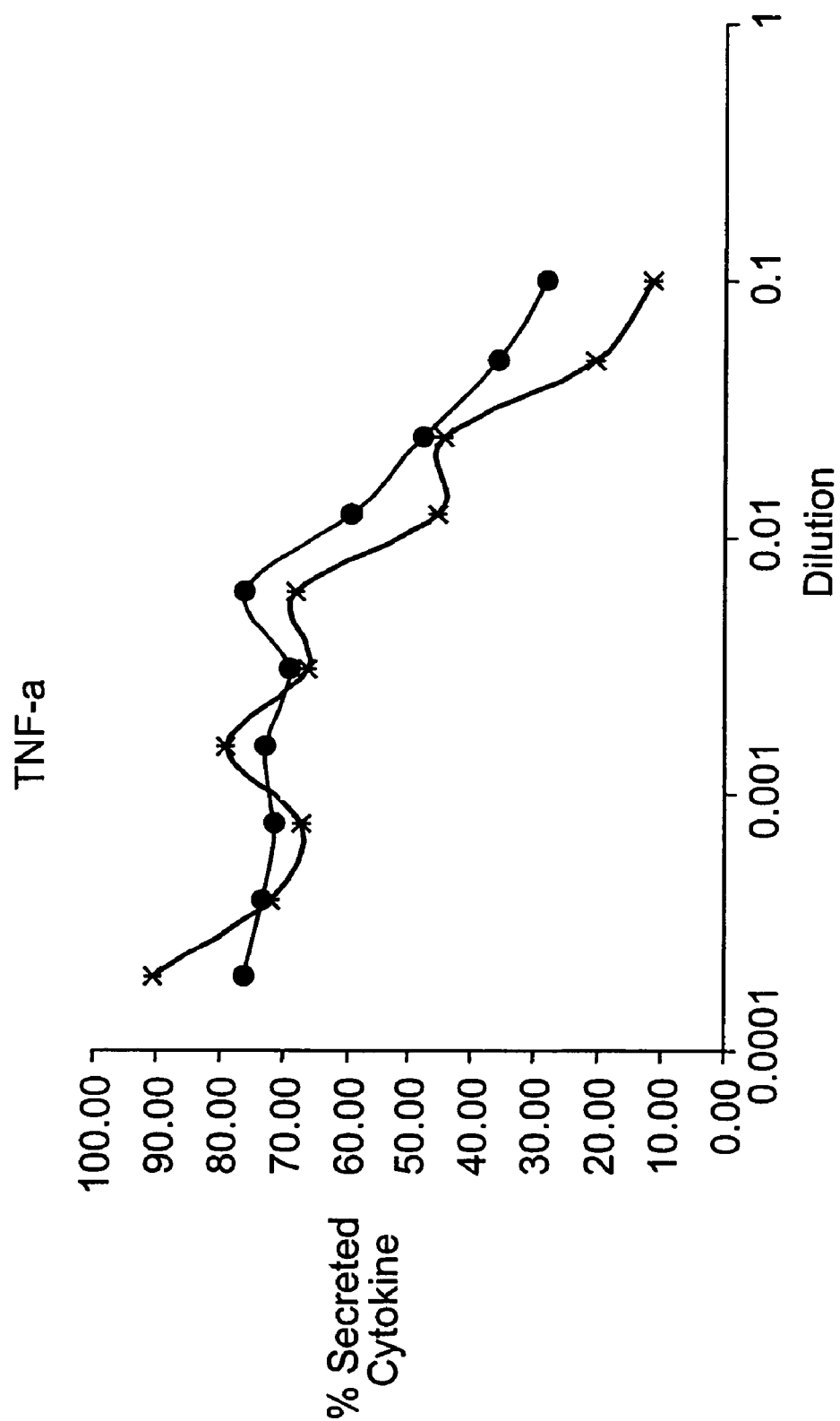

TNF 1h30 mIL6 8h

SEQUENCE LISTING

<160> NUMBER OF SEQ ID NOS: 43

<210> SEQ ID NO 1
<211> LENGTH: 85
<212> TYPE: DNA
<213> ORGANISM: Homo sapiens

<400> SEQUENCE: 1
atgaagagag aaaggggagc cctgtccaga gcctccaggg ccctgcgcct tgctcctttt    60
gtctaccttc ttctgatcca gacag                                         85

<210> SEQ ID NO 2
<211> LENGTH: 29
<212> TYPE: PRT
<213> ORGANISM: Homo sapiens

<400> SEQUENCE: 2

Met Lys Arg Glu Arg Gly Ala Leu Ser Arg Ala Ser Arg Ala Leu Arg
1               5                   10                  15

Leu Ala Pro Phe Val Tyr Leu Leu Leu Ile Gln Thr Asp
            20                  25

<210> SEQ ID NO 3
<211> LENGTH: 342
<212> TYPE: DNA
<213> ORGANISM: Homo sapiens

<400> SEQUENCE: 3

```
accccctgga gggggtgaac atcaccagcc ccgtgcgcct gatccatggc accgtgggga      60
agtcggctct gctttctgtg cagtacagca gtaccagcag cgacaggcct gtagtgaagt    120
ggcagctgaa gcgggacaag ccagtgaccg tggtgcagtc cattggcaca gaggtcatcg    180
gcaccctgcg gcctgactat cgagaccgta tccgactctt tgaaaatggc tccctgcttc    240
tcagcgacct gcagctggcc gatgagggca cctatgaggt cgagatctcc atcaccgacg    300
acaccttcac tggggagaag accatcaacc ttactgtaga tg                      342
```

<210> SEQ ID NO 4
<211> LENGTH: 114
<212> TYPE: PRT
<213> ORGANISM: Homo sapiens

<400> SEQUENCE: 4

Pro Leu Glu Gly Val Asn Ile Thr Ser Pro Val Arg Leu Ile His Gly
1               5                   10                  15

Thr Val Gly Lys Ser Ala Leu Leu Ser Val Gln Tyr Ser Ser Thr Ser
            20                  25                  30

Ser Asp Arg Pro Val Val Lys Trp Gln Leu Lys Arg Asp Lys Pro Val
        35                  40                  45

Thr Val Val Gln Ser Ile Gly Thr Glu Val Ile Gly Thr Leu Arg Pro
    50                  55                  60

Asp Tyr Arg Asp Arg Ile Arg Leu Phe Glu Asn Gly Ser Leu Leu Leu
65                  70                  75                  80

Ser Asp Leu Gln Leu Ala Asp Glu Gly Thr Tyr Glu Val Glu Ile Ser
                85                  90                  95

Ile Thr Asp Thr Phe Thr Gly Glu Lys Thr Ile Asn Leu Thr Val
            100                 105                 110

Asp Val

<210> SEQ ID NO 5
<211> LENGTH: 282
<212> TYPE: DNA
<213> ORGANISM: Homo sapiens

<400> SEQUENCE: 5

```
tgcccatttc gaggccacag gtgttggtgg cttcaaccac tgtgctggag ctcagcgagg      60
ccttcacctt gaactgctca catgagaatg caccaagcc cagctacacc tggctgaagg     120
atggcaagcc cctcctcaat gactcgagaa tgctcctgtc ccccgaccaa aaggtgctca    180
ccatcacccg cgtgctcatg gaggatgacg acctgtacag ctgcatggtg gagaacccca    240
tcagccaggg ccgcagcctg cctgtcaaga tcaccgtata ca                      282
```

<210> SEQ ID NO 6
<211> LENGTH: 94
<212> TYPE: PRT

<213> ORGANISM: Homo sapiens

<400> SEQUENCE: 6

```
Pro Ile Ser Arg Pro Gln Val Leu Val Ala Ser Thr Thr Val Leu Glu
1               5                   10                  15
Leu Ser Glu Ala Phe Thr Leu Asn Cys Ser His Glu Asn Gly Thr Lys
                20                  25                  30
Pro Ser Tyr Thr Trp Leu Lys Asp Gly Lys Pro Leu Leu Asn Asp Ser
            35                  40                  45
Arg Met Leu Leu Ser Pro Asp Gln Lys Val Leu Thr Ile Thr Arg Val
    50                  55                  60
Leu Met Glu Asp Asp Asp Leu Tyr Ser Cys Met Val Glu Asn Pro Ile
65                  70                  75                  80
Ser Gln Gly Arg Ser Leu Pro Val Lys Ile Thr Val Tyr Arg
                85                  90
```

<210> SEQ ID NO 7
<211> LENGTH: 94
<212> TYPE: DNA
<213> ORGANISM: Homo sapiens

<400> SEQUENCE: 7

```
gaagaagctc cctttacatc atcttgtcta caggaggcat cttcctcctt gtgaccttgg    60
tgacagtctg tgcctgctgg aaaccctcca aaag                                94
```

<210> SEQ ID NO 8
<211> LENGTH: 31
<212> TYPE: PRT
<213> ORGANISM: Homo sapiens

<400> SEQUENCE: 8

```
Arg Ser Ser Leu Tyr Ile Ile Leu Ser Thr Gly Gly Ile Phe Leu Leu
1               5                   10                  15
Val Thr Leu Val Thr Val Cys Ala Cys Trp Lys Pro Ser Lys Arg
                20                  25                  30
```

<210> SEQ ID NO 9
<211> LENGTH: 74
<212> TYPE: DNA
<213> ORGANISM: Homo sapiens

<400> SEQUENCE: 9

```
gaaacagaag aagctagaaa agcaaaactc cctggaatac atggatcaga atgatgaccg    60
cctgaaacca gaag                                                      74
```

<210> SEQ ID NO 10
<211> LENGTH: 25
<212> TYPE: PRT
<213> ORGANISM: Homo sapiens

<400> SEQUENCE: 10

```
Lys Gln Lys Lys Leu Glu Lys Gln Asn Ser Leu Glu Tyr Met Asp Gln
1               5                   10                  15
Asn Asp Asp Arg Leu Lys Pro Glu Ala
                20                  25
```

<210> SEQ ID NO 11
<211> LENGTH: 71
<212> TYPE: DNA
<213> ORGANISM: Homo sapiens

<400> SEQUENCE: 11

```
cagacaccct ccctcgaagt ggtgagcagg aacggaagaa ccccatggca ctctatatcc    60
tgaaggacaa g                                                          71
```

<210> SEQ ID NO 12
<211> LENGTH: 23
<212> TYPE: PRT
<213> ORGANISM: Homo sapiens

<400> SEQUENCE: 12

```
Asp Thr Leu Pro Arg Ser Gly Glu Gln Glu Arg Lys Asn Pro Met Ala
1               5                   10                  15

Leu Tyr Ile Leu Lys Asp Lys
            20
```

<210> SEQ ID NO 13
<211> LENGTH: 303
<212> TYPE: DNA
<213> ORGANISM: Homo sapiens

<400> SEQUENCE: 13

```
gactccccgg agaccgagga gaacccggcc ccggagcctc gaagcgcgac ggagcccggc    60
ccgcccggct actccgtgtc tcccgccgtg cccggccgct cgccggggct gcccatccgc   120
tctgcccgcc gctacccgcg ctccccagcg cgctccccag ccaccggccg gacacactcg   180
tcgccgccca gggccccgag ctcgcccggc cgctcgcgca cgcctcgcg cacactgcgg    240 actgcgggcg tgcacataat ccgcgagcaa gacgaggccg gcccggtgga gatcagcgcc   300
tga                                                                 303
```

<210> SEQ ID NO 14
<211> LENGTH: 100
<212> TYPE: PRT
<213> ORGANISM: Homo sapiens

<400> SEQUENCE: 14

```
Asp Ser Pro Glu Thr Glu Glu Asn Pro Ala Pro Glu Pro Arg Ser Ala
1               5                   10                  15

Thr Glu Pro Gly Pro Pro Gly Tyr Ser Val Ser Pro Ala Val Pro Gly
            20                  25                  30

Arg Ser Pro Gly Leu Pro Ile Arg Ser Ala Arg Arg Tyr Pro Arg Ser
        35                  40                  45

Pro Ala Arg Ser Pro Ala Thr Gly Arg Thr His Ser Ser Pro Pro Arg
    50                  55                  60

Ala Pro Ser Ser Pro Gly Arg Ser Arg Ser Ala Ser Arg Thr Leu Arg
65                  70                  75                  80

Thr Ala Gly Val His Ile Ile Arg Glu Gln Asp Glu Ala Gly Pro Val
                85                  90                  95

Glu Ile Ser Ala
            100
```

<210> SEQ ID NO 15
<211> LENGTH: 1251
<212> TYPE: DNA
<213> ORGANISM: Homo sapiens

<400> SEQUENCE: 15

```
atgaagagag aaaggggagc cctgtccaga gcctccaggg ccctgcgcct tgctcctttt    60
```

-continued

```
gtctaccttc ttctgatcca gacagacccc ctggaggggg tgaacatcac cagccccgtg    120
cgcctgatcc atggcaccgt ggggaagtcg gctctgcttt ctgtgcagta cagcagtacc    180
agcagcgaca ggcctgtagt gaagtggcag ctgaagcggg acaagccagt gaccgtggtg    240
cagtccattg gcacagaggt catcggcacc ctgcggcctg actatcgaga ccgtatccga    300
ctctttgaaa atggctccct gcttctcagc gacctgcagc tggccgatga gggcacctat    360
gaggtcgaga tctccatcac cgacgacacc ttcactgggg agaagaccat caaccttact    420
gtagatgtgc ccatttcgag gccacaggtg ttggtggctt caaccactgt gctggagctc    480
agcgaggcct tcaccttgaa ctgctcacat gagaatggca ccaagcccag ctacacctgg    540
ctgaaggatg gcaagcccct cctcaatgac tcgagaatgc tcctgtcccc cgaccaaaag    600
gtgctcacca tcacccgcgt gctcatggag gatgacgacc tgtacagctg catggtggag    660
aaccccatca gccagggccg cagcctgcct gtcaagatca ccgtatacag aagaagctcc    720
ctttacatca tcttgtctac aggaggcatc ttcctccttg tgaccttggt gacagtctgt    780
gcctgctgga aaccctccaa aaggaaacag aagaagctag aaaagcaaaa ctccctggaa    840
tacatggatc agaatgatga ccgcctgaaa ccagaagcag acaccctccc tcgaagtggt    900
gagcaggaac ggaagaaccc catggcactc tatatcctga aggacaagga ctccccggag    960
accgaggaga acccggcccc ggagcctcga agcgcgacgg agcccggccc gcccggctac   1020
tccgtgtctc ccgccgtgcc cggccgctcg ccggggctgc ccatccgctc tgcccgccgc   1080
tacccgcgct ccccagcgcg ctccccagcc accggccgga cacactcgtc gccgcccagg   1140
gccccgagct cgcccggccg ctcgcgcagc gcctcgcgca cactgcggac tgcgggcgtg   1200
cacataatcc gcgagcaaga cgaggccggc ccggtggaga tcagcgcctg a            1251
```

<210> SEQ ID NO 16
<211> LENGTH: 416
<212> TYPE: PRT
<213> ORGANISM: Homo sapiens

<400> SEQUENCE: 16

```
Met Lys Arg Glu Arg Gly Ala Leu Ser Arg Ala Ser Arg Ala Leu Arg
1               5                   10                  15

Leu Ala Pro Phe Val Tyr Leu Leu Ile Gln Thr Asp Pro Leu Glu
            20                  25                  30

Gly Val Asn Ile Thr Ser Pro Val Arg Leu Ile His Gly Thr Val Gly
        35                  40                  45

Lys Ser Ala Leu Leu Ser Val Gln Tyr Ser Ser Thr Ser Ser Asp Arg
    50                  55                  60

Pro Val Val Lys Trp Gln Leu Lys Arg Asp Lys Pro Val Thr Val Val
65                  70                  75                  80

Gln Ser Ile Gly Thr Glu Val Ile Gly Thr Leu Arg Pro Asp Tyr Arg
                85                  90                  95

Asp Arg Ile Arg Leu Phe Glu Asn Gly Ser Leu Leu Leu Ser Asp Leu
            100                 105                 110

Gln Leu Ala Asp Glu Gly Thr Tyr Glu Val Glu Ile Ser Ile Thr Asp
        115                 120                 125

Asp Thr Phe Thr Gly Glu Lys Thr Ile Asn Leu Thr Val Asp Val Pro
    130                 135                 140

Ile Ser Arg Pro Gln Val Leu Val Ala Ser Thr Thr Val Leu Glu Leu
145                 150                 155                 160
```

```
Ser Glu Ala Phe Thr Leu Asn Cys Ser His Glu Asn Gly Thr Lys Pro
            165                 170                 175

Ser Tyr Thr Trp Leu Lys Asp Gly Lys Pro Leu Leu Asn Asp Ser Arg
        180                 185                 190

Met Leu Leu Ser Pro Asp Gln Lys Val Leu Thr Ile Thr Arg Val Leu
    195                 200                 205

Met Glu Asp Asp Asp Leu Tyr Ser Cys Met Val Glu Asn Pro Ile Ser
210                 215                 220

Gln Gly Arg Ser Leu Pro Val Lys Ile Thr Val Tyr Arg Arg Ser Ser
225                 230                 235                 240

Leu Tyr Ile Ile Leu Ser Thr Gly Gly Ile Phe Leu Leu Val Thr Leu
                245                 250                 255

Val Thr Val Cys Ala Cys Trp Lys Pro Ser Lys Arg Lys Gln Lys Lys
            260                 265                 270

Leu Glu Lys Gln Asn Ser Leu Glu Tyr Met Asp Gln Asn Asp Asp Arg
        275                 280                 285

Leu Lys Pro Glu Ala Asp Thr Leu Pro Arg Ser Gly Glu Gln Glu Arg
    290                 295                 300

Lys Asn Pro Met Ala Leu Tyr Ile Leu Lys Asp Lys Asp Ser Pro Glu
305                 310                 315                 320

Thr Glu Glu Asn Pro Ala Pro Glu Pro Arg Ser Ala Thr Glu Pro Gly
                325                 330                 335

Pro Pro Gly Tyr Ser Val Ser Pro Ala Val Pro Gly Arg Ser Pro Gly
            340                 345                 350

Leu Pro Ile Arg Ser Ala Arg Arg Tyr Pro Arg Ser Pro Ala Arg Ser
        355                 360                 365

Pro Ala Thr Gly Arg Thr His Ser Ser Pro Pro Arg Ala Pro Ser Ser
    370                 375                 380

Pro Gly Arg Ser Arg Ser Ala Ser Arg Thr Leu Arg Thr Ala Gly Val
385                 390                 395                 400

His Ile Ile Arg Glu Gln Asp Glu Ala Gly Pro Val Glu Ile Ser Ala
                405                 410                 415

<210> SEQ ID NO 17
<211> LENGTH: 1257
<212> TYPE: DNA
<213> ORGANISM: Homo sapiens

<400> SEQUENCE: 17
atgaagagag aaaggggagc cctgtcaaga gcctccaggg ctctgcgcct ctctcctttt      60
gtctacctgc ttctcatcca gccagtcccc ctggaggggg tgaacatcac cagcccagta     120
cgtctgatcc acggcacagt ggggaagtcg gccctgcttt ccgtgcagta cagtagcacc     180
agcagcgaca gcccgtggt gaagtggcag ctgaagcgtg acaagccagt gaccgtggtg     240
cagtctatag gcacagaggt cattggcact ctgcggcctg actatcgaga ccgtatccgg     300
ctctttgaaa tggctccctt gcttctcagc gacctgcagc tggcggatga gggaacctat     360
gaagtggaga tttccatcac tgacgacacc ttcaccgggg agaagaccat caacctcacc     420
gtggatgtgc ccatttcaag gccgcaggta ttagtggctt caaccactgt gctggagctc     480
agtgaggcct tcaccctcaa ctgctcccat gagaatggca ccaagcctag ctacacgtgg     540
ctgaaggatg gcaaaccccct cctcaatgac tcccgaatgc tcctgtcccc tgaccaaaag     600
gtgctcacca tcacccgagt actcatggaa gatgacgacc tgtacagctg tgtggtggag     660
aaccccatca gccagggtcc gagcctgcct gtcaagatca ctgtgtatag aagaagctcc     720
```

```
ctctatatca tcttgtctac aggaggcatc ttcctccttg tgaccctggt gacagtttgt    780
gcctgctgga aaccctcaaa aaagtctagg aagaagagga agttggagaa gcaaaactcc    840
ttggaataca tggatcagaa tgatgaccgc ctaaaatcag aagcagatac cctaccccga    900
agtggagaac aggagcggaa gaacccaatg gcactctata tcctgaagga taaggattcc    960
tcagagccag atgaaaaccc tgctacagag ccacggagca ccacagaacc cggtcccccct   1020 ggctactccg tgtcgccgcc cgtgcccggc cgctctccgg ggcttcccat ccgctcagcc   1080
cgccgctacc cgcgctcccc agcacgttcc cctgccactg gccggacgca cacgtcgcca   1140
ccgcgggccc cgagctcgcc aggccgctcg cgcagctctt cgcgctcact gcggactgca   1200
ggcgtgcaga gaatccggga gcaggacgag tcagggcagg tggagatcag tgcctga      1257
```

<210> SEQ ID NO 18
<211> LENGTH: 418
<212> TYPE: PRT
<213> ORGANISM: Homo sapiens

<400> SEQUENCE: 18

```
Met Lys Arg Glu Arg Gly Ala Leu Ser Arg Ala Ser Arg Ala Leu Arg
1               5                   10                  15

Leu Ser Pro Phe Val Tyr Leu Leu Ile Gln Pro Val Pro Leu Glu
            20                  25                  30

Gly Val Asn Ile Thr Ser Pro Val Arg Leu Ile His Gly Thr Val Gly
        35                  40                  45

Lys Ser Ala Leu Leu Ser Val Gln Tyr Ser Ser Thr Ser Ser Asp Lys
    50                  55                  60

Pro Val Val Lys Trp Gln Leu Lys Arg Asp Lys Pro Val Thr Val Val
65                  70                  75                  80

Gln Ser Ile Gly Thr Glu Val Ile Gly Thr Leu Arg Pro Asp Tyr Arg
                85                  90                  95

Asp Arg Ile Arg Leu Phe Glu Asn Gly Ser Leu Leu Leu Ser Asp Leu
            100                 105                 110

Gln Leu Ala Asp Glu Gly Thr Tyr Glu Val Glu Ile Ser Ile Thr Asp
        115                 120                 125

Asp Thr Phe Thr Gly Glu Lys Thr Ile Asn Leu Thr Val Asp Val Pro
    130                 135                 140

Ile Ser Arg Pro Gln Val Leu Val Ala Ser Thr Val Leu Glu Leu
145                 150                 155                 160

Ser Glu Ala Phe Thr Leu Asn Cys Ser His Glu Asn Gly Thr Lys Pro
                165                 170                 175

Ser Tyr Thr Trp Leu Lys Asp Gly Lys Pro Leu Leu Asn Asp Ser Arg
            180                 185                 190

Met Leu Leu Ser Pro Asp Gln Lys Val Leu Thr Ile Thr Arg Val Leu
        195                 200                 205

Met Glu Asp Asp Asp Leu Tyr Ser Cys Val Val Glu Asn Pro Ile Ser
    210                 215                 220

Gln Val Arg Ser Leu Pro Val Lys Ile Thr Val Tyr Arg Arg Ser Ser
225                 230                 235                 240

Leu Tyr Ile Ile Leu Ser Thr Gly Gly Ile Phe Leu Leu Val Thr Leu
                245                 250                 255

Val Thr Val Cys Ala Cys Trp Lys Pro Ser Lys Ser Arg Lys Lys
            260                 265                 270

Arg Lys Leu Glu Lys Gln Asn Ser Leu Glu Tyr Met Asp Gln Asn Asp
```

-continued

```
               275                 280                 285
Asp Arg Leu Lys Ser Glu Ala Asp Thr Leu Pro Arg Ser Gly Glu Gln
    290                 295                 300

Glu Arg Lys Asn Pro Met Ala Leu Tyr Ile Leu Lys Asp Lys Asp Ser
305                 310                 315                 320

Ser Glu Pro Asp Glu Asn Pro Ala Thr Glu Pro Arg Ser Thr Thr Glu
            325                 330                 335

Pro Gly Pro Pro Gly Tyr Ser Val Ser Pro Val Pro Gly Arg Ser
        340                 345                 350

Pro Gly Leu Pro Ile Arg Ser Ala Arg Arg Tyr Pro Arg Ser Pro Ala
        355                 360                 365

Arg Ser Pro Ala Thr Gly Arg Thr His Thr Ser Pro Pro Arg Ala Pro
    370                 375                 380

Ser Ser Pro Gly Arg Ser Arg Ser Ser Ser Ser Leu Arg Thr Ala
385                 390                 395                 400

Gly Val Gln Arg Ile Arg Glu Gln Asp Glu Ser Gly Gln Val Glu Ile
                405                 410                 415

Ser Ala
```

<210> SEQ ID NO 19
<211> LENGTH: 720
<212> TYPE: DNA
<213> ORGANISM: Homo sapiens

<400> SEQUENCE: 19

```
atgaagagag aaaggggagc cctgtccaga gcctccaggg ccctgcgcct tgctcctttt      60
gtctaccttc ttctgatcca gacagacccc ctggaggggg tgaacatcac cagccccgtg    120
cgcctgatcc atggcaccgt ggggaagtcg gctctgcttt ctgtgcagta cagcagtacc    180
agcagcgaca ggcctgtagt gaagtggcag ctgaagcggg acaagccagt gaccgtggtg    240
cagtccattg gcacagaggt catcggcacc ctgcggcctg actatcgaga ccgtatccga    300
ctctttgaaa atggctccct gcttctcagc gacctgcagc tggccgatga gggcacctat    360
gaggtcgaga tctccatcac cgacgacacc ttcactgggg agaagaccat caaccttact    420
gtagatgtgc ccatttcgag gccacaggtg ttggtggctt caaccactgt gctggagctc    480
agcgaggcct tcaccttgaa ctgctcacat gagaatggca ccaagcccag ctacacctgg    540
ctgaaggatg gcaagcccct cctcaatgac tcgagaatgc tcctgtcccc cgaccaaaag    600
gtgctcacca tcacccgcgt gctcatggag gatgacgacc tgtacagctg catggtggag    660
aaccccatca gccagggccg cagcctgcct gtcaagatca ccgtatacag aagaagctcc    720
```

<210> SEQ ID NO 20
<211> LENGTH: 240
<212> TYPE: PRT
<213> ORGANISM: Homo sapiens

<400> SEQUENCE: 20

```
Met Lys Arg Glu Arg Gly Ala Leu Ser Arg Ala Ser Arg Ala Leu Arg
1               5                   10                  15

Leu Ala Pro Phe Val Tyr Leu Leu Leu Ile Gln Thr Asp Pro Leu Glu
            20                  25                  30

Gly Val Asn Ile Thr Ser Pro Val Arg Leu Ile His Gly Thr Val Gly
        35                  40                  45

Lys Ser Ala Leu Leu Ser Val Gln Tyr Ser Ser Thr Ser Ser Asp Arg
    50                  55                  60
```

Pro Val Val Lys Trp Gln Leu Lys Arg Asp Lys Pro Val Thr Val Val
65                  70                  75                  80

Gln Ser Ile Gly Thr Glu Val Ile Gly Thr Leu Arg Pro Asp Tyr Arg
                85                  90                  95

Asp Arg Ile Arg Leu Phe Glu Asn Gly Ser Leu Leu Ser Asp Leu
            100                 105                 110

Gln Leu Ala Asp Glu Gly Thr Tyr Glu Val Glu Ile Ser Ile Thr Asp
            115                 120                 125

Asp Thr Phe Thr Gly Glu Lys Thr Ile Asn Leu Thr Val Asp Val Pro
    130                 135                 140

Ile Ser Arg Pro Gln Val Leu Ala Ser Thr Thr Val Leu Glu Leu
145                 150                 155                 160

Ser Glu Ala Phe Thr Leu Asn Cys Ser His Glu Asn Gly Thr Lys Pro
                165                 170                 175

Ser Tyr Thr Trp Leu Lys Asp Gly Lys Pro Leu Leu Asn Asp Ser Arg
            180                 185                 190

Met Leu Leu Ser Pro Asp Gln Lys Val Leu Thr Ile Thr Arg Val Leu
            195                 200                 205

Met Glu Asp Asp Asp Leu Tyr Ser Cys Met Val Glu Asn Pro Ile Ser
    210                 215                 220

Gln Gly Arg Ser Leu Pro Val Lys Ile Thr Val Tyr Arg Arg Ser Ser
225                 230                 235                 240

<210> SEQ ID NO 21
<211> LENGTH: 621
<212> TYPE: DNA
<213> ORGANISM: Homo sapiens

<400> SEQUENCE: 21
gtgaacatca ccagccccgt gcgcctgatc catggcaccg tggggaagtc ggctctgctt    60
tctgtgcagt acagcagtac cagcagcgac aggcctgtag tgaagtggca gctgaagcgg   120
gacaagccag tgaccgtggt gcagtccatt ggcacagagg tcatcggcac cctgcggcct   180
gactatcgag accgtatccg actctttgaa atggctccc tgcttctcag cgacctgcag    240
ctggccgatg agggcaccta tgaggtcgag atctccatca ccgacgacac cttcactggg   300
gagaagacca tcaaccttac tgtagatgtg cccatttcga ggccacaggt gttggtggct   360
tcaaccactg tgctggagct cagcgaggcc ttcaccttga actgctcaca tgagaatggc   420
accaagccca gctacacctg gctgaaggat ggcaagcccc tcctcaatga ctcgagaatg   480
ctcctgtccc ccgaccaaaa ggtgctcacc atcacccgcg tgctcatgga ggatgacgac   540
ctgtacagct gcatggtgga gaaccccatc agccagggcc gcagcctgcc tgtcaagatc   600
accgtataca gaagaagctc c                                             621

<210> SEQ ID NO 22
<211> LENGTH: 207
<212> TYPE: PRT
<213> ORGANISM: Homo sapiens

<400> SEQUENCE: 22

Val Asn Ile Thr Ser Pro Val Arg Leu Ile His Gly Thr Val Gly Lys
1               5                   10                  15

Ser Ala Leu Leu Ser Val Gln Tyr Ser Ser Thr Ser Ser Asp Arg Pro
            20                  25                  30

Val Val Lys Trp Gln Leu Lys Arg Asp Lys Pro Val Thr Val Val Gln

```
                35                  40                  45
Ser Ile Gly Thr Glu Val Ile Gly Thr Leu Arg Pro Asp Tyr Arg Asp
    50                  55                  60

Arg Ile Arg Leu Phe Glu Asn Gly Ser Leu Leu Leu Ser Asp Leu Gln
65                  70                  75                  80

Leu Ala Asp Glu Gly Thr Tyr Glu Val Glu Ile Ser Ile Thr Asp Asp
                85                  90                  95

Thr Phe Thr Gly Glu Lys Thr Ile Asn Leu Thr Val Asp Val Pro Ile
            100                 105                 110

Ser Arg Pro Gln Val Leu Val Ala Ser Thr Thr Val Leu Glu Leu Ser
        115                 120                 125

Glu Ala Phe Thr Leu Asn Cys Ser His Glu Asn Gly Thr Lys Pro Ser
    130                 135                 140

Tyr Thr Trp Leu Lys Asp Gly Lys Pro Leu Leu Asn Asp Ser Arg Met
145                 150                 155                 160

Leu Leu Ser Pro Asp Gln Lys Val Leu Thr Ile Thr Arg Val Leu Met
                165                 170                 175

Glu Asp Asp Asp Leu Tyr Ser Cys Met Val Glu Asn Pro Ile Ser Gln
            180                 185                 190

Gly Arg Ser Leu Pro Val Lys Ile Thr Val Tyr Arg Arg Ser Ser
        195                 200                 205

<210> SEQ ID NO 23
<211> LENGTH: 328
<212> TYPE: DNA
<213> ORGANISM: Homo sapiens

<400> SEQUENCE: 23
gtgaacatca ccagccccgt gcgcctgatc catggcaccg tggggaagtc ggctctgctt    60
tctgtgcagt acagcagtac cagcagcgac aggcctgtag tgaagtggca gctgaagcgg   120
gacaagccag tgaccgtggt gcagtccatt ggcacagagg tcatcggcac cctgcggcct   180
gactatcgag accgtatccg actctttgaa aatggctccc tgcttctcag cgacctgcag   240
ctggccgatg agggcaccta tgaggtcgag atctccatca ccgacgacac cttcactggg   300
gagaagacca tcaaccttac tgtagatg                                     328

<210> SEQ ID NO 24
<211> LENGTH: 110
<212> TYPE: PRT
<213> ORGANISM: Homo sapiens

<400> SEQUENCE: 24

Val Asn Ile Thr Ser Pro Val Arg Leu Ile His Gly Thr Val Gly Lys
1               5                   10                  15

Ser Ala Leu Leu Ser Val Gln Tyr Ser Ser Thr Ser Ser Asp Arg Pro
            20                  25                  30

Val Val Lys Trp Gln Leu Lys Arg Asp Lys Pro Val Thr Val Val Gln
        35                  40                  45

Ser Ile Gly Thr Glu Val Ile Gly Thr Leu Arg Pro Asp Tyr Arg Asp
    50                  55                  60

Arg Ile Arg Leu Phe Glu Asn Gly Ser Leu Leu Leu Ser Asp Leu Gln
65                  70                  75                  80

Leu Ala Asp Glu Gly Thr Tyr Glu Val Glu Ile Ser Ile Thr Asp Asp
                85                  90                  95

Thr Phe Thr Gly Glu Lys Thr Ile Asn Leu Thr Val Asp Val
            100                 105
```

<210> SEQ ID NO 25
<211> LENGTH: 1152
<212> TYPE: DNA
<213> ORGANISM: Homo sapiens

<400> SEQUENCE: 25

```
gtgaacatca ccagccccgt gcgcctgatc catggcaccg tggggaagtc ggctctgctt      60
tctgtgcagt acagcagtac cagcagcgac aggcctgtag tgaagtggca gctgaagcgg     120
gacaagccag tgaccgtggt gcagtccatt ggcacagagg tcatcggcac cctgcggcct     180
gactatcgag accgtatccg actctttgaa aatggctccc tgcttctcag cgacctgcag     240
ctggccgatg agggcaccta tgaggtcgag atctccatca ccgacgacac cttcactggg     300
gagaagacca tcaaccttac tgtagatgtg cccatttcga ggccacaggt gttggtggct     360
tcaaccactg tgctggagct cagcgaggcc ttcaccttga actgctcaca tgagaatggc     420
accaagccca gctacacctg gctgaaggat ggcaagcccc tcctcaatga ctcgagaatg     480
ctcctgtccc ccgaccaaaa ggtgctcacc atcacccgcg tgctcatgga ggatgacgac     540
ctgtacagct gcatggtgga aaccccatc agccagggcc gcagcctgcc tgtcaagatc     600
accgtataca aagaagctc cctttacatc atcttgtcta caggaggcat cttcctcctt     660
gtgaccttgg tgacagtctg tgcctgctgg aaaccctcca aaaggaaaca aagaagcta     720
gaaaagcaaa actccctgga atacatggat cagaatgatg accgcctgaa accagaagca     780
gacaccctcc ctcgaagtgg tgagcaggaa cggaagaacc ccatggcact ctatatcctg     840
aaggacaagg actccccgga gaccgaggag aacccggccc cggagcctcg aagcgcgacg     900
gagcccggcc cgcccggcta ctccgtgtct cccgccgtgc ccggccgctc gccggggctg     960
cccatccgct ctgcccgccg ctacccgcgc tccccagcgc gctccccagc caccggccgg    1020
acacactcgt cgccgccag gccccgagc tcgcccggcc gctcgcgcag cgcctcgcgc    1080
acactgcgga ctgcgggcgt gcacataatc cgcgagcaag acgaggccgg cccggtggag    1140
atcagcgcct ga                                                        1152
```

<210> SEQ ID NO 26
<211> LENGTH: 383
<212> TYPE: PRT
<213> ORGANISM: Homo sapiens

<400> SEQUENCE: 26

```
Val Asn Ile Thr Ser Pro Val Arg Leu Ile His Gly Thr Val Gly Lys
1               5                   10                  15

Ser Ala Leu Leu Ser Val Gln Tyr Ser Ser Thr Ser Ser Asp Arg Pro
                20                  25                  30

Val Val Lys Trp Gln Leu Lys Arg Asp Lys Pro Val Thr Val Val Gln
            35                  40                  45

Ser Ile Gly Thr Glu Val Ile Gly Thr Leu Arg Pro Asp Tyr Arg Asp
        50                  55                  60

Arg Ile Arg Leu Phe Glu Asn Gly Ser Leu Leu Leu Ser Asp Leu Gln
65                  70                  75                  80

Leu Ala Asp Glu Gly Thr Tyr Glu Val Glu Ile Ser Ile Thr Asp Asp
                85                  90                  95

Thr Phe Thr Gly Glu Lys Thr Ile Asn Leu Thr Val Asp Val Pro Ile
                100                 105                 110
```

```
Ser Arg Pro Gln Val Leu Val Ala Ser Thr Thr Val Leu Glu Leu Ser
        115                 120                 125

Glu Ala Phe Thr Leu Asn Cys Ser His Glu Asn Gly Thr Lys Pro Ser
130                 135                 140

Tyr Thr Trp Leu Lys Asp Gly Lys Pro Leu Leu Asn Asp Ser Arg Met
145                 150                 155                 160

Leu Leu Ser Pro Asp Gln Lys Val Leu Thr Ile Thr Arg Val Leu Met
                165                 170                 175

Glu Asp Asp Asp Leu Tyr Ser Cys Met Val Glu Asn Pro Ile Ser Gln
                180                 185                 190

Gly Arg Ser Leu Pro Val Lys Ile Thr Val Tyr Arg Ser Ser Leu
        195                 200                 205

Tyr Ile Ile Leu Ser Thr Gly Gly Ile Phe Leu Leu Val Thr Leu Val
210                 215                 220

Thr Val Cys Ala Cys Trp Lys Pro Ser Lys Arg Lys Gln Lys Lys Leu
225                 230                 235                 240

Glu Lys Gln Asn Ser Leu Glu Tyr Met Asp Gln Asn Asp Asp Arg Leu
                245                 250                 255

Lys Pro Glu Ala Asp Thr Leu Pro Arg Ser Gly Glu Gln Glu Arg Lys
                260                 265                 270

Asn Pro Met Ala Leu Tyr Ile Leu Lys Asp Lys Asp Ser Pro Glu Thr
        275                 280                 285

Glu Glu Asn Pro Ala Pro Glu Pro Arg Ser Ala Thr Glu Pro Gly Pro
290                 295                 300

Pro Gly Tyr Ser Val Ser Pro Ala Val Pro Gly Arg Ser Pro Gly Leu
305                 310                 315                 320

Pro Ile Arg Ser Ala Arg Arg Tyr Pro Arg Ser Pro Ala Arg Ser Pro
                325                 330                 335

Ala Thr Gly Arg Thr His Ser Ser Pro Pro Arg Ala Pro Ser Ser Pro
                340                 345                 350

Gly Arg Ser Arg Ser Ala Ser Arg Thr Leu Arg Thr Ala Gly Val His
        355                 360                 365

Ile Ile Arg Glu Gln Asp Glu Ala Gly Pro Val Glu Ile Ser Ala
        370                 375                 380

<210> SEQ ID NO 27
<211> LENGTH: 37
<212> TYPE: DNA
<213> ORGANISM: Artificial Sequence
<220> FEATURE:
<223> OTHER INFORMATION: GCP Forward Primer

<400> SEQUENCE: 27
ggggacaagt ttgtacaaaa aagcaggctt cgccacc                              37

<210> SEQ ID NO 28
<211> LENGTH: 51
<212> TYPE: DNA
<213> ORGANISM: Artificial Sequence
<220> FEATURE:
<223> OTHER INFORMATION: GCP Reverse Primer

<400> SEQUENCE: 28
ggggaccact ttgtacaaga aagctgggtt tcaatggtga tggtgatggt g              51

<210> SEQ ID NO 29
<211> LENGTH: 41
<212> TYPE: DNA
```

<213> ORGANISM: Artificial Sequence
<220> FEATURE:
<223> OTHER INFORMATION: INSP052-B1P-exon1F Primer

<400> SEQUENCE: 29
gcaggcttcg ccaccatgaa gagagaaagg ggagccctgt c        41

<210> SEQ ID NO 30
<211> LENGTH: 36
<212> TYPE: DNA
<213> ORGANISM: Artificial Sequence
<220> FEATURE:
<223> OTHER INFORMATION: INSP052-exon1R Primer

<400> SEQUENCE: 30
tcaccccctc caggggtct gtctggatca gaagaa              36

<210> SEQ ID NO 31
<211> LENGTH: 36
<212> TYPE: DNA
<213> ORGANISM: Artificial Sequence
<220> FEATURE:
<223> OTHER INFORMATION: INSP052-exon2F Primer

<400> SEQUENCE: 31
ttcttctgat ccagacagac ccctggagg gggtga              36

<210> SEQ ID NO 32
<211> LENGTH: 36
<212> TYPE: DNA
<213> ORGANISM: Artificial Sequence
<220> FEATURE:
<223> OTHER INFORMATION: INSP052-exon2R Primer

<400> SEQUENCE: 32
gtggcctcga aatgggcaca tctacagtaa ggttga              36

<210> SEQ ID NO 33
<211> LENGTH: 36
<212> TYPE: DNA
<213> ORGANISM: Artificial Sequence
<220> FEATURE:
<223> OTHER INFORMATION: INSP052-exon3F Primer

<400> SEQUENCE: 33
caaccttact gtagatgtgc ccatttcgag gccaca              36

<210> SEQ ID NO 34
<211> LENGTH: 32
<212> TYPE: DNA
<213> ORGANISM: Artificial Sequence
<220> FEATURE:
<223> OTHER INFORMATION: INSP052-exon3R Primer

<400> SEQUENCE: 34
ggagcttctt ctgtatacgg tgatcttgac ag                  32

<210> SEQ ID NO 35
<211> LENGTH: 35
<212> TYPE: DNA
<213> ORGANISM: Artificial Sequence
<220> FEATURE:
<223> OTHER INFORMATION: INSP052-5HIS-R Primer

<400> SEQUENCE: 35
gtgatggtga tggtgggagc ttcttctgta tacgg              35

<210> SEQ ID NO 36
<211> LENGTH: 20
<212> TYPE: DNA
<213> ORGANISM: Artificial Sequence
<220> FEATURE:
<223> OTHER INFORMATION: pEAK12-F Primer

<400> SEQUENCE: 36
gccagcttgg cacttgatgt                                         20

<210> SEQ ID NO 37
<211> LENGTH: 20
<212> TYPE: DNA
<213> ORGANISM: Artificial Sequence
<220> FEATURE:
<223> OTHER INFORMATION: pEAK12-R Primer

<400> SEQUENCE: 37
gatggaggtg gacgtgtcag                                         20

<210> SEQ ID NO 38
<211> LENGTH: 25
<212> TYPE: DNA
<213> ORGANISM: Artificial Sequence
<220> FEATURE:
<223> OTHER INFORMATION: pENTR-F1 Primer

<400> SEQUENCE: 38
tcgcgttaac gctagcatgg atctc                                   25

<210> SEQ ID NO 39
<211> LENGTH: 24
<212> TYPE: DNA
<213> ORGANISM: Artificial Sequence
<220> FEATURE:
<223> OTHER INFORMATION: pENTR-R1 Primer

<400> SEQUENCE: 39
gtaacatcag agattttgag acac                                    24

<210> SEQ ID NO 40
<211> LENGTH: 2024
<212> TYPE: DNA
<213> ORGANISM: Homo sapiens

<400> SEQUENCE: 40
atgaagagag aaaggggagc cctgtccaga gcctccaggg ccctgcgcct tgctccttt     60 gtctaccttc ttctgatcca gacagacccc ctggagggg tgaacatcac cagccccgtg   120
cgcctgatcc atggcaccgt ggggaagtcg gctctgcttt ctgtgcagta cagcagtacc   180
agcagcgaca ggcctgtagt gaagtggcag ctgaagcggg acaagccagt gaccgtggtg   240
cagtccattg gcacagaggt catcggcacc ctgcggcctg actatcgaga ccgtatccga   300
ctctttgaaa tggctcccct gcttctcagc gacctgcagc tggccgatga gggcacctat   360
gaggtcgaga tctccatcac cgacgacacc ttcactgggg agaagaccat caaccttact   420
gtagatgtgc ccatttcgag gccacaggtg ttggtggctt caaccactgt gctggagctc   480
agcgaggcct tcaccttgaa ctgctcacat gagaatggca ccaagcccag ctacacctgg   540
ctgaaggatg gcaagcccct cctcaatgac tcgagaatgc tcctgtcccc cgaccaaaag   600
gtgctcacca tcacccgcgt gctcatggag gatgacgacc tgtacagctg catggtggag   660

```
aacccccatca gccagggccg cagcctgcct gtcaagatca ccgtatacag aagaagctcc     720
ctttacatca tcttgtctac aggaggcatc ttcctccttg tgaccttggt gacagtctgt     780
gcctgctgga aaccctccaa aaggaaacag aagaagctag aaaagcaaaa ctccctggaa     840
tacatggatc agaatgatga ccgcctgaaa ccagaagcag acaccctccc tcgaagtggt     900
gagcaggaac ggaagaaccc catggcactc tatatcctga aggacaagga ctccccggag     960
accgaggaga acccggcccc ggagcctcga agcgcgacgg agcccggccc gcccggctac    1020
tccgtgtctc ccgccgtgcc cggccgctcg ccggggctgc ccatccgctc tgcccgccgc    1080
tacccgcgct ccccagcgcg ctccccagcc accggccgga cacactcgtc gccgcccagg    1140
gccccgagct cgcccggccg ctcgcgcagc gcctcgcgca cactgcggac tgcgggcgtg    1200
cacataatcc gcgagcaaga cgaggccggc ccggtggaga tcagcgcctg agccgcctcg    1260
gatcccctga gaggcgcccg cggtctgcgg ccagtggccc gggggaaagc tggggctggg    1320
aagcccgggc gcggcgcgct ggggacgagg ggaggtcccg gggggggcgct ggtgtctcgg    1380 gtgtgaacgt gtatgagcat gcgcagacgg aggcgggtgc gcggaggcgg cagtgttgat    1440
atggtgaaac cgggtcgcat ttgcttccgg tttactggct gtgtcctcac ttggtatagg    1500
ttgtgccctc ttaggaccac atagattatt acatttctgg cccaataccc aaaagggttt    1560
tatgaaaact aacatcagta acctaacccc cgtgactatc ctgtgctctt cctagggagc    1620
tgtgttgttt cccacccacc acccttccct ctgaacaaat gcctgagtgc tggggcactt    1680
tttttttttt tttttttttt ttttttttttg caagttcaga ttagagaggc cactttccca    1740
gaatccacag ctgcactaag ctaaggagaa gccagatgcc ggttactggg tgtgcagggg    1800
ctgttctgag ctgggggggat cattgtgaag gccttcttcc ctgggcacct ggtacctggg    1860
gacctacaag gtggtgaggg aagggtacga gtacattcct tttccctctg acctgggcgc    1920
tagcaagggc aaagaacccg agcctgccag cttggcctcc tcccacagcc tccctcggag    1980
gcatgccatg ccaagcactc tttctgtctc tgttcatgaa taaa                      2024
```

<210> SEQ ID NO 41
<211> LENGTH: 416
<212> TYPE: PRT
<213> ORGANISM: Homo sapiens

<400> SEQUENCE: 41

```
Met Lys Arg Glu Arg Gly Ala Leu Ser Arg Ala Ser Arg Ala Leu Arg
1               5                   10                  15

Leu Ala Pro Phe Val Tyr Leu Leu Ile Gln Thr Asp Pro Leu Glu
            20                  25                  30

Gly Val Asn Ile Thr Ser Pro Val Arg Leu Ile His Gly Thr Val Gly
        35                  40                  45

Lys Ser Ala Leu Leu Ser Val Gln Tyr Ser Ser Thr Ser Ser Asp Arg
    50                  55                  60

Pro Val Val Lys Trp Gln Leu Lys Arg Asp Lys Pro Val Thr Val Val
65                  70                  75                  80

Gln Ser Ile Gly Thr Glu Val Ile Gly Thr Leu Arg Pro Asp Tyr Arg
                85                  90                  95

Asp Arg Ile Arg Leu Phe Glu Asn Gly Ser Leu Leu Leu Ser Asp Leu
            100                 105                 110

Gln Leu Ala Asp Glu Gly Thr Tyr Glu Val Glu Ile Ser Ile Thr Asp
        115                 120                 125

Asp Thr Phe Thr Gly Glu Lys Thr Ile Asn Leu Thr Val Asp Val Pro
```

```
              130                 135                 140
Ile Ser Arg Pro Gln Val Leu Val Ala Ser Thr Thr Val Leu Glu Leu
145                 150                 155                 160

Ser Glu Ala Phe Thr Leu Asn Cys Ser His Glu Asn Gly Thr Lys Pro
                165                 170                 175

Ser Tyr Thr Trp Leu Lys Asp Gly Lys Pro Leu Leu Asn Asp Ser Arg
                180                 185                 190

Met Leu Leu Ser Pro Asp Gln Lys Val Leu Thr Ile Thr Arg Val Leu
            195                 200                 205

Met Glu Asp Asp Leu Tyr Ser Cys Met Val Glu Asn Pro Ile Ser
210                 215                 220

Gln Gly Arg Ser Leu Pro Val Lys Ile Thr Val Tyr Arg Arg Ser Ser
225                 230                 235                 240

Leu Tyr Ile Ile Leu Ser Thr Gly Gly Ile Phe Leu Leu Val Thr Leu
                245                 250                 255

Val Thr Val Cys Ala Cys Trp Lys Pro Ser Lys Arg Lys Gln Lys Lys
                260                 265                 270

Leu Glu Lys Gln Asn Ser Leu Glu Tyr Met Asp Gln Asn Asp Asp Arg
            275                 280                 285

Leu Lys Pro Glu Ala Asp Thr Leu Pro Arg Ser Gly Glu Gln Glu Arg
290                 295                 300

Lys Asn Pro Met Ala Leu Tyr Ile Leu Lys Asp Lys Asp Ser Pro Glu
305                 310                 315                 320

Thr Glu Glu Asn Pro Ala Pro Gly Pro Arg Ser Ala Thr Glu Pro Gly
                325                 330                 335

Pro Pro Gly Tyr Ser Val Ser Pro Ala Val Pro Gly Arg Ser Pro Gly
                340                 345                 350

Leu Pro Ile Arg Ser Ala Arg Arg Tyr Pro Arg Ser Pro Ala Arg Ser
            355                 360                 365

Pro Ala Thr Gly Arg Thr His Ser Ser Pro Pro Arg Ala Pro Ser Ser
370                 375                 380

Pro Gly Arg Ser Arg Ser Ala Ser Arg Thr Leu Arg Thr Ala Gly Val
385                 390                 395                 400

His Ile Ile Arg Glu Gln Asp Glu Ala Gly Pro Val Glu Ile Ser Ala
                405                 410                 415

<210> SEQ ID NO 42
<211> LENGTH: 860
<212> TYPE: DNA
<213> ORGANISM: Homo sapiens

<400> SEQUENCE: 42
acaagtttgt acaaaaaagc aggcttcgcc accatgaaga gagaaagggg agccctgtcc      60
agagcctcca gggccctgcg ccttgctcct tttgtctacc ttcttctgat ccagacagac     120
cccctggagg gggtgaacat caccagcccc gtgcgcctga tccatggcac cgtggggaag     180
tcggctctgc tttctgtgca gtacagcagt accagcagcg acaggcctgt agtgaagtgg     240
cagctgaagc gggacaagcc agtgaccgtg gtgcagtcca ttggcacaga ggtcatcggc     300
accctgcggc ctgactatcg agaccgtatc cgactctttg aaaatggctc cctgcttctc     360
agcgacctgc agctggccga tgagggcacc tatgaggtcg agatctccat caccgacgac     420
accttcactg gggagaagac catcaacctt actgtagatg tgcccatttc gaggccacag     480
accttcactg gggagaagac catcaacctt actgtagatg tgcccatttc gaggccacag     540
```

-continued

```
gtgttggtgg cttcaaccac tgtgctggag ctcagcgagg ccttcacctt gaactgctca    600
catgagaatg gcaccaagcc cagctacacc tggctgaagg atggcaagcc cctcctcaat    660
gactcgagaa tgctcctgtc ccccgaccaa aaggtgctca ccatcacccg cgtgctcatg    720
gaggatgacg acctgtacag ctgcatggtg gagaacccca tcagccaggg ccgcagcctg    780
cctgtcaaga tcaccgtata cagaagaagc tcccaccatc accatcacca ttgaaaccca    840
gctttcttgt acaaagtggt                                                860
```

<210> SEQ ID NO 43
<211> LENGTH: 246
<212> TYPE: PRT
<213> ORGANISM: Homo sapiens

<400> SEQUENCE: 43

```
Met Lys Arg Glu Arg Gly Ala Leu Ser Arg Ala Ser Arg Ala Leu Arg
1               5                   10                  15

Leu Ala Pro Phe Val Tyr Leu Leu Ile Gln Thr Asp Pro Leu Glu
            20                  25                  30

Gly Val Asn Ile Thr Ser Pro Val Arg Leu Ile His Gly Thr Val Gly
            35                  40                  45

Lys Ser Ala Leu Leu Ser Val Gln Tyr Ser Ser Thr Ser Ser Asp Arg
    50                  55                  60

Pro Val Val Lys Trp Gln Leu Lys Arg Asp Lys Pro Val Thr Val Val
65                  70                  75                  80

Gln Ser Ile Gly Thr Glu Val Ile Gly Thr Leu Arg Pro Asp Tyr Arg
                85                  90                  95

Asp Arg Ile Arg Leu Phe Glu Asn Gly Ser Leu Leu Leu Ser Asp Leu
            100                 105                 110

Gln Leu Ala Asp Glu Gly Thr Tyr Glu Val Glu Ile Ser Ile Thr Asp
            115                 120                 125

Asp Thr Phe Thr Gly Glu Lys Thr Ile Asn Leu Thr Val Asp Val Pro
    130                 135                 140

Ile Ser Arg Pro Gln Val Leu Val Ala Ser Thr Thr Val Leu Glu Leu
145                 150                 155                 160

Ser Glu Ala Phe Thr Leu Asn Cys Ser His Glu Asn Gly Thr Lys Pro
                165                 170                 175

Ser Tyr Thr Trp Leu Lys Asp Gly Lys Pro Leu Leu Asn Asp Ser Arg
            180                 185                 190

Met Leu Leu Ser Pro Asp Gln Lys Val Leu Thr Ile Thr Arg Val Leu
            195                 200                 205

Met Glu Asp Asp Asp Leu Tyr Ser Cys Met Val Glu Asn Pro Ile Ser
    210                 215                 220

Gln Gly Arg Ser Leu Pro Val Lys Ile Thr Val Tyr Arg Arg Ser Ser
225                 230                 235                 240

His His His His His His
                245
```

CYTOKINE ANTAGONIST MOLECULES

REFERNCE TO RELATED APPLICATIONS

This application is a continuation-in-part of International Application PCT/GB03/01851 filed on Apr. 30, 2003 designating the U.S., which claims priority from Great Britain Application GB 0209884.6 filed Apr. 30, 2002.

Each of the foregoing applications, and each document cited or referenced in each of the foregoing applications, including during the prosecution of each of the foregoing applications and ("application cited documents"), and any manufacturer's instructions or catalogues for any products cited or mentioned in each of the foregoing applications and articles and in any of the application cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

All publications, patents and patent applications cited herein are incorporated in full by reference.

SUMMARY OF THE INVENTION

This invention relates to novel proteins (termed INSP052 and INSP055), herein identified as immunoglobulin domain-containing cell surface recognition molecules and to the use of these proteins and nucleic acid sequences from the encoding genes in the diagnosis, prevention and treatment of disease, for instance in the diagnosis, prevention and treatment of inflammatory diseases, auto-immune diseases, liver disease or liver failure.

BACKGROUND

The process of drug discovery is presently undergoing a fundamental revolution as the era of functional genomics comes of age. The term "functional genomics" applies to an approach utilising bioinformatics tools to ascribe function to protein sequences of interest. Such tools are becoming increasingly necessary as the speed of generation of sequence data is rapidly outpacing the ability of research laboratories to assign functions to these protein sequences.

As bioinformatics tools increase in potency and in accuracy, these tools are rapidly replacing the conventional techniques of biochemical characterisation. Indeed, the advanced bioinformatics tools used in identifying the present invention are now capable of outputting results in which a high degree of confidence can be placed.

Various institutions and commercial organisations are examining sequence data as they become available and significant discoveries are being made on an on-going basis. However, there remains a continuing need to identify and characterise further genes and the polypeptides that they encode, as targets for research and for drug discovery.

Recently, a remarkable tool for the evaluation of sequences of unknown function has been developed by the Applicant for the present invention. This tool is a database system, termed the Biopendium search database, that is the subject of WO01/69507. This database system consists of an integrated data resource created using proprietary technology and containing information generated from an all-by-all comparison of all available protein or nucleic acid sequences.

The aim behind the integration of these sequence data from separate data resources is to combine as much data as possible, relating both to the sequences themselves and to information relevant to each sequence, into one integrated resource. All the available data relating to each sequence, including data on the three-dimensional structure of the encoded protein, if this is available, are integrated together to make best use of the information that is known about each sequence and thus to allow the most educated predictions to be made from comparisons of these sequences. The annotation that is generated in the database and which accompanies each sequence entry imparts a biologically relevant context to the sequence information.

This data resource has made possible the accurate prediction of protein function from sequence alone. Using conventional technology, this is only possible for proteins that exhibit a high degree of sequence identity (above about 20%-30% identity) to other proteins in the same functional family. Accurate predictions are not possible for proteins that exhibit a very low degree of sequence homology to other related proteins of known function.

Signal Peptide-Containing Proteins

The ability of cells to make and secrete extracellular proteins is central to many biological processes. Enzymes, growth factors, extracellular matrix proteins and signaling molecules are all secreted by cells. This is through fusion of a secretory vesicle with the plasma membrane. In most cases, but not all, proteins are directed to the endoplasmic reticulum and into secretory vesicles by a signal peptide. Signal peptides are cis-acting sequences that affect the transport of polypeptide chains from the cytoplasm to a membrane bound compartment such as a secretory vesicle. Polypeptides that are targeted to the secretory vesicles are either secreted into the extracellular matrix or are retained in the plasma membrane. The polypeptides that are retained in the plasma membrane will have one or more transmembrane domains. Examples of signal peptide containing proteins that play a central role in the functioning of a cell are cytokines, hormones, extracellular matrix proteins, adhesion molecules, receptors, proteases, and growth and differentiation factors.

Immunoglobulin Domain-Containing Cell Surface Recognition Molecules

Immunoglobulin domain-containing cell surface recognition molecules have been shown to play a role in diverse physiological functions, many of which can play a role in disease processes. Alteration of their activity is a means to alter the disease phenotype and as such identification of novel immunoglobulin domain-containing cell surface recognition molecules is highly relevant as they may play a role in many diseases, particularly inflammatory disease, oncology, and cardiovascular disease. Immunoglobulin domain-containing cell surface recognition molecules are involved in a range of biological processes, including: embryogenesis (Martin-Bermudo, M. D. et al, Development. 2000 127(12):2607-15;

Chen, L. M., et al., J. Neurosci. 2000 20(10):3776-84; Zweegman, S., et al, Exp Hematol. 2000 28(4):401-10; Darribere, T., et al., Biol Cell. 2000 92(1):5-25), maintenance of tissue integrity (Eckes, B., et al., J Cell Sci. 2000 113(Pt 13):2455-2462; Buckwalter, J. A., et al., Instr Course Lect. 2000 49:481-9; Frenette, P. S., et al., J Exp Med. 2000 191(8):1413-22; Delmas, V., et al, Dev Biol. 1999 216(2):491-506; Humphries, M. J., et al., Trends Pharmacol Sci. 2000 21(1): 29-32; Miosge, N., et al, Lab Invest. 1999 79(12):1591-9; Nagaoka T, et al. Am J Pathol 2000 July 157:1 237-47; Nwariaku F E, et al. J Trauma 1995 39(2): 285-8; Zhu X, et al. Zhonghua Zheng Xing Shao Shang Wai Ke Za Zhi 1999 15(1): 53-5), leukocyte extravasation/inflammation (Lim, L. H., et al. Am J Respir Cell Mol. Biol. 2000 22(6):693-701; Johnston, B., et al., Microcirculation. 2000 7(2):109-18; Mertens, A. V., et al., Clin Exp Allergy. 1993 23(10):868-73; Chcialowski, A., et al., Pol Merkuriusz Lek. 2000 7(43):13-7; Rojas, A. I., et al, Crit Rev Oral Biol Med. 1999 10(3):337-58; Marinova-Mutafchieva, L., et al., Arthritis Rheum. 2000 43(3):638-44; Vijayan, K. V., et al, J Clin Invest. 2000 105 (6):793-802; Currie, A. J., et al,. J. Immunol. 2000 164(7): 3878-86; Rowin, M. E., et al., Inflammation. 2000 24(2):157-73; Johnston, B., et al., J. Immunol. 2000 164(6):3337-44; Gerst, J. L., et al., J Neurosci Res. 2000 59(5):680-4; Kagawa, T. F., et al., Proc Natl Acad Sci USA. 2000 97(5):2235-40; Hillan, K. J., et al., Liver. 1999 9(6):509-18; Panes, J., 1999 22(10):514-24; Arao, T., et al., J Clin Endocrinol Metab. 2000 85(1):382-9; Souza, H. S., et al., Gut. 1999 45(6):856-63; Grunstein, M. M., et al., Am J Physiol Lung Cell Mol Physiol. 2000 278(6):L1154-63; Mertens, A. V., et al., Clin Exp Allergy. 1993 23(10):868-73; Berends, C., et al., Clin Exp Allergy. 1993 23(11):926-33; Femvik, E., et al., Inflammation. 2000 24(1):73-87; Bocchino, V., et al., J Allergy Clin Immunol. 2000 105(1 Pt 1):65-70; Jones S C, et al, Gut 1995 36(5):724-30; Liu C M, et al, Ann Allergy Asthma Immunol 1998 81(2):176-80; McMurray R W Semin Arthritis Rheum 1996 25(4):215-33; Takahashi H, et al Eur J Immunol 1992 22(11): 2879-85; Carlos T, et al J Heart Lung Transplant 1992 11(6): 1103-8; Fabrega E, et al, Transplantation 2000 69(4): 569-73; Zohrens G, et al, Hepatology 1993 18(4): 798-802; Montefort S, et al. Am J Respir Crit Care Med 1994 149(5): 1149-52), oncogenesis (Orr, F. W., et al., Cancer. 2000 88(S12):2912-2918; Zeller, W., et al., J Hematother Stem Cell Res. 1999 8(5):539-46; Okada, T., et al., Clin Exp Metastasis. 1999 17(7):623-9; Mateo, V., et al., Nat Med. 1999 5(11):1277-84; Yamaguchi, K., et al., J Exp Clin Cancer Res. 2000 19(1):113-20; Maeshima, Y., et al., J Biol. Chem. 2000 275(28):21340-8; Van Waes, C., et al., Int J Oncol. 2000 16(6):1189-95; Damiano, J. S., et al., Leuk Lymphoma. 2000 38(1-2):71-81; Seflor, R. E., et al., Cancer Metastasis Rev. 1999 18(3):359-75; Shaw, L. M., J Mammary Gland Biol Neoplasia. 1999 4(4):367-76; Weyant, M. J., et al., Clin Cancer Res. 2000 6(3):949-56), angiogenesis (Koch A E, et al Nature 1995 376 (6540): 517-9; Wagener C & Ergun S. Exp Cell Res 2000 261(1): 19-24; Ergun S, et al. Mol Cell 2000 5(2): 311-20), bone resorption (Hartman G D, & Duggan M E. Expert Opin Investig Drugs 2000 9(6): 1281-91; Tanaka Y, et al. J Bone Miner Res 1995 10(10): 1462-9; Lark M W, et al. J Pharmacol Exp Ther 1999 291(2): 612-7; Raynal C, et al. Endocrinology 1996 137(6):2347-54; Ilvesaro J M, et al. Exp Cell Res 1998 242(1): 75-83), neurological dysfunction (Ossege L M, et al. Int Immunopharmacol 2001 1:1085-100; Bitsch A, et al, Stroke 1998 29:2129-35; Iadecola C & Alexander M. Curr Opin Neurol 2001 14:89-94; Becker K, et al Stroke 2001 32(1): 206-11; Relton J K, et al Stroke 2001 32(1): 199-205; Hamada Y, et al J Neurochem 1996 66:1525-31), thrombogenesis (Wang, Y. G., et al., J Physiol (Lond). 2000 526(Pt 1):57-68; Matsuno, H., et al., Nippon Yakurigaku Zasshi. 2000 115(3):143-50; Eliceiri, B. P., et al., Cancer J Sci Am. 2000 6(Suppl 3):S245-9; von Beckerath, N., et al., Blood. 2000 95(11):3297-301; Topol, E. J., et al., Am Heart J. 2000 139(6):927-33; Kroll, H., et al., Thromb Haemost. 2000 83(3):392-6), and invasion/adherence of bacterial pathogens to the host cell (Dersch P, et al. EMBO J 1999 18(5): 1199-1213).

The detailed characterisation of the structure and function of several immunoglobulin-domain containing cell surface recognition molecule families has led to active programs by a number of pharmaceutical companies to develop modulators for use in the treatment of diseases involving inflammation, oncology, neurology, immunology and cardiovascular function. Immunoglobulin domain containing cell surface recognition molecules are involved in virtually every aspect of biology from embryogenesis to apoptosis. They are essential to the structural integrity and homeostatic functioning of most tissues. It is therefore not surprising that defects in immunoglobulin domain containing cell surface recognition molecules cause disease and that many diseases involve modulation of immunoglobulin domain containing cell surface recognition molecule function. The members of this family are described below in Table 1.

The Immunoglobulin domain containing cell surface recognition molecule family in fact contains several distinct families. Of these families, some are of particular pharmaceutical interest due to small molecule tractibility. They include:

1. The immunoglobulin adhesion molecules represent the counter receptors for the integrins and includes the intracellular adhesion molecules (ICAMs) and vascular cell adhesion molecules (VCAMs). Members are composed of variable numbers of globular, immunoglobulin-like, extracellular domains. Some members of the family, for example, PECAM-1 (CD31) and NCAM, mediate homotypic adhesion. Some members of the family, for example ICAM-1 and VCAM-1, mediate adhesion via interactions with integrins.

2. Cell surface growth factor receptors. Growth factors are extracellular and in order to exert a biological effect they interact with specific, high affinity receptors located on the plasma membranes of target cells. The molecular characterisation of a variety of different growth factor receptors revealed that they fall into defined families; the tyrosine kinase receptors, G-protein associated seven transmembrane receptors, and the serine/threonine kinase receptors. The tyrosine kinase receptors are characterised by an extracellular domain, a transmembrane domain, and an intracellular domain which possess tyrosine kinase activity. VEGFR, PDGFR, FGFR, CSF-1R and c-KIT are examples of tyrosine kinase growth factor receptors which also contain immunoglobulin domains in the extracellular portion. Dys-regulation of growth factor function results in many different disease phenotypes, including, but not exclusive to oncology (Bartucci M et al, (2001) Cancer Res. September 15;61 (18):6747-54, Dias S et al., (2001) Proc Natl Acad Sci USA. September 11;98(19):10857-62, Djavan B et al., (2001) World J Urol. 19(4):225-33), inflammation (Fiocchi C. (2001) J Clin Invest. August;108(4):523-6, Hodge S et al., (2001) Respirology. September;6(3): 205-211, Fenwick S A et al., (2001) J Anat. September; 199(Pt 3):231-40), neurological (Cooper J D et al., (2001) Proc Natl Acad Sci USA 98(18):10439-44, Fahnestock M et al, (2001) Mol Cell Neurosci 18(2):210-

20), and metabolism (Vickers M H et al., (2001) Endocrinology. 142(9):3964-73).

TABLE 1

Immunoglubulin domain-containing cell surface recognition molecules

| Receptor | Ligand | Distribution |
| --- | --- | --- |
| ICAM-1<br>5 Ig domains | LFA-1 (CD11a/CD18)<br>Mac-1 (CD11b/CD18),<br>CD43 | Widespread, endothelial cells, fibroblasts,<br>epithelium, monocytes, lymphocytes, dendritic<br>cells, chondrocytes. |
| ICAM-2<br>2 Ig domains | LFA-1 (CD11b) | endothelial cells (high): lymphocytes, monocytes,<br>basophils, platelets (low). |
| ICAM-3<br>5 Ig domains | LFA-1 ($\alpha$d/CD 18) | Lymphocytes, monocytes, neutrophils, eosinophils,<br>basophils. |
| VCAM-1<br>6 or 7 Ig<br>domains | $\alpha 4\beta 1$, $\alpha 4\beta 7$ | Endothelial cells, monocytes, fibroblasts, dendritic<br>cells, bone marrow stromal cells, myoblasts. |
| LFA-3<br>6 Ig domains | CD2 | Endothelial cells, leukocytes, epithelial cells |
| PECAM-1<br>(CD31) | CD31, heparin | Endothelial cells (at EC-EC junctions), T cell<br>subsets, platelets, neutrophils, eosinophils,<br>monocytes, smooth muscle cells, bone marrow<br>stem cells. |
| NCAM | NCAM, heparin $SO_4$ | Neural cells, muscle |
| MAdCAM-1<br>4 Ig domains | $\alpha 4\beta 7$, L-selectin | Peyer's patch, mesenteric lymph nodes, mucosal<br>endothelial cells, spleen. |
| CD2 | CD58, CD59, CD48 | T lymphocytes |
| VEGFR | VEGF | Widespread, retina, umbilical vein, adrenal, NT2<br>neuronal precursor cells |
| FGFR | FGF | Widespread, brain, colon, ovary |
| KIT | Stem Cell Factor, MGF | Widespread, foetus, melanocytes, gall bladder,<br>cerebellum, gastric epithelium (low) |
| PDGFR | PDGF | Widespread, breast, placenta, fibroblast, lung,<br>ovary, skin, heart |
| CSF-1R | CSF | Widespread, placenta, liver, multiple sclerosis<br>lesions, spleen, lung, breast. |

Immunoglobulin domain-containing cell surface recognition molecules have thus been shown to play a role in diverse physiological functions, many of which can play a role in disease processes. Alteration of their activity is a means to alter the disease phenotype and as such identification of novel Immunoglobulin domain-containing cell surface recognition molecules is highly relevant as they may play a role in many diseases, particularly immunology, inflammatory disease, oncology, cardiovascular disease, central nervous system disorders and infection.

THE INVENTION

The invention is based on the discovery that the INSP052 and INSP055 proteins function as immunoglobulin domain-containing cell surface recognition molecules. Examples of immunoglobulin domain-containing cell surface recognition molecules are listed in Table 1.

In one embodiment of the first aspect of the invention, there is provided a polypeptide which:
  (i) comprises or consists of the amino acid sequence as recited in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:20, SEQ ID NO:22, SEQ ID NO:24, or SEQ ID NO:26;
  (ii) is a fragment thereof having the activity of a polypeptide according to (i), or having an antigenic determinant in common with a polypeptide according to (i); or
  (iii) is a functional equivalent of (i) or (ii).

By "the activity of a polypeptide according to (i)", we refer to immunoglobulin domain-containing cell surface recognition molecule activity. By immunoglobulin domain-containing cell surface recognition molecule activity we refer to polypeptides that comprise amino acid sequence or structural features that can be identified as conserved features within the immunoglobulin domain-containing cell surface recognition molecule family. Included within this definition is activity as a cytokine antagonist, particularly as an antagonist of cytokine expression and/or secretion, particularly with respect to TNF-alpha, IL-4 and/or IL-2.

Evidence is presented in the Examples section below that the extracellular domain of INSP052 (also referred to herein as INSP052EC) downregulates TNF-alpha, IL-4 and IL-2 secretion in vitro in a Concanavalin A (ConA) stimulated human peripheral blood mononuclear cells (hPBMC) assay. In addition, delivery of INSP052EC cDNA in an in vivo model of fulminant hepatitis was found to decrease TNF-alpha and m-IL-6 levels in serum and had a significant effect on the reduction of transaminases measured in serum. This effect was confirmed by subcutaneous INSP052EC protein injections.

The decrease in aspartate aminotransferase (ASAT) and alanine aminotransferase (ALAT) levels noted might be due to both decreased TNF-alpha and IL-4 levels. TNF-alpha and IL-4 are important cytokines involved in liver damage induced after ConA injection. In this mouse model of liver hepatitis, TNF-alpha is mainly produced by hepatic macrophages, the so-called Kupfer cells, whereas IL-4 is produced by liver (natural killer T) NKT cells. Anti TNF-alpha antibodies have been shown to confer protection against disease (Seino et al. 2001, Annals of surgery 234, 681) and inhibition of IL-4 production by NKT cells was shown to be hepato-protective in T-cell mediated hepatitis in mouse (Ajuebor et al. 2003 J. Immunology 170, 5252-9). Accordingly, it is considered that INSP052, INSP052EC (SEQ ID NO.20 and SEQ ID NO.22) and related functionally equivalent proteins will be useful in treating auto-immune, viral or acute liver diseases as well as alcoholic liver failures. They are likely also to be effective in treating other inflammatory diseases.

The polypeptide having the sequence recited in SEQ ID NO:2 is referred to hereafter as "the INSP052 exon 1 polypeptide". The polypeptide having the sequence recited in SEQ ID NO:4 is referred to hereafter as "the INSP052 exon 2 polypeptide". The polypeptide having the sequence recited in SEQ ID NO:6 is referred to hereafter as "the INSP052 exon 3 polypeptide". The polypeptide having the sequence recited in SEQ ID NO:8 is referred to hereafter as "the INSP052 exon 4 polypeptide". The polypeptide having the sequence recited in SEQ ID NO:10 is referred to hereafter as "the INSP052 exon 5 polypeptide". The polypeptide having the sequence recited in SEQ ID NO:12 is referred to hereafter as "the INSP052 exon 6 polypeptide". The polypeptide having the sequence recited in SEQ ID NO:14 is referred to hereafter as "the INSP052 exon 7 polypeptide". Combining SEQ ID NO:2, SEQ ID NO:4, SEQ ID NO:6, SEQ ID NO:8, SEQ ID NO:10, SEQ ID NO:12 and SEQ ID NO:14 produces the sequence recited in SEQ ID NO:16. The polypeptide having the sequence recited in SEQ ID NO:16 is referred to hereafter as the INSP052 polypeptide. The polypeptide having the sequence recited in SEQ ID NO:20 is the extracellular domain of INSP052. The polypeptide having the sequence recited in SEQ ID NO:22 is referred to hereafter as the extracellular domain of the mature INSP052 polypeptide. The polypeptide having the sequence recited in SEQ ID NO:24 is referred to hereafter as the mature INSP052 exon 2 polypeptide. The polypeptide having the sequence recited in SEQ ID NO:26 is referred to hereafter as the mature INSP052 polypeptide.

The term "INSP052 exon polypeptides" as used herein includes polypeptides comprising or consisting of the polypeptide sequences set forth herein, including the INSP052 exon 1 polypeptide, the INSP052 exon 2 polypeptide, the INSP052 exon 3 polypeptide, the INSP052 exon 4 polypeptide, the INSP052 exon 5 polypeptide, the INSP052 exon 6 polypeptide, the INSP052 exon 7 polypeptide, the INSP052 polypeptide, the extracellular domain of INSP052, the extracellular domain of mature INSP052, the INSP052 mature exon 2 polypeptide, and the mature INSP052 polypeptide.

In one embodiment, the polypeptide according to this embodiment consists of the amino acid sequence recited in SEQ ID NO:16 or is a fragment of or functional equivalent thereof. In another embodiment, the polypeptide consists of the amino acid sequence recited in SEQ ID NO:2, SEQ ID NO:4, SEQ ID NO:6, SEQ ID NO:8, SEQ ID NO:10, SEQ ID NO:12, or SEQ ID NO:14, or a variant thereof.

In a further embodiment of the first aspect of the invention there is provided a polypeptide which:
  i) comprises or consists of the amino acid sequence as recited in SEQ ID NO:20 or SEQ ID NO:22;
  ii) is a fragment thereof having the activity of a polypeptide according to (i), or having an antigenic determinant in common with a polypeptide according to (i); or
  iii) is a functional equivalent of (i) or (ii).

The amino acid sequence recited in SEQ ID NO:20 represents the extracellular domain of INSP052 and corresponds to amino acids 1-240 of the full length protein (see the Examples section). SEQ ID NO:22 represents the extracellular domain of mature INSP052. See also FIG. 7 for the extracellular domain of INSP052.

It is considered highly likely that the extracellular domain will fold correctly and show biological activity if additional residues C terminal and/or N terminal of these boundaries in the polypeptide sequence are included in the polypeptide fragment. For example, an additional 5, 10, 20, 30, 40, 50 or even 100 amino acid residues from the INSP052 polypeptide sequence, or from a homologous sequence, may be included at either or both the C terminal and/or N terminal of the boundaries of the receptor binding domain, without prejudicing the ability of the polypeptide fragment to fold correctly and exhibit biological activity. Extensions as large as 100 or 200 residues may be necessary due to the presence of large loops between secondary structural elements.

For truncated variants of the INSP052 extracellular domain, one or a few amino acid residues (for example, 2, 3, 4, 5, 10, 15, 20, 25, 30 or more) may be deleted at either or both the C terminus or the N terminus of the domain without prejudicing biological activity.

As discussed below, the polypeptides of the invention may be provided in the form of a fusion protein or as "free-standing" protein. Accordingly, one embodiment of the invention provides a polypeptide which consists of the extracellular domain of INSP052. Another embodiment of the invention provides a polypeptide which consists of INSP052 (the full length protein or the extracellular domain thereof, including the mature versions thereof) fused with at least one other polypeptide to form a fusion protein.

In a second embodiment of the first aspect of the invention, there is provided a polypeptide which:
  (i) comprises or consists of the amino acid sequence as recited in SEQ ID NO: 18,
  (ii) is a fragment thereof having the activity of a polypeptide of (i), or having an antigenic determinant in common with a polypeptide of (i); or
  (iii) is a functional equivalent of (i) or (ii).

By "the activity of a polypeptide according to (i)", we refer to immunoglobulin domain-containing cell surface recognition molecule activity.

Preferably, the polypeptide according to this embodiment consists of the amino acid sequence recited in SEQ ID NO:18 or is a fragment of or functional equivalent thereof.

The polypeptide having the sequence recited in SEQ ID NO:18 is referred to hereafter as "the INSP055 polypeptide".

In a second aspect, the invention provides a purified nucleic acid molecule which encodes a polypeptide of the first aspect of the invention.

Preferably, the purified nucleic acid molecule comprises or consists of the nucleic acid sequence as recited in SEQ ID NO:1 (encoding the INSP052 exon 1 polypeptide), SEQ ID NO:3 (encoding the INSP052 exon 2 polypeptide), SEQ ID NO:5 (encoding the INSP052 exon 3 polypeptide), SEQ ID NO:7 (encoding the INSP052 exon 4 polypeptide), SEQ ID NO:9 (encoding the INSP052 exon 5 polypeptide), SEQ ID NO:11 (encoding the INSP052 exon 6 polypeptide), SEQ ID NO:13 (encoding the INSP052 exon 7 polypeptide), SEQ ID NO:15 (encoding the INSP052 polypeptide), SEQ ID NO:17 (encoding the INSP055 polypeptide), SEQ ID NO:20 (encoding the extracellular domain of the INSP052 polypeptide), SEQ ID NO:22 (encoding the extracellular domain of the INSP052 mature polypeptide), SEQ ID NO:24 (encoding the mature INSP052 exon 2 polypeptide), SEQ ID NO:26 (encoding the mature INSP052 polypeptide) or is a redundant equivalent or fragment of any one of these sequences.

Combining the sequences recited in SEQ ID NO:1, SEQ ID NO:3, SEQ ID NO:5, SEQ ID NO:7, SEQ ID NO:9, SEQ ID NO:11 and SEQ ID NO:13 produces the sequence recited in SEQ ID NO:15.

Combining the sequences recited in SEQ ID NO:23, SEQ ID NO:5, SEQ ID NO:7, SEQ ID NO:9, SEQ ID NO:11 and SEQ ID NO:13 produces the sequence recited in SEQ ID NO:25.

In one embodiment of the second aspect of the invention there is provided a nucleic acid molecule which encodes a polypeptide which comprises or consists of the extracellular domain of INSP052 (SEQ ID NO:20). Preferably, the nucleic acid molecule comprises or consists of the nucleic acid sequence set forth in SEQ ID NO:19. This is also set out in FIG. 7, although these sequences include histidine residues added to the C terminal.

In one embodiment of the second aspect of the invention there is provided a nucleic acid molecule which encodes a polypeptide which comprises or consists of the extracellular domain of mature INSP052 (SEQ ID NO:22). Preferably, the nucleic acid molecule comprises or consists of the nucleic acid sequence set forth in SEQ ID NO:21. This is also set out in FIG. 7, although these sequences include histidine residues added to the C terminal.

In a third aspect, the invention provides a purified nucleic acid molecule which hybridizes under high stringency conditions with a nucleic acid molecule of the second aspect of the invention.

In a fourth aspect, the invention provides a vector, such as an expression vector, that contains a nucleic acid molecule of the second or third aspect of the invention.

In a fifth aspect, the invention provides a host cell transformed with a vector of the fourth aspect of the invention.

In a sixth aspect, the invention provides a ligand which binds specifically to, and which preferably inhibits the activity of a polypeptide of the first aspect of the invention.

By "the activity of a polypeptide of the invention" and similar expressions, we refer to activity characteristic of immunoglobulin domain-containing cell surface recognition molecules. In particular, included within this definition is activity as a cytokine antagonist, particularly as an antagonist of cytokine expression and/or secretion, particularly with respect to TNF-alpha, IL-4 and IL-2.

In a seventh aspect, the invention provides a compound that is effective to alter the expression of a natural gene which encodes a polypeptide of the first aspect of the invention or to regulate the activity of a polypeptide of the first aspect of the invention.

A compound of the seventh aspect of the invention may either increase (agonise) or decrease (antagonise) the level of expression of the gene or the activity of the polypeptide.

Importantly, the identification of the function of the INSP052 and INSP055 polypeptides allows for the design of screening methods capable of identifying compounds that are effective in the treatment and/or diagnosis of disease. Ligands and compounds according to the sixth and seventh aspects of the invention may be identified using such methods. These methods are included as aspects of the present invention.

Evidence is presented in the Examples section below that the extracellular domain of INSP052 may be used to prevent or treat inflammatory diseases, auto-immune diseases, liver disease or liver failure. Accordingly, the provision of a compound according to the seventh aspect of the invention which mimics extracellular domain of INSP052 conformationally, or is an agonist of the extracellular domain of INSP052 is particularly preferred since such a compound may find utility in the prevention or treatment of an inflammatory disease, an auto-immune disease, liver disease or liver failure as described above.

In an eighth aspect, the invention provides a polypeptide of the first aspect of the invention, or a nucleic acid molecule of the second or third aspect of the invention, or a vector of the fourth aspect of the invention, or a host cell of the fifth aspect, or a ligand of the sixth aspect of the invention, or a compound of the seventh aspect of the invention, for use in therapy or diagnosis, preferably in relation to inflammatory diseases, auto-immune diseases, liver disease (including viral or acute liver disease) and liver failure (including alcoholic liver failure).

The moieties of the first, second, third, fourth, fifth and sixth aspects of the invention may also be used in the manufacture of a medicament for the prevention or treatment of diseases including, but not limited to, cell proliferative disorders, autoimmune/inflammatory disorders, cardiovascular disorders, neurological and psychiatric disorders, developmental disorders, genetic disorders, metabolic disorders, infections and other pathological conditions.

These diseases preferably include neoplasm, cancer, brain tumour, glioma, bone tumor, lung tumor, breast tumour, prostate tumour, colon tumour, hemangioma, myeloproliferative disorder, leukemia, hematological disease, neutropenia, thrombocytopenia, angiogenesis disorders, dermatological disease, ageing, wounds, burns, fibrosis, cardiovascular disease, restensosis, heart disease, peripheral vascular disease, coronary artery disease, oedema, thromboembolism, dysmenorrhea, endometriosis, pre-eclampsia, lung disease, COPD, asthma bone disease, renal disease, glomerulonephritis, liver disease, Crohn's disease, gastritis, ulcerative colitis, ulcer, immune disorder, autoimmune disease, arthritis, rheumatoid arthritis, psoriasis, epidermolysis bullosa, systemic lupus erythematosus, ankylosing spondylitis, Lyme disease, multiple sclerosis, neurodegeneration, stroke, brain/spinal cord injury, Alzheimer's disease, Parkinson's disease, motor neurone disease, neuromuscular disease, HIV, AIDS, cytomegalovirus infection, fungal infection, ocular disorder, macular degeneration, glaucoma, diabetic retinopathy, ocular hypertension and other conditions in which immunoglobulin domain containing cell surface recognition molecules are implicated.

It is particularly preferred that the moieties of the first, second, third, fourth, fifth and sixth aspects of the invention are used in the manufacture of a medicament for the treatment of inflammatory diseases, auto-immune diseases, liver disease (including viral or acute liver disease) and liver failure (including alcoholic liver failure).

In a ninth aspect, the invention provides a method of diagnosing a disease in a patient, comprising assessing the level of expression of a natural gene encoding a polypeptide of the first aspect of the invention or the activity of a polypeptide of the first aspect of the invention in tissue from said patient and comparing said level of expression or activity to a control level, wherein a level that is different to said control level is indicative of disease. Such a method will preferably be carried out in vitro.

Similar methods may be used for monitoring the therapeutic treatment of disease in a patient, wherein altering the level of expression or activity of a polypeptide or nucleic acid molecule over the period of time towards a control level is indicative of regression of disease.

A preferred method for detecting polypeptides of the first aspect of the invention comprises the steps of: (a) contacting a ligand, such as an antibody, of the sixth aspect of the invention with a biological sample under conditions suitable for the formation of a ligand-polypeptide complex; and (b) detecting said complex.

A number of different methods according to the ninth aspect of the invention exist, as the skilled reader will be aware, such as methods of nucleic acid hybridization with short probes, point mutation analysis, polymerase chain reaction (PCR) amplification and methods using antibodies to detect aberrant protein levels. Similar methods may be used on a short or long term basis to allow therapeutic treatment of a disease to be monitored in a patient. The invention also provides kits that are useful in these methods for diagnosing disease.

Preferably, the disease diagnosed by a method of the ninth aspect of the invention is a disease in which immunoglobulin domain-containing cell surface recognition molecules are implicated, as described above.

A preferred disease diagnosed by a method of the ninth aspect of the invention is an inflammatory disease, auto-immune disease, liver disease (including viral or acute liver disease) or liver failure (including alcoholic liver failure).

In a tenth aspect, the invention provides for the use of the polypeptides of the first aspect of the invention as immunoglobulin domain-containing cell surface recognition molecules. The importance of the Ig domain in cell surface receptors is described in Lokker N A et al., "Functional importance of platelet-derived growth factor (PDGF) receptor extracellular immunoglobulin-like domains. Identification of PDGF binding site and neutralizing monoclonal antibodies," *J Biol Chem* 1997 December. 26;272(52):33037-44.

The invention also provides for the use of a nucleic acid molecule according to the second or third aspects of the invention to express a protein that possesses immunoglobulin domain-containing cell surface recognition molecule activity. The invention also provides a method for effecting immunoglobulin domain-containing cell surface recognition molecule activity, said method utilising a polypeptide of the first aspect of the invention.

In an eleventh aspect, the invention provides a pharmaceutical composition comprising a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, in conjunction with a pharmaceutically-acceptable carrier.

In a twelfth aspect, the present invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in therapy or diagnosis. These molecules may also be used in the manufacture of a medicament for the treatment of diseases including, but not limited to, cell proliferative disorders, autoimmune/inflammatory disorders, cardiovascular disorders, neurological and psychiatric disorders, developmental disorders, genetic disorders, metabolic disorders, infections and other pathological conditions. These diseases preferably include neoplasm, cancer, brain tumour, glioma, bone tumor, lung tumor, breast tumour, prostate tumour, colon tumour, hemangioma, myeloproliferative disorder, leukemia, hematological disease, neutropenia, thrombocytopenia, angiogenesis disorders, dermatological disease, ageing, wounds, burns, fibrosis, cardiovascular disease, restensosis, heart disease, peripheral vascular disease, coronary artery disease, oedema, thromboembolism, dysmenorrhea, endometriosis, pre-eclampsia, lung disease, COPD, asthma bone disease, renal disease, glomerulonephritis, liver disease, Crohn's disease, gastritis, ulcerative colitis, ulcer, immune disorder, autoimmune disease, arthritis, rheumatoid arthritis, psoriasis, epidermolysis bullosa, systemic lupus erythematosus, ankylosing spondylitis, Lyme disease, multiple sclerosis, neurodegeneration, stroke, brain/spinal cord injury, Alzheimer's disease, Parkinson's disease, motor neurone disease, neuromuscular disease, HIV, AIDS, cytomegalovirus infection, fungal infection, ocular disorder, macular degeneration, glaucoma, diabetic retinopathy, ocular hypertension and other conditions in which immunoglobulin domain containing cell recognition molecules are implicated.

It is particularly preferred that the moieties of the first, second, third, fourth, fifth and sixth aspects of the invention are used in the manufacture of a medicament for the treatment of an inflammatory disease, an auto-immune disease, liver disease or liver failure.

In a thirteenth aspect, the invention provides a method of treating a disease in a patient comprising administering to the patient a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention.

For diseases in which the expression of a natural gene encoding a polypeptide of the first aspect of the invention, or in which the activity of a polypeptide of the first aspect of the invention, is lower in a diseased patient when compared to the level of expression or activity in a healthy patient, the polypeptide, nucleic acid molecule, ligand or compound administered to the patient should be an agonist. Conversely, for diseases in which the expression of the natural gene or activity of the polypeptide is higher in a diseased patient when compared to the level of expression or activity in a healthy patient, the polypeptide, nucleic acid molecule, ligand or compound administered to the patient should be an antagonist. Examples of such antagonists include antisense nucleic acid molecules, ribozymes and ligands, such as antibodies.

Preferably, the disease is a disease in which immunoglobulin domain-containing cell surface recognition molecules are implicated, as described above.

It is particularly preferred that the disease is an inflammatory disease, an auto-immune disease, liver disease or liver failure.

In a fourteenth aspect, the invention provides transgenic or knockout non-human animals that have been transformed to express higher, lower or absent levels of a polypeptide of the first aspect of the invention. Such transgenic animals are very useful models for the study of disease and may also be used in screening regimes for the identification of compounds that are effective in the treatment or diagnosis of such a disease.

Preferably, the disease is a disease in which immunoglobulin domain-containing cell surface recognition molecules are implicated, as described above.

It is particularly preferred that the disease is an inflammatory disease, an auto-immune disease, liver disease or liver failure.

It should be appreciated that the scope of protection sought for the polypeptides and nucleic acids of the present invention does not extend to nucleic acids or polypeptides present in their natural source. Rather, the polypeptides and nucleic acids claimed by the present invention may be regarded as being "isolated" or "purified". The terms "isolated" and "purified" as used herein refer to a nucleic acid or polypeptide separated from at least one other component (e.g., nucleic acid or polypeptide) present with the nucleic acid or polypeptide in its natural source. Thus, for example, a polypeptide contained in a tissue extract would constitute an "isolated" or "purified" polypeptide, as would a polypeptide synthetically or recombinantly produced. In one embodiment, the nucleic acid or polypeptide is found in the presence of (if anything) only a solvent, buffer, ion, or other component normally present in a solution of the same.

It should be noted that the terms "isolated" and "purified" do not denote the method by which the polypeptide or nucleic acid is obtained or the level of purity of the preparation. Thus, such isolated or purified species may be produced recombinantly, isolated directly from the cell or tissue of interest or produced synthetically based on the determined sequences.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of those working in the art.

Such techniques are explained fully in the literature. Examples of particularly suitable texts for consultation include the following: Sambrook Molecular Cloning; A Laboratory Manual, Second Edition (1989); DNA Cloning, Volumes I and II (D. N Glover ed: 1985); Oligonucleotide Synthesis (M. J. Gait ed. 1984); Nucleic Acid Hybridization (B. D. Hames & S. J. Higgins eds. 1984); Transcription and Translation (B. D. Hames & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D. M. Weir and C. C. Blackwell eds. 1986).

As used herein, the term "polypeptide" includes any peptide or protein comprising two or more amino acids joined to each other by peptide bonds or modified peptide bonds, i.e. peptide isosteres. This term refers both to short chains (peptides and oligopeptides) and to longer chains (proteins).

The polypeptide of the present invention may be in the form of a mature protein or may be a pre-, pro- or preproprotein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence.

The polypeptide of the first aspect of the invention may form part of a fusion protein. For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature polypeptide may be fused with another compound, such as a compound to increase the half-life of the polypeptide (for example, polyethylene glycol).

Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include isolated naturally-occurring polypeptides (for example purified from cell culture), recombinantly-produced polypeptides (including fusion proteins), synthetically-produced polypeptides or polypeptides that are produced by a combination of these methods.

The functionally-equivalent polypeptides of the first aspect of the invention may be polypeptides that are homologous to the INSP052 and INSP055 polypeptides, preferably the INSP052 extracellular domain (i.e. SEQ ID NO:20 or SEQ ID NO:22). Two polypeptides are said to be "homologous", as the term is used herein, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Additionally, homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The terms "variant" or "derivative" in relation to the amino acid sequences of the present invention includes any substitution of, variation of, modification of, replacement of, deletion of or addition of one (or more) amino acids from or to the sequence.

Homologous polypeptides therefore include natural biological variants (for example, allelic variants or geographical variations within the species from which the polypeptides are derived) and mutants (such as mutants containing amino acid substitutions, insertions or deletions) of the INSP052 and INSP055 polypeptides, preferably of the INSP052 extracellular domain. Such mutants may include polypeptides in which one or more of the amino acid residues are substituted with a conserved or non-conserved amino acid residue (preferably a conserved amino acid residue) and such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions. Such mutants also include polypeptides in which one or more of the amino acid residues includes a substituent group.

Typically, greater than 30% identity between two polypeptides is considered to be an indication of functional equivalence. Preferably, functionally equivalent polypeptides of the first aspect of the invention have a degree of sequence identity with the INSP052 and INSP055 polypeptides, or with active fragments thereof, of greater than 80%. More preferred polypeptides have degrees of identity of greater than 85%, 90%, 95%, 98% or 99%, respectively.

The functionally-equivalent polypeptides of the first aspect of the invention may also be polypeptides which have been identified using one or more techniques of structural alignment. For example, the Inpharmatica Genome Threader™ technology that forms one aspect of the search tools used to generate the Biopendium search database may be used (see co-pending International Patent Application No. PCT/GB01/01105, published as WO 01/69507) to identify polypeptides of presently-unknown function which, while having low sequence identity as compared to the INSP052 and INSP055 polypeptides, are predicted to be immunoglobulin domain-containing cell surface recognition molecules, said method utilising a polypeptide of the first aspect of the invention, by virtue of sharing significant structural homology with the INSP052 and INSP055 polypeptide sequences. By "significant structural homology" is meant that the Inpharmatica Genome Threader™ predicts two proteins to share structural homology with a certainty of at least 10% and more preferably, at least 20%, 30%, 40%, 50%, 60%, 70%, 80%, 90% and above.

The polypeptides of the first aspect of the invention also include fragments of the INSP052 and INSP055 polypeptides and fragments of the functional equivalents of the INSP052 and INSP055 polypeptides, provided that those fragments retain immunoglobulin domain-containing cell surface recognition molecule activity or have an antigenic determinant in common with the INSP052 and INSP055 polypeptides.

As used herein, the term "fragment" refers to a polypeptide having an amino acid sequence that is the same as part, but not all, of the amino acid sequence of the INSP052 and INSP055 polypeptides or one of its functional equivalents. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

Such fragments may be "free-standing", i.e. not part of or fused to other amino acids or polypeptides, or they may be comprised within a larger polypeptide of which they form a part or region. When comprised within a larger polypeptide, the fragment of the invention most preferably forms a single continuous region. For instance, certain preferred embodiments relate to a fragment having a pre- and/or pro-polypeptide region fused to the amino terminus of the fragment and/or an additional region fused to the carboxyl terminus of the fragment. However, several fragments may be comprised within a single larger polypeptide.

The polypeptides of the present invention or their immunogenic fragments (comprising at least one antigenic determinant) can be used to generate ligands, such as polyclonal or monoclonal antibodies, that are immunospecific for the polypeptides. Such antibodies may be employed to isolate or to identify clones expressing the polypeptides of the invention or to purify the polypeptides by affinity chromatography. The antibodies may also be employed as diagnostic or therapeutic aids, amongst other applications, as will be apparent to the skilled reader.

The term "immunospecific" means that the antibodies have substantially greater affinity for the polypeptides of the invention than their affinity for other related polypeptides in the prior art. As used herein, the term "antibody" refers to intact molecules as well as to fragments thereof, such as Fab, F(ab')2 and Fv, which are capable of binding to the antigenic determinant in question. Such antibodies thus bind to the polypeptides of the first aspect of the invention.

By "substantially greater affinity" we mean that there is a measurable increase in the affinity for a polypeptide of the invention as compared with the affinity for known immunoglobluin domain-containing cell surface recognition molecules.

Preferably, the affinity is at least 1.5-fold, 2-fold, 5-fold 10-fold, 100-fold, $10^3$-fold, $10^4$-fold, $10^5$-fold or $10^6$-fold greater for a polypeptide of the invention than for known immunogloblu in domain-containing cell surface recognition molecules.

If polyclonal antibodies are desired, a selected mammal, such as a mouse, rabbit, goat or horse, may be immunised with a polypeptide of the first aspect of the invention. The polypeptide used to immunise the animal can be derived by recombinant DNA technology or can be synthesized chemically. If desired, the polypeptide can be conjugated to a carrier protein. Commonly used carriers to which the polypeptides may be chemically coupled include bovine serum albumin, thyroglobulin and keyhole limpet haemocyanin. The coupled polypeptide is then used to immunise the animal. Serum from the immunised animal is collected and treated according to known procedures, for example by immunoaffinity chromatography.

Monoclonal antibodies to the polypeptides of the first aspect of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R. Liss, Inc. (1985).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321, 522 (1986); Verhoeyen et al., Science, 239, 1534 (1988); Kabat et al., J. Immunol., 147, 1709 (1991); Queen et al., Proc. Natl. Acad. Sci. USA, 86, 10029 (1989); Gorman et al., Proc. Natl. Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Preferred nucleic acid molecules of the second and third aspects of the invention are those which encode the polypeptide sequences recited in SEQ ID NO:2, SEQ ID NO:4, SEQ ID NO:6, SEQ ID NO:8, SEQ ID NO:10, SEQ ID NO:12, SEQ ID NO:14 and/or SEQ ID NO:16, SEQ ID NO:18, the extracellular domain of INSP052 (SEQ ID NO:20 and SEQ ID NO:22), SEQ ID NO:24, or SEQ ID NO:26 and functionally equivalent polypeptides, e.g. fusion proteins consisting of the extracellular domain of INSP052 fused to one or more additional polypeptide sequences. These nucleic acid molecules may be used in the methods and applications described herein. The nucleic acid molecules of the invention preferably comprise at least n consecutive nucleotides from the sequences disclosed herein where, depending on the particular sequence, n is 10 or more (for example, 12, 14, 15, 18, 20, 25, 30, 35, 40 or more).

The nucleic acid molecules of the invention also include sequences that are complementary to nucleic acid molecules described above (for example, for antisense or probing purposes).

Nucleic acid molecules of the present invention may be in the form of RNA, such as mRNA, or in the form of DNA, including, for instance cDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphoramidite chemical synthesis, from genomic or cDNA libraries or by separation from an organism. RNA molecules may generally be generated by the in vitro or in vivo transcription of DNA sequences.

The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such as those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation (Nielsen, P. E. et al. (1993) Anticancer Drug Des. 8:53-63).

These molecules also may have a different sequence which, as a result of the degeneracy of the genetic code, encode a polypeptide of SEQ ID NO:2, SEQ ID NO:4, SEQ ID NO:6, SEQ ID NO:8, SEQ ID NO:10, SEQ ID NO:12, SEQ ID NO:14 and/or SEQ ID NO:16, or SEQ ID NO:18, or the extracellular domain of INSP052 or SEQ ID NO:24 or SEQ ID NO:26. Such molecules may include, but are not limited to, the coding sequence for the mature polypeptide by itself; the coding sequence for the mature polypeptide and additional coding sequences, such as those encoding a leader or secretory sequence, such as a pro-, pre- or prepro-polypeptide sequence; the coding sequence of the mature polypeptide, with or without the aforementioned additional coding sequences, together with further additional, non-coding sequences, including non-coding 5' and 3' sequences, such as the transcribed, non-translated sequences that play a role in transcription (including termination signals), ribosome binding and mRNA stability. The nucleic acid molecules may also include additional sequences which encode additional amino acids, such as those which provide additional functionalities.

The nucleic acid molecules of the second and third aspects of the invention may also encode the fragments or the functional equivalents of the polypeptides and fragments of the first aspect of the invention. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide).

DNA shuffling by random fragmentation and PCR reassembly of gene fragments and synthetic oligonucleotides are included as techniques which may be used to engineer the nucleotide sequences. Site-directed mutagenesis may be used to insert new restriction sites, alter glycosylation patterns, change codon preference, produce splice variants, introduce mutations and so forth.

Nucleic acid molecules which encode a polypeptide of the first aspect of the invention may be ligated to a heterologous sequence so that the combined nucleic acid molecule encodes a fusion protein. Such combined nucleic acid molecules are included within the second or third aspects of the invention. For example, to screen peptide libraries for inhibitors of the activity of the polypeptide, it may be useful to express, using such a combined nucleic acid molecule, a fusion protein that can be recognised by a commercially-available antibody. A fusion protein may also be engineered to contain a cleavage site located between the sequence of the polypeptide of the invention and the sequence of a heterologous protein so that the polypeptide may be cleaved and purified away from the heterologous protein.

The nucleic acid molecules of the invention also include antisense molecules that are partially complementary to nucleic acid molecules encoding polypeptides of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991).

The term "hybridization" as used herein refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. [supra]).

The inhibition of hybridization of a completely complementary molecule to a target molecule may be examined using a hybridization assay, as known in the art (see, for example, Sambrook et al [supra]). A substantially homologous molecule will then compete for and inhibit the binding of a completely homologous molecule to the target molecule under various conditions of stringency, as taught in Wahl, G. M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC (150 mM NaCl, 15 mM trisodium citrate), 50 mM sodium phosphate (pH7.6), 5× Denhardts solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. (see Sambrook et al. [supra]). Preferably, the conditions used for hybridization are those of high stringency.

Preferred embodiments of this aspect of the invention are nucleic acid molecules that are at least 70% identical over their entire length to a nucleic acid molecule encoding the INSP052 or INSP055 polypeptides (SEQ ID NO:1, SEQ ID NO:3, SEQ ID NO:5, SEQ ID NO:7, SEQ ID NO:9, SEQ ID NO:11, SEQ ID NO:13 and/or SEQ ID NO:15, or SEQ ID NO:17, or the nucleic acid sequence set forth in FIG. 7 or the coding portion of the nucleic acid sequence set forth in FIG. 7 (i.e. SEQ ID NO:19 or SEQ ID NO:21), SEQ ID NO:23, or SEQ ID NO:25) and nucleic acid molecules that are substantially complementary to such nucleic acid molecules. Preferably, a nucleic acid molecule according to this aspect of the invention comprises a region that is at least 80% identical over its entire length to the coding sequence for SEQ ID NO:2 given in SEQ ID NO:1, the coding sequence for SEQ ID NO:4 given in SEQ ID NO:3, the coding sequences for SEQ ID NO:6 given in SEQ ID NO:5, the coding sequence for SEQ ID NO:8 given in SEQ ID NO:7, the coding sequence for SEQ ID NO:10 given in SEQ ID NO:9, the coding sequence for SEQ ID NO:12 given in SEQ ID NO:11, the coding sequence for SEQ ID NO:14 given in SEQ ID NO:13, the coding sequence for SEQ ID NO:16 given in SEQ ID NO:15, the coding sequence for SEQ ID NO:18 given in SEQ ID NO:17, the coding sequence for SEQ ID NO:24 given in SEQ ID NO:23, the coding sequence for SEQ ID NO:26 given in SEQ ID NO:25, or is a nucleic acid molecule that is complementary thereto. Particularly preferred is a nucleic acid which comprises or consists of a region that is at least 80% identical over its entire length to the coding sequence for the extracellular domain of INSP052 (the extracellular domain of mature INSP052 or the extracellular domain of INSP052 comprising the signal peptide) as given in FIG. 7. In this regard, nucleic acid molecules at least 90%, preferably at least 95%, more preferably at least 98% or 99% identical over their entire length to the same are particularly preferred. Preferred embodiments in this respect are nucleic acid molecules that encode polypeptides which retain substantially the same biological function or activity as the INSP052 and INSP055 polypeptides.

The invention also provides a process for detecting a nucleic acid molecule of the invention, comprising the steps of: (a) contacting a nucleic probe according to the invention with a biological sample under hybridizing conditions to form duplexes; and (b) detecting any such duplexes that are formed.

As discussed additionally below in connection with assays that may be utilised according to the invention, a nucleic acid molecule as described above may be used as a hybridization probe for RNA, cDNA or genomic DNA, in order to isolate full-length cDNAs and genomic clones encoding the INSP052 and INSP055 polypeptides and to isolate cDNA and genomic clones of homologous or orthologous genes that have a high sequence similarity to the gene encoding this polypeptide.

In this regard, the following techniques, among others known in the art, may be utilised and are discussed below for purposes of illustration. Methods for DNA sequencing and analysis are well known and are generally available in the art and may, indeed, be used to practice many of the embodiments of the invention discussed herein. Such methods may employ such enzymes as the Klenow fragment of DNA polymerase I, Sequenase (US Biochemical Corp, Cleveland, Ohio), Taq polymerase (Perkin Elmer), thermostable T7 polymerase (Amersham, Chicago, Ill.), or combinations of polymerases and proof-reading exonucleases such as those found in the ELONGASE Amplification System marketed by Gibco/BRL (Gaithersburg, Md.). Preferably, the sequencing process may be automated using machines such as the Hamilton Micro Lab 2200 (Hamilton, Reno, Nev.), the Peltier Thermal Cycler (PTC200; MJ Research, Watertown, Mass.) and the ABI Catalyst and 373 and 377 DNA Sequencers (Perkin Elmer).

One method for isolating a nucleic acid molecule encoding a polypeptide with an equivalent function to that of the INSP052 and INSP055 polypeptides is to probe a genomic or cDNA library with a natural or artificially-designed probe using standard procedures that are recognised in the art (see, for example, "Current Protocols in Molecular Biology", Ausubel et al. (eds). Greene Publishing Association and John Wiley Interscience, New York, 1989,1992). Probes comprising at least 15, preferably at least 30, and more preferably at least 50, contiguous bases that correspond to, or are complementary to, nucleic acid sequences from the appropriate encoding gene (SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25) are particularly useful probes. Such probes may be labelled with an analytically-detectable reagent to facilitate their identification. Useful reagents include, but are not limited to, radioisotopes, fluorescent dyes and enzymes that are capable of catalysing the formation of a detectable product. Using these probes, the ordinarily skilled artisan will be capable of isolating complementary copies of genomic DNA, cDNA or RNA polynucleotides encoding proteins of interest from human, mammalian or other animal sources and screening such sources for related sequences, for example, for additional members of the family, type and/or subtype.

In many cases, isolated cDNA sequences will be incomplete, in that the region encoding the polypeptide will be cut short, normally at the 5' end. Several methods are available to obtain full length cDNAs, or to extend short cDNAs. Such sequences may be extended utilising a partial nucleotide sequence and employing various methods known in the art to detect upstream sequences such as promoters and regulatory elements. For example, one method which may be employed is based on the method of Rapid Amplification of cDNA Ends (RACE; see, for example, Frohman et al., PNAS USA 85, 8998-9002, 1988). Recent modifications of this technique, exemplified by the Marathon™ technology (Clontech Laboratories Inc.), for example, have significantly simplified the search for longer cDNAs. A slightly different technique, termed "restriction-site" PCR, uses universal primers to retrieve unknown nucleic acid sequence adjacent a known locus (Sarkar, G. (1993) PCR Methods Applic. 2:318-322). Inverse PCR may also be used to amplify or to extend sequences using divergent primers based on a known region (Triglia, T. et al. (1988) Nucleic Acids Res. 16:8186). Another method which may be used is capture PCR which involves PCR amplification of DNA fragments adjacent a known sequence in human and yeast artificial chromosome DNA (Lagerstrom, M. et al. (1991) PCR Methods Applic., 1, 111-119). Another method which may be used to retrieve unknown sequences is that of Parker, J. D. et al. (1991); Nucleic Acids Res. 19:3055-3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

In one embodiment of the invention, the nucleic acid molecules of the present invention may be used for chromosome localisation. In this technique, a nucleic acid molecule is specifically targeted to, and can hybridize with, a particular location on an individual human chromosome. The mapping of relevant sequences to chromosomes according to the present invention is an important step in the confirmatory correlation of those sequences with the gene-associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationships between genes and diseases that have been mapped to the same chromosomal region are then identified through linkage analysis (coinheritance of physically adjacent genes). This provides valuable information to investigators searching for disease genes using positional cloning or other gene discovery techniques. Once the disease or syndrome has been crudely localised by genetic linkage to a particular genomic region, any sequences mapping to that area may represent associated or regulatory genes for further investigation. The nucleic acid molecule may also be used to detect differences in the chromosomal location due to translocation, inversion, etc. among normal, carrier, or affected individuals.

The nucleic acid molecules of the present invention are also valuable for tissue localisation such techniques allow the determination of expression patterns of the polypeptide in tissues by detection of the mRNAs that encode them. These techniques include in situ hybridization techniques and nucleotide amplification techniques, such as PCR. Results from these studies provide an indication of the normal functions of the polypeptide in the organism. In addition, comparative studies of the normal expression pattern of mRNAs with that of mRNAs encoded by a mutant gene provide valuable insights into the role of mutant polypeptides in disease. Such inappropriate expression may be of a temporal, spatial or quantitative nature.

Gene silencing approaches may also be undertaken to down-regulate endogenous expression of a gene encoding a polypeptide of the invention. RNA interference (RNAi) (Elbashir, S M et al., Nature 2001, 411, 494-498) is one method of sequence specific post-transcriptional gene silencing that may be employed. Short dsRNA oligonucleotides are synthesised in vitro and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The vectors of the present invention comprise nucleic acid molecules of the invention and may be cloning or expression vectors. The host cells of the invention, which may be transformed, transfected or transduced with the vectors of the invention may be prokaryotic or eukaryotic.

The polypeptides of the invention may be prepared in recombinant form by expression of their encoding nucleic acid molecules in vectors contained within a host cell. Such expression methods are well known to those of skill in the art and many are described in detail by Sambrook et al (supra) and Fernandez & Hoeffler (1998, eds. "Gene expression systems. Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the encoding gene can be placed under the control of a control element such as a promoter, ribosome binding site (for bacterial expression) and, optionally an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems.

Cell-free translation systems can also be employed to produce the polypeptides of the invention.

Introduction of nucleic acid molecules encoding a polypeptide of the present invention into host cells can be effected by methods described in many standard laboratory manuals, such as Davis et al., Basic Methods in Molecular Biology (1986) and Sambrook et al., [supra]. Particularly suitable methods include calcium phosphate transfection, DEAE-dextran mediated transfection, transvection, microinjection, cationic lipid-mediated transfection, electroporation, transduction, scrape loading, ballistic introduction or infection (see Sambrook et al., 1989 [supra]; Ausubel et al., 1991 [supra]; Spector, Goldman & Leinwald, 1998). In eukaryotic cells, expression systems may either be transient (for example, episomal) or permanent (chromosomal integration) according to the needs of the system.

The encoding nucleic acid molecule may or may not include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing.

In addition to control sequences, it may be desirable to add regulatory sequences that allow for regulation of the expression of the polypeptide relative to the growth of the host cell. Examples of regulatory sequences are those which cause the expression of a gene to be increased or decreased in response to a chemical or physical stimulus, including the presence of a regulatory compound or to various temperature or metabolic conditions. Regulatory sequences are those non-translated regions of the vector, such as enhancers, promoters and 5' and 3' untranslated regions. These interact with host cellular proteins to carry out transcription and translation. Such regulatory sequences may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the Bluescript phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (for example, heat shock, RUBISCO and storage protein genes) or from plant viruses (for example, viral promoters or leader sequences) may be cloned into the vector. In mammalian cell systems, promoters from mammalian genes or from mammalian viruses are preferable. If it is necessary to generate a cell line that contains multiple copies of the sequence, vectors based on SV40 or EBV may be used with an appropriate selectable marker.

An expression vector is constructed so that the particular nucleic acid coding sequence is located in the vector with the appropriate regulatory sequences, the positioning and orientation of the coding sequence with respect to the regulatory sequences being such that the coding sequence is transcribed under the "control" of the regulatory sequences, i.e., RNA polymerase which binds to the DNA molecule at the control sequences transcribes the coding sequence. In some cases it may be necessary to modify the sequence so that it may be attached to the control sequences with the appropriate orientation; i.e., to maintain the reading frame.

The control sequences and other regulatory sequences may be ligated to the nucleic acid coding sequence prior to insertion into a vector. Alternatively, the coding sequence can be cloned directly into an expression vector that already contains the control sequences and an appropriate restriction site.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines.

In the baculovirus system, the materials for baculovirus/insect cell expression systems are commercially available in kit form from, inter alia, Invitrogen, San Diego Calif. (the "MaxBac" kit). These techniques are generally known to those skilled in the art and are described fully in Summers and Smith, Texas Agricultural Experiment Station Bulletin No. 1555 (1987). Particularly suitable host cells for use in this system include insect cells such as Drosophila S2 and Spodoptera Sf9 cells.

There are many plant cell culture and whole plant genetic expression systems known in the art. Examples of suitable plant cellular genetic expression systems include those described in U.S. Pat. No. 5,693,506; U.S. Pat. No. 5,659,122; and U.S. Pat. No. 5,608,143. Additional examples of genetic expression in plant cell culture has been described by Zenk, Phytochemistry 30, 3861-3863 (1991).

In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of particularly preferred bacterial host cells include streptococci, staphylococci, *E. coli, Streptomyces* and *Bacillus subtilis* cells.

Examples of particularly suitable host cells for fungal expression include yeast cells (for example, *S. cerevisiae*) and *Aspergillus* cells.

Any number of selection systems are known in the art that may be used to recover transformed cell lines. Examples include the herpes simplex virus thymidine kinase (Wigler, M. et al. (1977) Cell 11:223-32) and adenine phosphoribosyltransferase (Lowy, I. et al. (1980) Cell 22:817-23) genes that can be employed in tk- or aprt± cells, respectively.

Also, antimetabolite, antibiotic or herbicide resistance can be used as the basis for selection; for example, dihydrofolate reductase (DHFR) that confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively. Additional selectable genes have been described, examples of which will be clear to those of skill in the art.

Although the presence or absence of marker gene expression suggests that the gene of interest is also present, its presence and expression may need to be confirmed. For example, if the relevant sequence is inserted within a marker gene sequence, transformed cells containing the appropriate sequences can be identified by the absence of marker gene function. Alternatively, a marker gene can be placed in tandem with a sequence encoding a polypeptide of the invention under the control of a single promoter. Expression of the marker gene in response to induction or selection usually indicates expression of the tandem gene as well.

Alternatively, host cells that contain a nucleic acid sequence encoding a polypeptide of the invention and which express said polypeptide may be identified by a variety of procedures known to those of skill in the art. These procedures include, but are not limited to, DNA-DNA or DNA-RNA hybridizations and protein bioassays, for example, fluorescence activated cell sorting (FACS) or immunoassay techniques (such as the enzyme-linked immunosorbent assay

[ELISA] and radioimmunoassay [RIA]), that include membrane, solution, or chip based technologies for the detection and/or quantification of nucleic acid or protein (see Hampton, R. et al. (1990) Serological Methods, a Laboratory Manual, APS Press, St Paul, Minn.) and Maddox, D. E. et al. (1983) J. Exp. Med, 158, 1211-1216).

A wide variety of labels and conjugation techniques are known by those skilled in the art and may be used in various nucleic acid and amino acid assays. Means for producing labelled hybridization or PCR probes for detecting sequences related to nucleic acid molecules encoding polypeptides of the present invention include oligolabelling, nick translation, end-labelling or PCR amplification using a labelled polynucleotide. Alternatively, the sequences encoding the polypeptide of the invention may be cloned into a vector for the production of an mRNA probe. Such vectors are known in the art, are commercially available, and may be used to synthesise RNA probes in vitro by addition of an appropriate RNA polymerase such as T7, T3 or SP6 and labelled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)).

Suitable reporter molecules or labels, which may be used for ease of detection, include radionuclides, enzymes and fluorescent, chemiluminescent or chromogenic agents as well as substrates, cofactors, inhibitors, magnetic particles, and the like.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the polypeptides of the present invention.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is particularly useful for purification. Well known techniques for refolding proteins may be employed to regenerate an active conformation when the polypeptide is denatured during isolation and or purification.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as histidine-tryptophan modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the polypeptide of the invention may be used to facilitate purification. One such expression vector provides for expression of a fusion protein containing the polypeptide of the invention fused to several histidine residues preceding a thioredoxin or an enterokinase cleavage site. The histidine residues facilitate purification by IMAC (immobilised metal ion affinity chromatography as described in Porath, J. et al. (1992), Prot. Exp. Purif. 3: 263-281) while the thioredoxin or enterokinase cleavage site provides a means for purifying the polypeptide from the fusion protein. A discussion of vectors which contain fusion proteins is provided in Kroll, D. J. et al. (1993; DNA Cell Biol. 12:441-453).

If the polypeptide is to be expressed for use in screening assays, generally it is preferred that it be produced at the surface of the host cell in which it is expressed. In this event, the host cells may be harvested prior to use in the screening assay, for example using techniques such as fluorescence activated cell sorting (FACS) or immunoaffinity techniques. If the polypeptide is secreted into the medium, the medium can be recovered in order to recover and purify the expressed polypeptide. If polypeptide is produced intracellularly, the cells must first be lysed before the polypeptide is recovered.

The polypeptide of the invention can be used to screen libraries of compounds in any of a variety of drug screening techniques. Such compounds may activate (agonise) or inhibit (antagonise) the level of expression of the gene or the activity of the polypeptide of the invention and form a further aspect of the present invention. Preferred compounds are effective to alter the expression of a natural gene which encodes a polypeptide of the first aspect of the invention or to regulate the activity of a polypeptide of the first aspect of the invention.

Agonist or antagonist compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al., Current Protocols in Immunology 1(2):Chapter 5 (1991).

Compounds that are most likely to be good antagonists are molecules that bind to the polypeptide of the invention without inducing the biological effects of the polypeptide upon binding to it. Potential antagonists include small organic molecules, peptides, polypeptides and antibodies that bind to the polypeptide of the invention and thereby inhibit or extinguish its activity. In this fashion, binding of the polypeptide to normal cellular binding molecules may be inhibited, such that the normal biological activity of the polypeptide is prevented.

The polypeptide of the invention that is employed in such a screening technique may be free in solution, affixed to a solid support, borne on a cell surface or located intracellularly. In general, such screening procedures may involve using appropriate cells or cell membranes that express the polypeptide that are contacted with a test compound to observe binding, or stimulation or inhibition of a functional response. The functional response of the cells contacted with the test compound is then compared with control cells that were not contacted with the test compound. Such an assay may assess whether the test compound results in a signal generated by activation of the polypeptide, using an appropriate detection system. Inhibitors of activation are generally assayed in the presence of a known agonist and the effect on activation by the agonist in the presence of the test compound is observed.

A preferred method for identifying an agonist or antagonist compound of a polypeptide of the present invention comprises:

(a) contacting a cell expressing on the surface thereof the polypeptide according to the first aspect of the invention, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by measuring the level of a signal generated from the interaction of the compound with the polypeptide.

A further preferred method for identifying an agonist or antagonist of a polypeptide of the invention comprises:

(a) contacting a cell expressing on the surface thereof the polypeptide, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by comparing the level of a signal generated from the interaction of the compound with the polypeptide with the level of a signal in the absence of the compound.

In further preferred embodiments, the general methods that are described above may further comprise conducting the identification of agonist or antagonist in the presence of labelled or unlabelled ligand for the polypeptide.

In another embodiment of the method for identifying agonist or antagonist of a polypeptide of the present invention comprises:

determining the inhibition of binding of a ligand to cells which have a polypeptide of the invention on the surface thereof, or to cell membranes containing such a polypeptide, in the presence of a candidate compound under conditions to permit binding to the polypeptide, and determining the amount of ligand bound to the polypeptide. A compound capable of causing reduction of binding of a ligand is considered to be an agonist or antagonist. Preferably the ligand is labelled.

More particularly, a method of screening for a polypeptide antagonist or agonist compound comprises the steps of:

(a) incubating a labelled ligand with a whole cell expressing a polypeptide according to the invention on the cell surface, or a cell membrane containing a polypeptide of the invention, (b) measuring the amount of labelled ligand bound to the whole cell or the cell membrane;

(c) adding a candidate compound to a mixture of labelled ligand and the whole cell or the cell membrane of step (a) and allowing the mixture to attain equilibrium;

(d) measuring the amount of labelled ligand bound to the whole cell or the cell membrane after step (c); and (e) comparing the difference in the labelled ligand bound in step (b) and (d), such that the compound which causes the reduction in binding in step (d) is considered to be an agonist or antagonist.

The polypeptides may be found to modulate a variety of physiological and pathological processes in a dose-dependent manner in the above-described assays. Thus, the "functional equivalents" of the polypeptides of the invention include polypeptides that exhibit any of the same modulatory activities in the above-described assays in a dose-dependent manner. Although the degree of dose-dependent activity need not be identical to that of the polypeptides of the invention, preferably the "functional equivalents" will exhibit substantially similar dose-dependence in a given activity assay compared to the polypeptides of the invention.

In certain of the embodiments described above, simple binding assays may be used, in which the adherence of a test compound to a surface bearing the polypeptide is detected by means of a label directly or indirectly associated with the test compound or in an assay involving competition with a labelled competitor. In another embodiment, competitive drug screening assays may be used, in which neutralising antibodies that are capable of binding the polypeptide specifically compete with a test compound for binding. In this manner, the antibodies can be used to detect the presence of any test compound that possesses specific binding affinity for the polypeptide.

Persons skilled in the art will be able to devise assays for identifying modulators of a polypeptide of the invention. Of interest in this regard is Lokker N A et al J Biol Chem 1997 Dec. 26;272(52):33037-44 which reports an example of an assay to identify antagonists (in this case neutralizing antibodies).

Assays may also be designed to detect the effect of added test compounds on the production of mRNA encoding the polypeptide in cells. For example, an ELISA may be constructed that measures secreted or cell-associated levels of polypeptide using monoclonal or polyclonal antibodies by standard methods known in the art, and this can be used to search for compounds that may inhibit or enhance the production of the polypeptide from suitably manipulated cells or tissues. The formation of binding complexes between the polypeptide and the compound being tested may then be measured.

Assay methods that are also included within the terms of the present invention are those that involve the use of the genes and polypeptides of the invention in overexpression or ablation assays. Such assays involve the manipulation of levels of these genes/polypeptides in cells and assessment of the impact of this manipulation event on the physiology of the manipulated cells. For example, such experiments reveal details of signalling and metabolic pathways in which the particular genes/polypeptides are implicated, generate information regarding the identities of polypeptides with which the studied polypeptides interact and provide clues as to methods by which related genes and proteins are regulated.

Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

The polypeptide of the invention may be used to identify membrane-bound or soluble receptors, through standard receptor binding techniques that are known in the art, such as ligand binding and crosslinking assays in which the polypeptide is labelled with a radioactive isotope, is chemically modified, or is fused to a peptide sequence that facilitates its detection or purification, and incubated with a source of the putative receptor (for example, a composition of cells, cell membranes, cell supernatants, tissue extracts, or bodily fluids). The efficacy of binding may be measured using biophysical techniques such as surface plasmon resonance and spectroscopy. Binding assays may be used for the purification and cloning of the receptor, but may also identify agonists and antagonists of the polypeptide, that compete with the binding of the polypeptide to its receptor. Standard methods for conducting screening assays are well understood in the art.

The invention also includes a screening kit useful in the methods for identifying agonists, antagonists, ligands, receptors, substrates, enzymes, that are described above.

The invention includes the agonists, antagonists, ligands, receptors, substrates and enzymes, and other compounds which modulate the activity or antigenicity of the polypeptide of the invention discovered by the methods that are described above.

The invention also provides pharmaceutical compositions comprising a polypeptide, nucleic acid, ligand or compound of the invention in combination with a suitable pharmaceutical carrier. These compositions may be suitable as therapeutic or diagnostic reagents, as vaccines, or as other immunogenic compositions, as outlined in detail below.

According to the terminology used herein, a composition containing a polypeptide, nucleic acid, ligand or compound [X] is "substantially free of" impurities [herein, Y] when at least 85% by weight of the total X+Y in the composition is X. Preferably, X comprises at least about 90% by weight of the total of X+Y in the composition, more preferably at least about 95%, 98% or even 99% by weight.

The pharmaceutical compositions should preferably comprise a therapeutically effective amount of the polypeptide, nucleic acid molecule, ligand, or compound of the invention. The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 50 mg/kg, preferably 0.05 mg/kg to 10 mg/kg. Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intra-arterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

If the activity of the polypeptide of the invention is in excess in a particular disease state, several approaches are available. One approach comprises administering to a subject an inhibitor compound (antagonist) as described above, along with a pharmaceutically acceptable carrier in an amount effective to inhibit the function of the polypeptide, such as by blocking the binding of ligands, substrates, enzymes, receptors, or by inhibiting a second signal, and thereby alleviating the abnormal condition. Preferably, such antagonists are antibodies. Most preferably, such antibodies are chimeric and/or humanised to minimise their immunogenicity, as described previously.

In another approach, soluble forms of the polypeptide that retain binding affinity for the ligand, substrate, enzyme, receptor, in question, may be administered. Typically, the polypeptide may be administered in the form of fragments that retain the relevant portions.

In an alternative approach, expression of the gene encoding the polypeptide can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the gene encoding the polypeptide. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes. Such oligonucleotides may be administered or may be generated in situ from expression in vivo.

In addition, expression of the polypeptide of the invention may be prevented by using ribozymes specific to its encoding mRNA sequence. Ribozymes are catalytically active RNAs that can be natural or synthetic (see for example Usman, N, et al., Curr. Opin. Struct. Biol (1996) 6(4), 527-33). Synthetic ribozymes can be designed to specifically cleave mRNAs at selected positions thereby preventing translation of the mRNAs into functional polypeptide. Ribozymes may be synthesised with a natural ribose phosphate backbone and natural bases, as normally found in RNA molecules. Alternatively the ribozymes may be synthesised with non-natural backbones, for example, 2'-O-methyl RNA, to provide protection from ribonuclease degradation and may contain modified bases.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine and butosine, as well as acetyl-, methyl-, thio- and similarly modified forms of adenine, cytidine, guanine, thymine and uridine which are not as easily recognised by endogenous endonucleases.

For treating abnormal conditions related to an under-expression of the polypeptide of the invention and its activity, several approaches are also available. One approach comprises administering to a subject a therapeutically effective amount of a compound that activates the polypeptide, i.e., an agonist as described above, to alleviate the abnormal condition. Alternatively, a therapeutic amount of the polypeptide in combination with a suitable pharmaceutical carrier may be administered to restore the relevant physiological balance of polypeptide.

Gene therapy may be employed to effect the endogenous production of the polypeptide by the relevant cells in the subject. Gene therapy is used to treat permanently the inappropriate production of the polypeptide by replacing a defective gene with a corrected therapeutic gene.

Gene therapy of the present invention can occur in vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus as described by Berkner, K. L., in Curr. Top. Microbiol. Immunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. For example, a nucleic acid molecule encoding a polypeptide of the invention may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

In situations in which the polypeptides or nucleic acid molecules of the invention are disease-causing agents, the invention provides that they can be used in vaccines to raise antibodies against the disease causing agent.

Vaccines according to the invention may either be prophylactic (ie. to prevent infection) or therapeutic (ie. to treat disease after infection). Such vaccines comprise immunising antigen(s), immunogen(s), polypeptide(s), protein(s) or nucleic acid, usually in combination with pharmaceutically-acceptable carriers as described above, which include any carrier that does not itself induce the production of antibodies harmful to the individual receiving the composition. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, and other pathogens.

Since polypeptides may be broken down in the stomach, vaccines comprising polypeptides are preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

Genetic delivery of antibodies that bind to polypeptides according to the invention may also be effected, for example, as described in International patent application WO98/55607.

The technology referred to as jet injection (see, for example, www.powderject.com) may also be useful in the formulation of vaccine compositions.

A number of suitable methods for vaccination and vaccine delivery systems are described in International patent application WO00/29428.

This invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified enzymatically by using PCR, ligase chain reaction (LCR), strand displacement amplification (SDA), or other amplification techniques (see Saiki et al., Nature, 324, 163-166 (1986); Bej, et al., Crit. Rev. Biochem. Molec. Biol., 26, 301-334 (1991); Birkenmeyer et al., J. Virol. Meth., 35, 117-126 (1991); Van Brunt, J., Bio/Technology, 8, 291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:

a) contacting a sample of tissue from the patient with a nucleic acid probe under stringent conditions that allow the formation of a hybrid complex between a nucleic acid molecule of the invention and the probe;

b) contacting a control sample with said probe under the same conditions used in step a);

c) and detecting the presence of hybrid complexes in said samples;

wherein detection of levels of the hybrid complex in the patient sample that differ from levels of the hybrid complex in the control sample is indicative of disease.

A further aspect of the invention comprises a diagnostic method comprising the steps of:

a) obtaining a tissue sample from a patient being tested for disease;

b) isolating a nucleic acid molecule according to the invention from said tissue sample; and c) diagnosing the patient for disease by detecting the presence of a mutation in the nucleic acid molecule which is associated with disease.

To aid the detection of nucleic acid molecules in the above-described methods, an amplification step, for example using PCR, may be included.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mismatched duplexes by RNase digestion or by assessing differences in melting temperatures. The presence or absence of the mutation in the patient may be detected by contacting DNA with a nucleic acid probe that hybridises to the DNA under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)).

For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230: 1242). Sequence changes at specific locations may also be revealed by nuclease protection assays, such as RNase and S1 protection or the chemical cleavage method (see Cotton et al., Proc. Natl. Acad. Sci. USA (1985) 85: 4397-4401).

In addition to conventional gel electrophoresis and DNA sequencing, mutations such as microdeletions, aneuploidies, translocations, inversions, can also be detected by in situ analysis (see, for example, Keller et al., DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al., Science, 250, 559-562 (1990), and Trask et al., Trends, Genet., 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al); Lockhart, D. J. et al. (1996) Nat. Biotech. 14: 1675-1680); and Schena, M. et al. (1996) Proc. Natl. Acad. Sci. 93: 10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jet application apparatus, as described in PCT application WO95/25116 (Baldeschweiler et al). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis and ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA, RIA, and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation The amount of standard complex formation may be quantified by various methods, such as by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, with a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:
(a) a nucleic acid molecule of the present invention;
(b) a polypeptide of the present invention; or
(c) a ligand of the present invention.

In one aspect of the invention, a diagnostic kit may comprise a first container containing a nucleic acid probe that hybridises under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to disease, including, but not limited to, diseases including, but not limited to, cell proliferative disorders, autoimmune/inflammatory disorders, cardiovascular disorders, neurological and psychiatric disorders, developmental disorders, genetic disorders, metabolic disorders, infections and other pathological conditions. These diseases preferably include neoplasm, cancer, brain tumour, glioma, bone tumor, lung tumor, breast tumour, prostate tumour, colon tumour, hemangioma, myeloproliferative disorder, leukemia, hematological disease, neutropenia, thrombocytopenia, angiogenesis disorders, dermatological disease, ageing, wounds, burns, fibrosis, cardiovascular disease, restensosis, heart disease, peripheral vascular disease, coronary artery disease, oedema, thromboembolism, dysmenorrhea, endometriosis, pre-eclampsia, lung disease, COPD, asthma bone disease, renal disease, glomerulonephritis, liver disease, Crohn's disease, gastritis, ulcerative colitis, ulcer, immune disorder, autoimmune disease, arthritis, rheumatoid arthritis, psoriasis, epidermolysis bullosa, systemic lupus erythematosus, ankylosing spondylitis, Lyme disease, multiple sclerosis, neurodegeneration, stroke, brain/spinal cord injury, Alzheimer's disease, Parkinson's disease, motor neurone disease, neuromuscular disease, HIV, AIDS, cytomegalovirus infection, fungal infection, ocular disorder, macular degeneration, glaucoma, diabetic retinopathy, ocular hypertension and other conditions in which immunoglobulin domain containing cell recognition molecules are implicated.

Various aspects and embodiments of the present invention will now be described in more detail by way of example, with particular reference to the INSP052 and INSP055 polypeptides.

It will be appreciated that modification of detail may be made without departing from the scope of the invention.

BRIEF DESCRIPTION OF THE FIGURES

FIG. 1: Results from BLAST against NCBI non-redundant database using full-length INSP052 polypeptide sequence.

FIG. 2: Alignment generated by BLAST between the full-length INSP052 polypeptide sequence and the closest related sequence, biliary glycoprotein H (mouse).

FIG. 3: Results from BLAST against NCBI non-redundant database using full-length INSP055 polypeptide sequence.

FIG. 4: Alignment generated by BLAST between the full-length INSP055 polypeptide sequence and the closest related sequence, biliary glycoprotein H (mouse).

FIG. 5: Predicted nucleotide sequence of INSP052 with translation underlined sequence denotes predicted signal peptide. Boxed sequence denotes predicted transmembrane domain.

FIG. 6: INSP052 coding exon organization in genomic DNA. Bottom=INSP052.cDNA, 1251 bp. Top=chr11.genomic_DNA. Sequence encoding the putative extracellular domain is underlined. Start and Stop codons are in bold type.

FIG. 7: Nucleotide sequence and translation of cloned INSP052 extracellular domain.
   Underlined sequence denotes predicted signal peptide.
FIG. 8: Map of pENTR-INSP052-EC-6HIS
FIG. 9: Map of pEAK12d-INSP052-EC-6HIS
FIG. 10: % secreted TNF (see Example 4)

FIG. 13.

EXAMPLES

Example 1

INSP052 and INSP055

Figure 11:
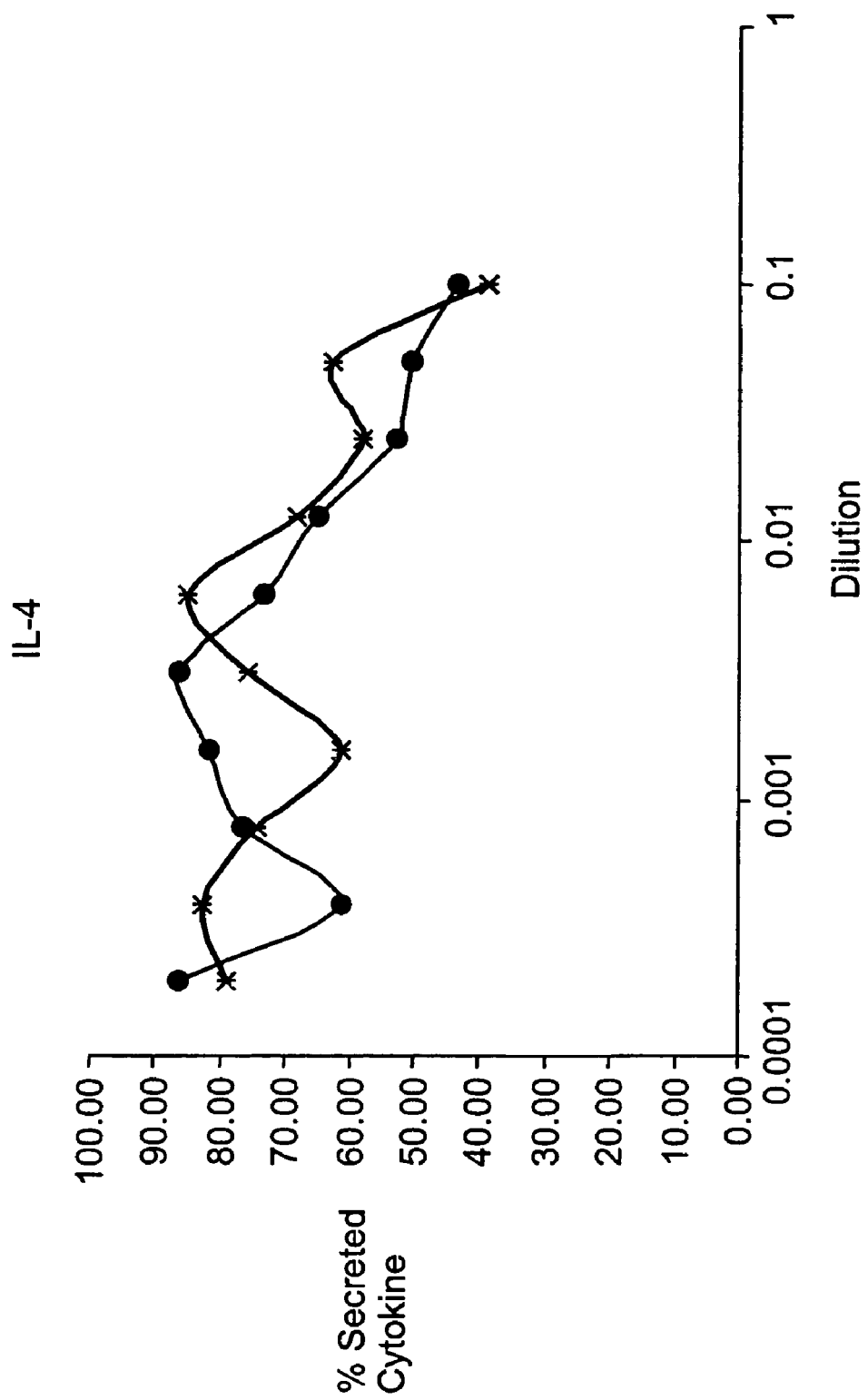
FIG. 11: % secreted IL-4 (see Example 4)

The polypeptide sequence derived from combining SEQ ID NO:2, SEQ ID NO:4, SEQ ID NO:6, SEQ ID NO:8, SEQ ID NO:10, SEQ ID NO:12 and SEQ ID NO:14 and SEQ ID NO:16 which represents the translation of consecutive exons from INSP052 is derived from human genomic sequence. The polynucleotide and polypeptide sequences SEQ ID NO 17 and SEQ ID NO 18 representing INSP055 are polynucleotide and polypeptide sequences of the mouse orthologue of INSP052 respectively. The existence of a mouse orthologue supports the gene model for the human sequence INSP052.

INSP052 and INSP055 polypeptide sequences represented by SEQ ID NO 16 and SEQ ID NO 18, respectively, are predicted to contain signal peptide sequences and a transmembrane spanning domain.

The polypeptide sequence derived from combining SEQ ID NO:2, SEQ ID NO:4, SEQ ID NO:6, SEQ ID NO:8, SEQ ID NO:11, SEQ ID NO:12 and SEQ ID NO:14 and SEQ ID NO:16 which represents the translation of consecutive exons from INSP052, was used as a BLAST query against the NCBI non-redundant Sequence database. The top ten matches are shown in FIG. 1, all of which are immunoglobulin domain containing proteins.

FIG. 2 shows the alignment of the INSP052 query sequence to the sequence of the highest matching known protein, biliary glycoprotein H (mouse).

The polypeptide sequence INSP055, was used as a BLAST query against the NCBI non-redundant Sequence database. The top ten matches are shown in FIG. 3. FIG. 4 shows the alignment of the INSP055 query sequence to the sequence of the highest matching known protein, biliary glycoprotein H (mouse).

Expressed sequence tags (ESTs) representing the INSP052 and INSP055 transcripts in human and mouse originate from the following cDNA libraries: brain, including cerebellum, cortex, hippocampus, hypothalamus, medulla oblongata; inner ear and breast. Transcripts are also represented by ESTs from oligodendroglioma, glioblastoma and multiple sclerosis lesions. This suggests that INSP052 can be cloned from the above tissues and may be associated with diseases of the above tissues. Accordingly, the polypeptides, antibodies and other moieties described herein may have utility in the treating a disease in one of the above tissues.

Example 2

Cloning of the INSP052 Extracellular Domain by Exon Assembly

The INSP052 full length prediction encodes a type I membrane protein of 416 amino acids, related to the VEGF/PDGF receptors, belonging to the immunoglobulin superfamily. The predicted nucleotide sequence, starting from the initiating ATG codon to the poly A tail is 2025 nucleotides long (FIG. 5). The coding sequence (cds) spans 7 exons (FIG. 6). A putative signal sequence (encoding amino acids 1-33) is located in exon 1. The sequence encoding the predicted transmembrane (TM) domain (amino acids 241 to 263) is located at the exon 3-4 boundary.

The extracellular (EC) domain encoding amino acids 1-240 was cloned by exon assembly from genomic DNA. An overview of the exon assembly method is summarized below:

Individual exons 1, 2 and 3 were amplified from genomic DNA by PCR. The reverse primer for exon 3 also contained an 11 base overlap with the 5' sequence of exon 4. Gel-purified exons were mixed and a 2nd PCR reaction was performed to amplify the re-assembled DNA.

The full length PCR product corresponding to the INSP052 EC domain was gel-purified and subcloned sequentially into pDONR 201 (Gateway entry vector) and pEAK12d (expression vector) using the Invitrogen Gateway™ methodology.

1. Pcr Amplification of Exons Encoding the Extracellular Domain of INSP052 From Genomic DNA.

PCR primers were designed to amplify exons 1, 2 and 3 individually (table 1). The forward primer for exon 1 (INSP052-B1P-exon1F) also contains the partial sequence of the Gateway attB1 site (5' GCAGGCTTC ) and a Kozak sequence (5' GCCACC). The reverse primer for exon 1 (INSP052-exon1R) has an overlap of 18 bases with exon 2 at its 5' end. The forward primer for exon 2 (INSP052-exon2F) has an 18 bp overlap with exon 1 at its 5' end. The reverse primer for exon 2 (INSP052-exon2R) has an overlap of 18 bases with exon 3 at its 5' end. The forward primer for exon 3 (INSP052-exon3F) contains an 17 bp overlap with exon 2 at its 5' end. The reverse primer for exon 3 (INSP052-exon3R) has an overlap of 11 bases with exon 4 at its 5' end.

For amplification of INSP052 exon 1, the PCR reaction was performed in a final volume of 50 µl and contained 1.5 µl of human genomic DNA (0.1 µg/µl, Novagen cat. no. 69237). 2 µl of 5 mM dNTPs (Amersham Pharmacia Biotech), 6 µl of INSP052-B1P-exon1F (10 µM), 6 µl of INSP052-exon1R , 5 µl of 10×Pwo buffer and 0.5 µl of Pwo polymerase (5 U/µl) (Roche, cat. no. 1 644 955). The PCR conditions were 94° C. for 2 min; 35 cycles of 94° C. for 30 s, 60° C. for 30 s and 72° C. for 1 min; an additional elongation cycle of 72° C. for 5 min; and a holding cycle of 4° C. Reaction products were loaded onto a 1.5% agarose gel (1×TAE) and PCR products of the correct size (118 bp) were gel-purified using a Qiaquick Gel Extraction Kit (Qiagen cat. no. 28704) and eluted in 50 µl of elution buffer (Qiagen).

Exon 2 was amplified using the same reaction conditions with primers INSP052-exon2F and INSP052-exon2R. PCR products of 378 bp were gel purified as above.

Exon 3 was amplified using the same reaction conditions with primers INSP052-exon3F and INSP052-exon3R. PCR products of 321 bp were gel purified as above.

2. Assembly of Extracellular Domain-encoding Exons of INSP052

Exons 1, 2 and 3-4 were re-assembled in a PCR reaction containing 5 µl of each gel purified exon, 2 µl of 5 mM dNTPs, 6 µl of INSP052-B1P-exon1F (10 µM), 6 µl of INSP052-5HIS-R (10 µM), 5 µl of 10×Pfu buffer, 14.5 µl H₂O and 0.5 µl Pfu polymerase (3 U/µl; Promega cat. no. M774B). The reaction conditions were: 94° C., 4 min; 10 cycles of 94° C. for 30 s, 48° C. for 30 s and 70° C. for 2 min; 25 cycles of 94° C. for 30 s, 52° C., for 30 s and 70° C. for 2 min ; an additional elongation step of 70° C. for 10 min; and a holding cycle at 4° C. Reaction products were analysed on a 1.5% agarose gel (1×TAE). PCR products of the correct size (750 bp) were gel purified using a Qiaquick Gel Extraction Kit (Qiagen cat. no. 28704) and eluted in 50 µl of elution buffer (Qiagen). The resultant product (INSP052 EC ORF) contains the ORF of the INSP052 EC domain flanked at the 5' end by an attB1 site and Kozak sequence, and at the 3' end by a 5HIS tag encoding sequence.

3. Subcloning of the INSP052 EC Domain ORF into pDONR201

AttB1 and attB2 recombination sites were added to the 5' and 3' end of the full length INSP052 EC domain sequence in a PCR reaction containing 2 µl of gel purified INSP052 EC ORF, 2 µl of 5 mM dNTPs (Amersham Pharmacia Biotech), 6 µl of GCP-Forward (10 µM), 6 µl of GCP-Reverse (10 µM), 5 µl of 10×Vent buffer and 0.5 µl of Vent DNA polymerase (2 U/µl) (New England Biolabs, cat. no. M0254S) in a final volume of 50 µl. The PCR conditions were 94° C. for 2 min; 30 cycles of 94° C. for 30 sec; 55° C. for 30 sec and 72° C. for 1 min; an additional elongation step of 72° C. for 3 min and a holding cycle of 4° C. Reaction products were analysed on a 1.5% agarose gel (1×TAE) and PCR products of the correct size (808 bp) were gel purified using a Qiaquick Gel Extraction Kit (Qiagen cat. no. 28704) and eluted in 50 µl of elution buffer. (Qiagen). The purified PCR product (Gateway-modified INSP052 EC domain) was then transferred to pDONR201 using BP clonase as follows: 5 µl of Gateway-modified INSP052 EC domain was incubated with 1.5 µl pDONR201 (0.1 µg/µl), 2 µl BP buffer and 1.5 µl of BP clonase enzyme mix (Invitrogen) at RT for 1 h. The reaction was stopped by addition of proteinase K (2 µg) and incubated at 37° C. for a further 10 min. An aliquot of this reaction (1 µl) was transformed into 20 µl of E. coli DH10B cells (diluted ⅕ in H$_2$O) by electroporation using a Biorad Gene Pulser. Electroporated cells were diluted by addition of 1 ml of SOC medium and incubated for 1 h at 37° C. Transformants were plated on LB-kanamycin plates and incubated overnight at 37° C. Plasmid mini prep DNA was isolated from 1-10 resultant colonies using a Qiaprep Turbo 9600 robotic system (Qiagen) and subjected to DNA sequencing with pENTR-F1 and pENTR-R1 sequencing primers using the BigDyeTerminator system (Applied Biosystems cat. no. 4390246) according to the manufacturer's instructions. Sequencing reactions were purified using Dye-Ex columns (Qiagen) or Montage SEQ 96 cleanup plates (Millipore cat. no. LSKS09624) then analyzed on an Applied Biosystems 3700 sequencer.

4. Subcloning of the INSP052 EC Domain ORF to Expression Vector pEAK12d

Plasmid eluate (1.5 µl) from a pDONR201 clone containing the correct sequence of the INSP052 EC domain (plasmid ID # 13497) was then used in a recombination reaction containing 1.5 µl pEAK12d (0.1 µg/µl), 2 µl LR buffer and 1.5 µl of LR clonase (Invitrogen) in a final volume of 10 µl. The mixture was incubated at RT for 1 h, stopped by addition of proteinase K (2 µg) and incubated at 37° C. for a further 10 min. An aliquot of this reaction (1 µl) was used to transform E. coli DH10B cells by electroporation as described above. Electroporated cells were diluted by addition of 1 ml of SOC medium and incubated for 1 h at 37° C. Transformants were plated on LB-ampicillin plates and incubated overnight at 37° C. Mini prep DNA was prepared from 4 colonies using a Qiaprep Turbo 9600 robotic system (Qiagen) and eluted in 50 µl of elution buffer. Two µl of each miniprep was then subjected to PCR in a total reaction volume of 50 µl containing 2 µl of 5 mM dNTPs, 6 µl of 10 µM pEAK12-F, 6 µl of 10 µM pEAK12-R, 5 µl of 10×AmpliTaq™ buffer and 0.5 µl AmpliTaq™ (Applied Biosystems cat. no. N808-0155). The cycling conditions were as follows: 94° C. for 2 min; 30 cycles of 94° C. for 30 sec, 55° C. for 30 sec, and 72° C. for 1 min; 1 cycle, 72° C. for 3 min. Samples were then maintained at 4° C. (holding cycle) before further analysis.

Plasmid mini prep DNA was isolated from colonies which gave the expected PCR product size (1074 bp) was then subjected to DNA sequencing with pEAK12-F and pEAK12-R sequencing primers.

CsCl gradient purified maxi-prep DNA of plasmid pEAK12d-INSP052EC-6HIS (plasmid ID # 13495) was prepared from a 500 ml culture of a sequence verified clone (Sambrook J. et al., in Molecular Cloning, a Laboratory Manual, 2$^{nd}$ edition, 1989, Cold Spring Harbor Laboratory Press), resuspended at a concentration of 1 µg/µl in sterile water and stored at −20 C.

TABLE 2

Primers for INSP052 EC domain cloning and sequencing

| Primer | Sequence (5'-3') |
|---|---|
| GCP Forward | G GGG ACA AGT TTG TAC AAA AAA GCA GGC TTC GCC ACC |
| GCP Reverse | GGG GAC CAC TTT GTA CAA GAA AGC TGG GTT TCA ATG GTG ATG GTG ATG GTG |
| INSP052-B1P-exon1F | GCA GGC TTC GCC ACC ATG AAG AGA GAA AGG GGA GCC CTG TC |
| INSP052-exon1R | TCA CCC CCT CCA GGG GGT CTG TCT GGA TCA GAA GAA |
| INSP052-exon2F | TTC TTC TGA TCC AGA CAG ACC CCC TGG AGG GGG TGA |
| INSP052-exon2R | GTG GCC TCG AAA TGG GCA CAT CTA CAG TAA GGT TGA |
| INSP052-exon3F | CAA CCT TAC TGT AGA TGT GCC CAT TTC GAG GCC ACA |
| INSP052-exon3R | GGA GCT TCT TCT GTA TAC GGT GAT CTT GAC AG |
| INSP052-5HIS-R | GTG ATG GTG ATG GTG GGA GCT TCT TCT GTA TAC GG |
| pEAK12-F | GCC AGC TTG GCA CTT GAT GT |

TABLE 2-continued

Primers for INSP052 EC domain cloning and sequencing

| Primer | Sequence (5'-3') |
|---|---|
| pEAK12-R | GAT GGA GGT GGA CGT GTC AG |
| pENTR-F1 | TCG CGT TAA CGC TAG CAT GGA TCT C |
| pENTR-R1 | GTA ACA TCA GAG ATT TTG AGA CAC |

<u>Underlined</u> sequence = Kozak sequence
Bold = Stop codon
*Italic* sequence = His tag
<u><u>Doubleunderlined</u></u> = overlap with adjacent exon Example 3

Expression in Mammalian Cells of the Cloned, His-tagged INSP052-6His-V1 (Plasmid No. 13495)

Human Embryonic Kidney 293 cells expressing the Epstein-Barr virus Nuclear Antigen (HEK293-EBNA, Invitrogen) were maintained in suspension in Ex-cell VPRO serum-free medium (seed stock, maintenance medium, JRH). Sixteen to 20 hours prior to transfection (Day-1), cells were seeded in 2×T225 flasks (50 ml per flask in DMEM/F12 (1:1) containing 2% FBS seeding medium (JRH) at a density of $2 \times 10^5$ cells/ml). The next day (transfection d a y 0) the transfection took place by using the JetPEI™ reagent (2 µl/µg of plasmid DNA, PolyPlus-transfection). For each flask, 113 µg of cDNA (plasmid No. 13495) was co-transfected with 2.3 µg of GFP (fluorescent reporter gene). The transfection mix was then added to the 2×T225 flasks and incubated at 37° C. (5% $CO_2$) for 6 days. In order to increase our chances to get more material, we repeated this procedure into two extra flasks such as to generate 200 ml total. Confirmation of positive transfection was done by qualitative fluorescence examination at day 1 and day 6 (Axiovert 10 Zeiss).

On day 6 (harvest day), supernatants (200 ml) from the four flasks were pooled and centrifuged (4° C., 400 g) and placed into a pot bearing a unique identifier.

One aliquot (500 ul) was kept for QC of the 6His-tagged protein (internal bioprocessing QC).

Purification Process

The 200 ml culture medium sample containing the recombinant protein with a C-terminal 6His tag was diluted to a final volume of 200 ml with cold buffer A (50 mM $NaH_2PO_4$; 600 mM NaCl; 8.7% (w/v) glycerol, pH 7.5). The sample was filtered through a 0.22 um sterile filter (Millipore, 500 ml filter unit) and kept at 4° C. in a 250 ml sterile square media bottle (Nalgene).

The purification was performed at 4° C. on the VISION workstation (Applied Biosystems) connected to an automatic sample loader (Labomatic). The purification procedure was composed of two sequential steps, metal affinity chromatography on a Poros 20 MC (Applied Biosystems) column charged with Ni ions (4.6×50 mm, 0.83 ml), followed by gel filtration on a Sephadex G-25 medium (Amersham Pharmacia) column (1,0×10 cm).

For the first chromatography step the metal affinity column was regenerated with 30 column volumes of EDTA solution (100 mM EDTA; 1 M NaCl; pH 8.0), recharged with Ni ions through washing with 15 column volumes of a 100 mM $NiSO_4$ solution, washed with 10 column volumes of buffer A, followed by 7 column volumes of buffer B (50 mM $NaH_2PO_4$; 600 mM NaCl; 8.7% (w/v) glycerol, 400 mM; imidazole, pH 7.5), and finally equilibrated with 15 column volumes of buffer A containing 15 mM imidazole. The sample was transferred, by the Labomatic sample loader, into a 200 ml sample loop and subsequently charged onto the Ni metal affinity column at a flow rate of 10 ml/min. The column was washed with 12 column volumes of buffer A, followed by 28 column volumes of buffer A containing 20 mM imidazole. During the 20 mM imidazole wash loosely attached contaminating proteins were elution of the column. The recombinant His-tagged protein was finally eluted with 10 column volumes of buffer B at a flow rate of 2 ml/min, and the eluted protein was collected in a 1.6 ml fraction.

For the second chromatography step, the Sephadex G-25 gel-filtration column was regenerated with 2 ml of buffer D (1.137 M NaCl; 2.7 mM KCl; 1.5 mM $KH_2PO_4$; 8 mM $Na_2HPO_4$; pH 7.2), and subsequently equilibrated with 4 column volumes of buffer C (137 mM NaCl; 2.7 mM KCl; 1.5 mM $KH_2PO_4$; 8 mM $Na_2HPO_4$; 20% (w/v) glycerol; pH 7.4). The peak fraction eluted from the Ni-column was automatically through the integrated sample loader on the VISION loaded onto the Sephadex G-25 column and the protein was eluted with buffer C at a flow rate of 2 ml/min. The desalted sample was recovered in a 2.2 ml fraction. The fraction was filtered through a 0.22 um sterile centrifugation filter (Millipore), frozen and stored at −80C. An aliquot of the sample was analyzed on SDS-PAGE (4-12% NuPAGE gel; Novex) by coomassie staining and Western blot with anti-His antibodies.

Coomassie staining. The NuPAGE gel was stained in a 0.1% coomassie blue R250 staining solution (30% methanol, 10% acetic acid) at room temperature for 1 h and subsequently destained in 20% methanol, 7.5% acetic acid until the background was clear and the protein bands clearly visible.

Western blot. Following the electrophoresis the proteins were electrotransferred from the gel to a nitrocellulose membrane at 290 mA for 1 hour at 4° C. The membrane was blocked with 5% milk powder in buffer E (137 mM NaCl; 2.7 mM KCl; 1.5 mM $KH_2PO_4$; 8 mM $Na_2HPO_4$; 0.1% Tween 20, pH 7.4) for 1 h at room temperature, and subsequently incubated with a mixture of 2 rabbit polyclonal anti-His antibodies (G-18 and H-15; 0.2 ug/ml each; Santa Cruz) in 2.5% milk powder in buffer E overnight at 4° C. After further 1 hour incubation at room temperature, the membrane was washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane was developed with the ECL kit (Amersham Pharmacia) for 1 min. The membrane was subsequently exposed to a Hyperfilm (Amersham Pharmacia), the film developed and the western blot image visually analyzed.

Protein assay. The protein concentration was determined using the BCA protein assay kit (Pierce) with bovine serum albumin as standard. 890 µg purified protein was recovered from the 200 ml culture medium.

Example 4

Cytokine Expression Modulation Assays 4.1 Introduction: The following in vitro cell-based assays measure the effects of INSP052EC (cloned extracellular domain of INSP052, see Examples 2 and 3) on cytokine secretion induced by four different stimuli on different human peripheral blood mononuclear cells (hPBMC) cells, as measured by a cytokine bead array (CBA) assay for IL-2, IFN-γ, TNF-α, IL-5, IL-4 and IL-10. Four different stimuli, Lipopolysaccharide (LPS), phytohemmagglutinin (PHA), Concanavalin A (Con A) and toxic shock syndrome toxin-1 (TSST-1), were used at 3 different concentrations for each at 3 different time points -24, 48 and 72 hours.

The best conditions are 100 000 cells/well in 96-well plates and 100 µl final in 2% glycerol. The optimal concentration of mitogens are 0.1 ng/ml for LPS, 1 ng/ml for PHA, 5 ng/ml for ConA and 0.1 ng/ml for TSST-1. The optimal time for the assay is 48 h. The optimal concentration of the inhibitor, dexamethasone is 10-6 M. The optimal concentration of the stimulator, hIL-18 is 100 ng/ml.

The read-out choice is the CBA.

4.4.1 Purification of Human PBMC From a Buffy Coat

The buffy coat was diluted 1 to 2 with DMEM. 25 ml of diluted blood was thereafter slowly added onto a 15 ml layer of Ficoll in a 50 ml Falcon tube, and tubes were centrifuged (2000 rpm, 20 min, at RT without brake). The interphase (ring) was then collected and the cells were washed with 25 ml of DMEM followed by a centrifuge step (1200 rpm, 5 min). This procedure was repeated three times. A buffy coat gave approximately 600×10$^6$ total cells.

4.4.2 Screening

80 µl of 1.25×10$^6$ cells/ml were diluted in DMEM+2.5% Human Serum+1% L-Glutamine+1% Penicillin-Streptomycin and thereafter added to a 96 well microtiter plate.

10 µl were added per well (one condition per well): Proteins were diluted in PBS+20% Glycerol (the final dilution of the proteins is ¹/₁₀).

10 µl of the 4 stimuli were then added per well (one condition per well):
ConA 50 µg/ml. (the final concentration of ConA is 5 µg/ml)
LPS 1 µg/ml (the final concentration of LPS is 0.1 µg/ml)
PHA 10 µg/ml (the final concentration of PHA is 1 µg/ml)
TSST-1 1 µg/ml (the final concentration of TSST-1 is 0.1 µg/ml)

After 48 h, cell supernatants were collected and human cytokines were measured by Human Th1/Th2 Cytokine CBA Kit Becton-Dickinson.

For further clarification the Table below shows the experimental design.

| | 1 | 2 | 3 | 4 | 5 | 6 | 7 | 8 | 9 | 10 | 11 | 12 |
|---|---|---|---|---|---|---|---|---|---|---|---|---|
| A | Medium | Prot + STIM | Prot + STIM | Prot + STIM | Prot + STIM | Prot + STIM | Prot + STIM | Prot + STIM | Prot + STIM | Prot + STIM | Prot + STIM | Medium |
| B | Medium | Prot + STIM | Prot + STIM | Prot + STIM | Prot + STIM | Prot + STIM | Prot + STIM | Prot + STIM | Prot + STIM | Prot + STIM | Prot + STIM | ConA 5 µg/ml |
| C | STIM | Prot + STIM | Prot + STIM | Prot + STIM | Prot + STIM | Prot + STIM | Prot + STIM | Prot + STIM | Prot + STIM | Prot + STIM | Prot + STIM | ConA 5 µg/ml |
| D | STIM | Prot + STIM | Prot + STIM | Prot + STIM | Prot + STIM | Prot + STIM | Prot + STIM | Prot + STIM | Prot + STIM | Prot + STIM | Prot + STIM | ConA 5 µg/ml |
| E | STIM | Prot + STIM | Prot + STIM | Prot + STIM | Prot + STIM | Prot + STIM | Prot + STIM | Prot + STIM | Prot + STIM | Prot + STIM | Prot + STIM | ConA 5 µg/ml |
| F | STIM + dexa 10-6 M | Prot + STIM | Prot + STIM | Prot + STIM | Prot + STIM | Prot + STIM | Prot + STIM | Prot + STIM | Prot + STIM | Prot + STIM | Prot + STIM | STIM + IL-18 100 ng/ml |
| G | STIM + dexa 10-6 M | Prot + STIM | Prot + STIM | Prot + STIM | Prot + STIM | Prot + STIM | Prot + STIM | Prot + STIM | Prot + STIM | Prot + STIM | Prot + STIM | STIM + IL-18 100 ng/ml |
| H | STIM + dexa 10-6 M | Prot + STIM | Prot + STIM | Prot + STIM | Prot + STIM | Prot + STIM | Prot + STIM | Prot + STIM | Prot + STIM | Prot + STIM | Prot + STIM | STIM + IL-18 100 ng/ml |

4.4.3 CBA Analysis i) Preparation of Mixed Human Th1/Th2 Capture Beads

The number of assay tubes that were required for the experiment was determined.

Each capture bead suspension was vigorously vortexed for a few seconds before mixing. For each assay to be analysed, 10 µl aliquot of each capture bead were added into a single tube labelled "mixed capture beads". The Bead mixture was thoroughly vortexed.

ii) Preparation of Test Samples

Supernatants were diluted (1:4) using the Assay Diluent (20 µl of supernatants +60 µl of Assay Diluent). The sample dilution was then mixed before transferring samples into a 96 wells microtiter plate conical bottom (Nunc).

iii) Human Th1/Th2 Cytokine CBA Assay Procedure

50 µl of the diluted supernatants were added into a 96 wells microtiter plate conical bottom (Nunc). 50 µl of the mixed capture beads were added followed by 50 µl addition of the Human Th1/Th2 PE Detection Reagent. The plate was then incubated for 3 hours at RT and protected from direct exposure to light followed by centrifugation at 1500 rpm for 5 minutes. The supernatant was then carefully discarded. In a subsequent step, 200 μl of wash buffer were twice added to each well, centrifuged at 1500 rpm for 5 minutes and supernatant carefully discarded. 130 μl of wash buffer were thereafter added to each well to resuspend the bead pellet. The samples were finally analysed on a flow cytometer. The data were analysed using the CBA Application Software, Activity Base and Microsoft Excel software.

4.5 Results

Figure 12:
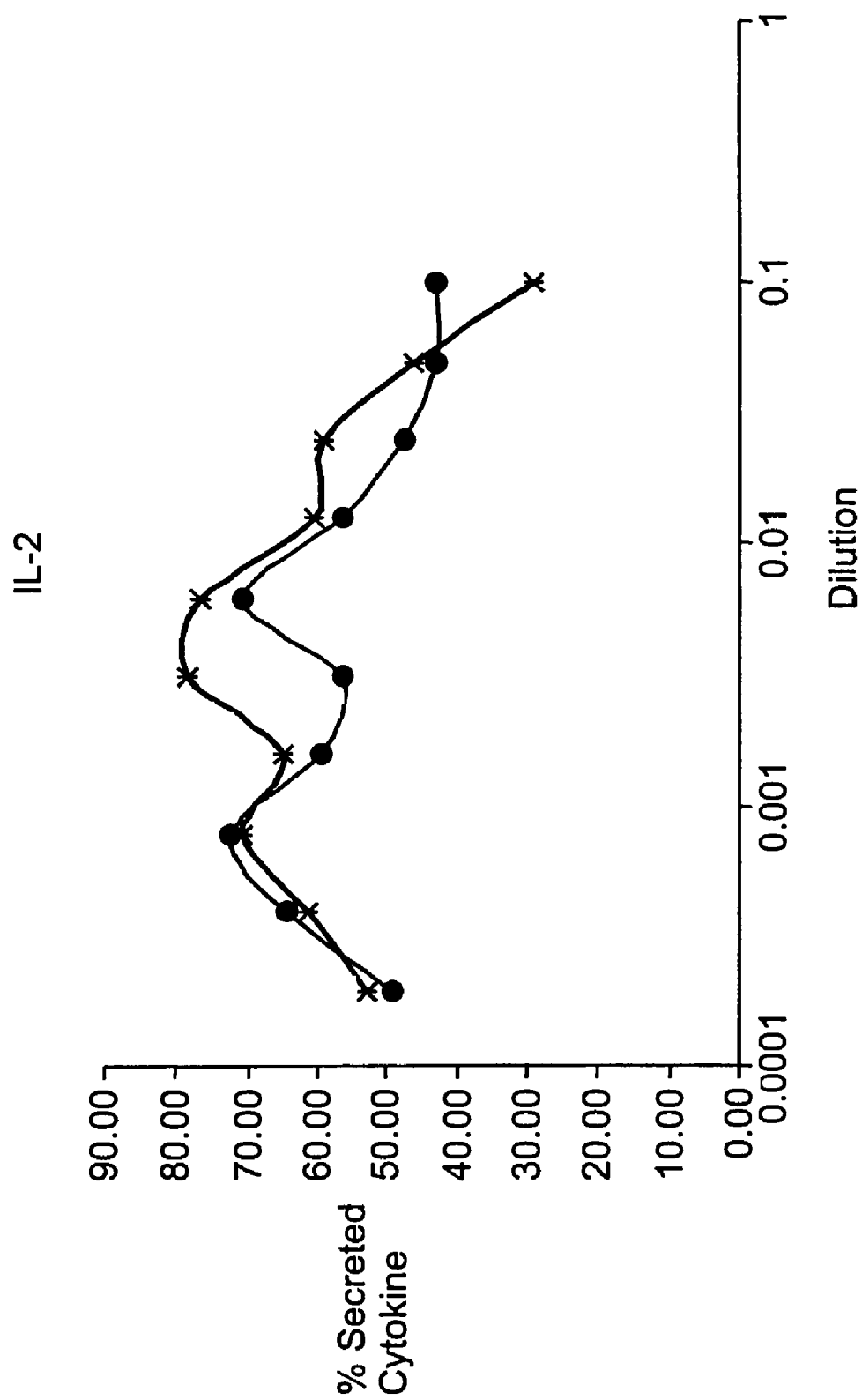
FIG. 12: % secreted IL-2 (see Example 4)

As shown in FIGS. 10, 11 and 12, INSP052EC was able to down-regulate in a dose-dependent manner the cytokine (TNF-alpha, IL-4 and IL-2) secretion from ConA-stimulated hPBMC. In the FIGS. 10 to 12 two different lots of the protein were tested. These results confirm a potential therapeutic efficacy of INSP052EC in the treatment of anti-inflammatory and auto-immune diseases.

Example 5

Mouse Model of Fulminant Liver Hepatitis 5.1 Introduction

Since INSP052EC protein has been shown in vitro to inhibit secretion of certain cytokines by ConA-stimulated human peripheral blood mononuclear cells (hPBMC) (see Example 4), it has been decided to test the activity of INSP052EC in the in vivo ConA model by electrotransfer.

5.2 Background—Concanavalin A (ConA)-Induced Liver Hepatitis

Toxic liver disease represents a worldwide health problem in humans for which pharmacological treatments have yet to be discovered. For instance active chronic hepatitis leading to liver cirrhosis is a disease state, in which liver parenchymal cells are progressively destroyed by activated T cells. ConA-induced liver toxicity is one of three experimental models of T-cell dependent apoptotic and necrotic liver injury described in mice. Gal N (D-Galactosamine) sensitized mice challenged with either activating anti-CD3 monoclonal AB or with superantigen SEB develop severe apoptotic and secondary necrotic liver injury (Kusters S, Gastroenterology. 1996 August;111(2):462-71). Injection of the T-cell mitogenic plant lectin ConA to non sensitized mice results also in hepatic apoptosis that preceeds necrosis. ConA induces the release of systemic TNF-alpha and IFN-gamma and various other cytokines. Both TNF-alpha and IFN-gamma are critical mediators of liver injury. Transaminase release 8 hours after the insult indicates severe liver destruction.

Several cell types have been shown to be involved in liver damage, CD4 T cells, macrophages and natural killer cells (Kaneko J Exp Med 2000, 191, 105-114). Anti-CD4 antibodies block activation of T cells and consequently liver damage (Tiegs et al. 1992, J Clin Invest 90, 196-203). Pre-treatment of mice with monoclonal antibodies against CD8 failed to protect, whereas deletion of macrophages prevented the induction of hepatitis.

The present study was undertaken to investigate the role of INSP052EC, a TNF-alpha antagonist protein containing IgG-like domains, in ConA-induced liver hepatitis. Several cytokines have been shown either to be critical in inducing or in conferring protection from ConA-induced liver damage. TNF-alpha for example is one of the first cytokines produced after ConA injection and anti-TNF-alpha antibodies confer protection against disease (Seino et al. 2001, Annals of surgery 234, 681). IFN-gamma appears also to be a critical mediator of liver injury, since anti-IFN-gamma antiserum significantly protect mice, as measured by decreased levels of transaminases in the blood of ConA-treated animals (see Kusters et al., above). In liver injury, increased production of IFN-gamma was observed in patients with autoimmune or viral hepatitis. In addition transgenic mice expressing IFN-gamma in the liver develop liver injury resembling chronic active hepatitis (Toyonaga et al. 1994, PNAS 91, 614-618). IFN-gamma may also be cytotoxic to hepatocytes, since in vitro IFN-gamma induces cell death in mouse hepatocytes that was accelerated by TNF (Morita et al. 1995, Hepatology 21, 1585-1593).

Other molecules have been described to be protective in the ConA model. A single administration of rhIL-6 completely inhibited the release of transaminases (Mizuhara et al. 1994, J. Exp. Med. 179, 1529-1537).

5.3 cDNA Electrotransfer Into Muscle Fibers in Order to Achieve Systemic Expression of a Protein of Interest Among the non-viral techniques for gene transfer in vivo, the direct injection of plasmid DNA into the muscle and subsequent electroporation is simple, inexpensive and safe. The post-mitotic nature and longevity of myofibers permits stable expression of transfected genes, although the transfected DNA does not usually undergo chromosomal integration (Somiari et al. 2000, Molecular Therapy 2,178). Several reports have demonstrated that secretion of muscle-produced proteins into the blood stream can be achieved after electroporation of corresponding cDNAs (Rizzuto et al. PNAS, 1996, 6417; Aihara H et al., 1998, Nature Biotech 16, 867). In addition in vivo efficacy of muscle expressed Epo and IL-18BP in disease models has been shown (Rizzuto, 2000, Human Gene Therapy 41, 1891; Mallat, 2001, Circulation research 89, 41).

5.4 Materials and Methods 5.4.1 Animals

In all the studies male C57/BL6 male (8 weeks of age) were used. In general, 7 animals per experimental group are used. Mice were maintained in standard conditions under a 12-hour light-dark cycle, provided irradiated food and water ad libitum.

5.4.2 Muscle Electrotransfer 5.4.2.1 Choice of Vector

His or StrepII tagged IL6 and INSP052 genes were cloned in the Gateway compatible pDEST12.2 vector containing the CMV promoter.

5.4.2.2 Electroporation Protocol

Mice were anesthetized with gas (isofluran Baxter, Ref: ZDG9623). Hindlimbs were shaved and an echo graphic gel was applied. Hyaluronidase was injected in the posterior tibialis mucle with (20U in 50 μl sterile NaCl 0.9%, Sigma Ref. H3631). After 10 min, 100 μg of plasmid (50 μg per leg in 25 μl of sterile NaCl 0.9%) was injected in the same muscle. The DNA was prepared in the Buffer PBS-L-Glutamate (6 mg/ml; L-Glutamate Sigma P4761) before intramuscular injection. For electrotransfer, the electric field was applied for each leg with the ElectroSquarePorator BTX ref ECM830 at 75 Volts during 20 ms for each pulse, 10 pulses with an interval of 1 second in a unipolar way with 2 round electrodes (size 0.5 mm diameter).

5.4.3 The ConA Model 5.4.3.1 ConA i.v. Injection and Blood Sampling 8 weeks old Female Mice C57/B16 were purchased from IFFA CREDO . ConA (Sigma ref.C7275) was injected at 18 mg/kg iv. and blood samples were taken at 1.30 and 8 hours postinjection. At the time of sacrifice, blood was taken from the heart.

5.4.3.2 Detection of Cytokines and Transaminases in Blood Samples

IL2, IL5, IL4, TNF-alpha and IFN-gamma cytokine levels were measured using the TH1/TH2 CBA assay. TNF-alpha, IL-6, MCP1, IFN-alpha, IL-10 and IL-12 were detected using the Inflammation CBA assay. Transaminase blood parameters were determined using the COBAS instrument (Hitachi).

5.4.3.3 INSP052EC and IL-6 Electrotransfer

At day 0 electrotransfer of pDEST12.2.—INSP052EC, pDEST12.2-hIL-6 as well as and the empty vector control (electrotransfer protocol see above) was performed. At day 5 after electrotransfer, ConA (18 mg/kg) was injected i.v. and blood sampled at 2 time points (1.30, 8 hours). Cytokine and ASAT ALAT measurements were performed like described above).

5.4.3.4 INSP052 and IL6 Protein Pretreatment in the ConA Model

CHO cell produced hIL-6 and HEK293 cell produced INSP052 was injected 30 min before ConA injection.

5.5 Results

We have shown previously (see Example 4 and FIGS. 10-12) that HEK 293 cell expressed INSP052EC protein down-regulates TNF-alpha and IL-4 cytokine secretion in ConA and TSST-1 stimulated hPBMC in vitro in a dose dependent way. Since these two cytokines play a crucial role in T cell induced ConA induced liver hepatitis, we tested INSP052EC cDNA and protein in this model.

Figure 13A:
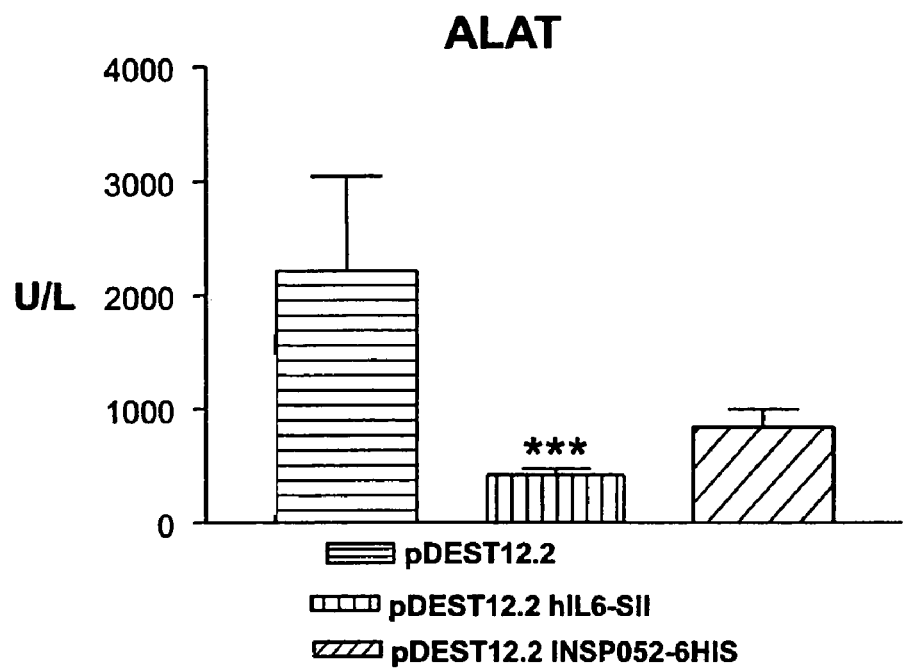
FIGS. 13A and 13B show that INSP052EC-eletrotransferred animals show a decrease in transaminase levels as compared to empty vector control animals 8 hours after the ConA challenge. (see Example 5)
Figure 13B:
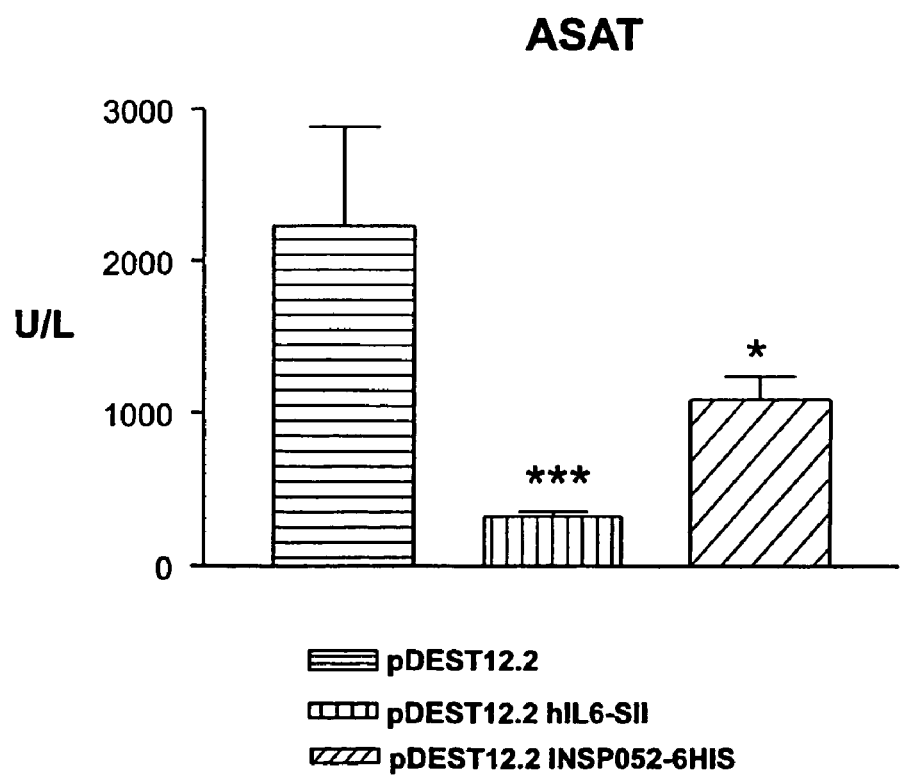
Figure 14A:
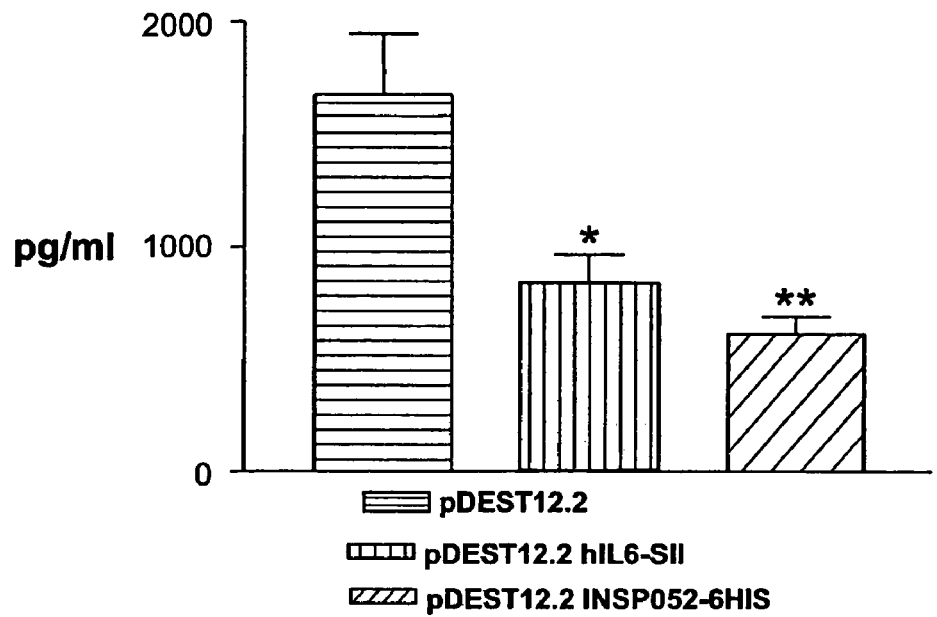
FIG. 14: TNF-alpha and IL-6 cytokine levels in INSP052EC-eletrotransferred animals (see Example 5)
Figure 14B:
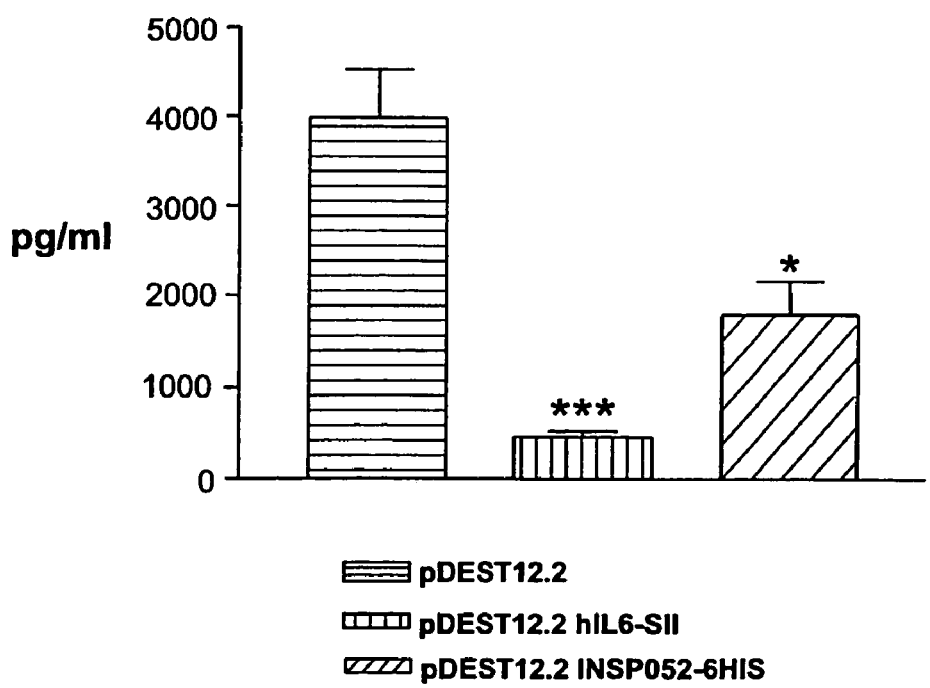

We have now found that INSP052EC protects from liver injury in a mouse model mimicking fulminant hepatitis after systemic delivery of the protein using electrotransfer. FIGS. 13A and 13B show that INSP052EC-eletrotransferred animals show a decrease in transaminases levels as compared to empty vector control animals 8 hours after the ConA challenge. In addition both TNF-alpha and IL-6 cytokine levels are significantly reduced in these animals (FIGS. 14A and 14B). Please note that the effect is similar to that obtained with the positive control vector pDEST12.2hIL-6-SII (FIGS. 14A and 14B).

Figure 15A:
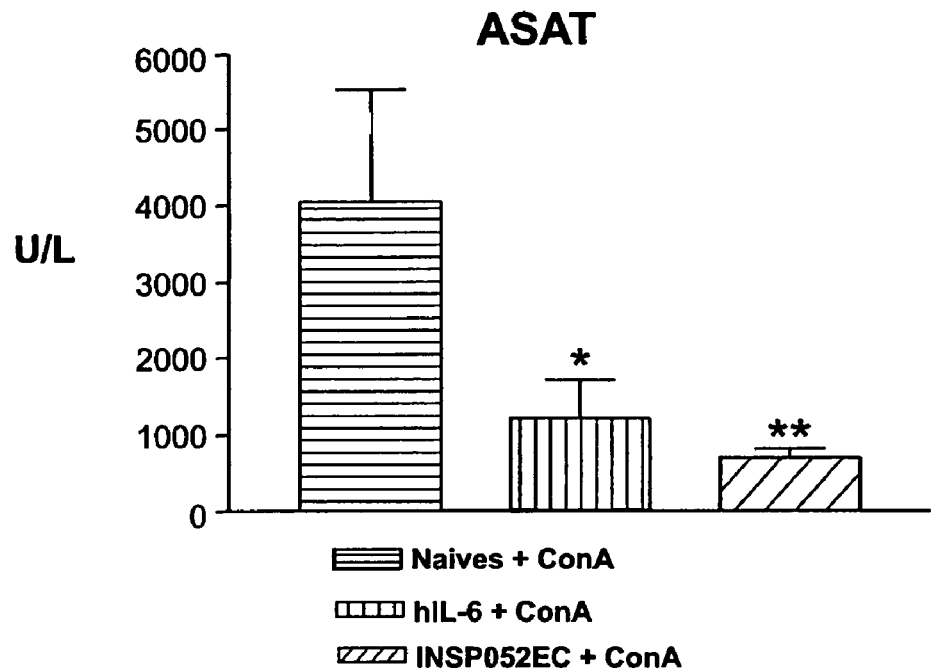
FIG. 15: ASAT and ALAT levels after 8 hours (see Example 5)
Figure 15B:
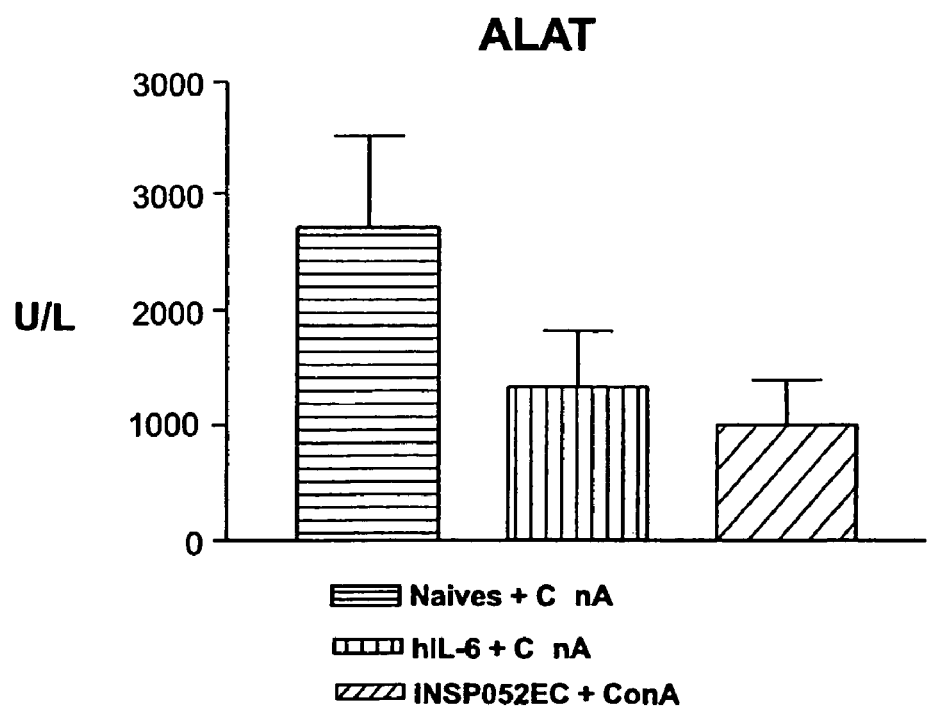
Figure 15C:
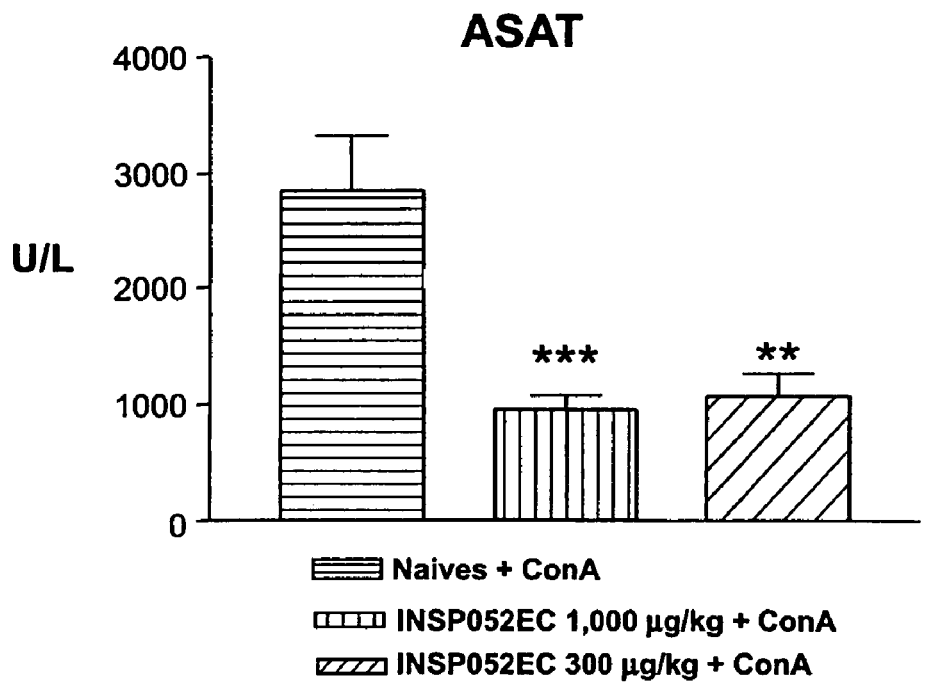
Figure 15D:
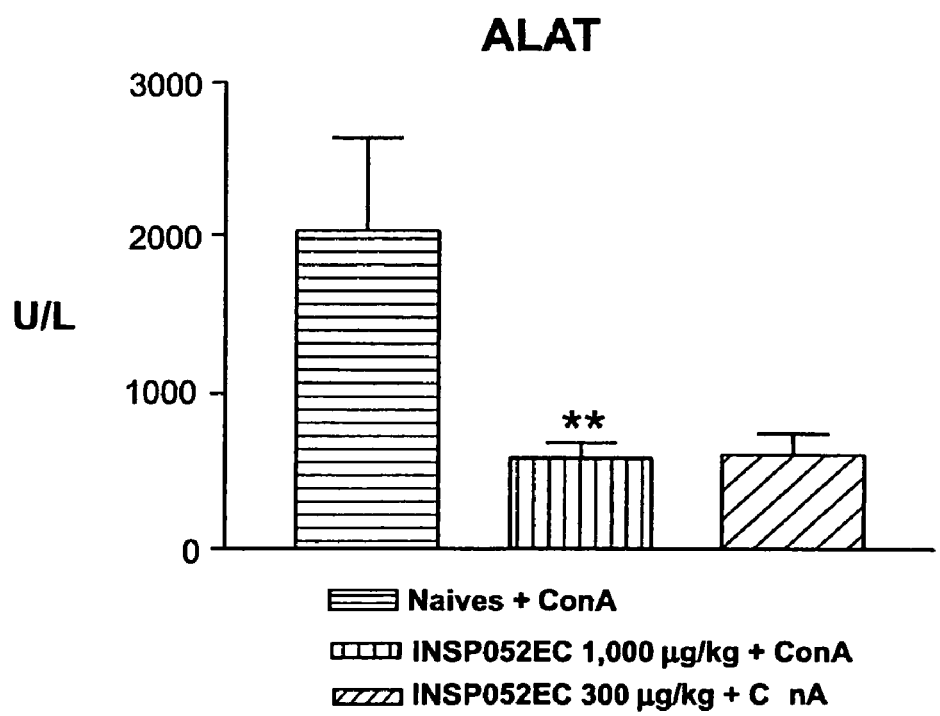

In addition s.c. injected INSP052EC protein (1 mg/kg, 0.3 mg/kg) decreased ASAT and ALAT levels 8 hours after ConA injection (FIGS. 15C and 15D).

5.6 Conclusion

Our experiments have already shown, that INSP052EC downregulates TNF-alpha, IL-4 and IL-2 secretion in vitro in the ConA stimulated hPBMC assay. In addition we could show that delivery of INSP052EC cDNA in an in vivo model of fulminant hepatitis decreases TNF-alpha and m-IL-6 levels in serum and had a significant effect on the reduction of transaminases measured in serum, which was confirmed by s.c. INSP052EC protein injections.

The decrease in ASAT ALAT levels might be due to both, decreased TNF-alpha and IL-4 levels. TNF-alpha and IL-4 are important cytokines involved in the liver damage after ConA injection. In this mouse model of liver hepatitis TNF-alpha is mainly produced by hepatic macrophages, the so-called Kupfer cells, whereas IL-4 is produced by liver (natural killer T) NKT cells. Anti TNF-alpha antibodies confer protection against disease (Seino et al. 2001, Annals of surgery 234, 681) and inhibition of IL-4 production by NKT cells was shown to be hepato-protective in T-cell mediated hepatitis in mouse (Ajuebor et al. 2003 J. Immunology 170, 5252-9).

INSP052EC might be useful in treating auto-immune, viral or acute liver diseases as well as alcoholic liver failures. It might be also effective in other inflammatory diseases.

The invention will now be described by the following numbered paragraphs:

1. A polypeptide, which polypeptide:
   (i) comprises or consists of the amino acid sequence as recited in SEQ ID NO: 16 or SEQ ID NO:26;
   (ii) is a fragment thereof having the activity of a polypeptide according to (i), or having an antigenic determinant in common with a polypeptide according to (i); or
   (iii) is a functional equivalent of (i) or (ii).
2. A polypeptide according to paragraph 1 part ii) which comprises or consists of the amino acid sequence as recited in SEQ ID NO:20 or in SEQ ID NO:22.
3. A polypeptide which is a functional equivalent according to paragraph 1 (iii), characterised in that it is homologous to the amino acid sequence as recited in SEQ ID NO: 16 or SEQ ID NO:26 and has activity as an antagonist of cytokine expression and/or secretion.
4. A purified nucleic acid molecule which encodes a polypeptide according to any one of the preceding paragraphs.
5. A purified nucleic acid molecule according to paragraph 4, which comprises the nucleic acid sequence as recited in SEQ ID NO:15, SEQ ID NO:19, SEQ ID NO:21, SEQ ID NO:25, or is a redundant equivalent or fragment thereof.
6. A purified nucleic acid molecule according to paragraph 5 which consists of the nucleic acid sequence as recited in SEQ ID NO:15, SEQ ID NO:19, SEQ ID NO:21 or SEQ ID NO:25.
7. A purified nucleic acid molecule which hybridizes under high stringency conditions with a nucleic acid molecule according to any one of paragraphs 4 to 6.
8. A vector comprising a nucleic acid molecule as recited in any one of paragraphs 4 to 7.
9. A host cell transformed with a vector according to paragraph 8.
10. A ligand which binds specifically to, and which preferably inhibits the activity of a polypeptide according to any one of paragraphs 1 to 3.
11. A ligand according to paragraph 10, which is an antibody.
12. A compound that either increases or decreases the level of expression or activity of a polypeptide according to any one of paragraphs 1 to 3.
13. A compound according to paragraph 12 that binds to a polypeptide according to any one of paragraphs 1 to 3 without inducing any of the biological effects of the polypeptide.
14. A compound according to paragraph 13, which is a natural or modified substrate, ligand, enzyme, receptor or structural or functional mimetic.
15. A polypeptide according to any one of paragraphs 1 to 3, a nucleic acid molecule according to any one of paragraphs 4 to 7, a vector according to paragraph 8, a host cell according to paragraph 9, a ligand according to paragraph 10 or paragraph 11, or a compound according to any one of paragraphs 12 to 14, for use in therapy or diagnosis of disease.
16. A method of diagnosing a disease in a patient, comprising assessing the level of expression of a natural gene encoding a polypeptide according to any one of paragraphs 1 to 3, or assessing the activity of a polypeptide according to any one of paragraphs 1 to 3, in tissue from said patient and comparing said level of expression or activity to a control level, wherein a level that is different to said control level is indicative of disease.

17. A method according to paragraph 16 that is carried out in vitro.

18. A method according to paragraph 16 or paragraph 17, which comprises the steps of: (a) contacting a ligand according to paragraph 10 or paragraph 11 with a biological sample under conditions suitable for the formation of a ligand-polypeptide complex; and (b) detecting said complex.

19. A method according to paragraph 16 or paragraph 17, comprising the steps of:
   a) contacting a sample of tissue from the patient with a nucleic acid probe under stringent conditions that allow the formation of a hybrid complex between a nucleic acid molecule according to any one of paragraphs 4 to 7 and the probe;
   b) contacting a control sample with said probe under the same conditions used in step a); and
   c) detecting the presence of hybrid complexes in said samples; wherein detection of levels of the hybrid complex in the patient sample that differ from levels of the hybrid complex in the control sample is indicative of disease.

20. A method according to paragraph 17 or paragraph 18, comprising:
   a. contacting a sample of nucleic acid from tissue of the patient with a nucleic acid primer under stringent conditions that allow the formation of a hybrid complex between a nucleic acid molecule according to any one of paragraphs 4 to 7 and the primer;
   b. contacting a control sample with said primer under the same conditions used in step a); and
   c. amplifying the sampled nucleic acid; and
   d. detecting the level of amplified nucleic acid from both patient and control samples; wherein detection of levels of the amplified nucleic acid in the patient sample that differ significantly from levels of the amplified nucleic acid in the control sample is indicative of disease.

21. A method according to paragraph 17 or paragraph 18 comprising:
   a. obtaining a tissue sample from a patient being tested for disease;
   b. isolating a nucleic acid molecule according to any one of paragraphs 4 to 7 from said tissue sample; and
   c. diagnosing the patient for disease by detecting the presence of a mutation which is associated with disease in the nucleic acid molecule as an indication of the disease.

22. The method of paragraph 21, further comprising amplifying the nucleic acid molecule to form an amplified product and detecting the presence or absence of a mutation in the amplified product.

23. The method of paragraph 21 or paragraph 22, wherein the presence or absence of the mutation in the patient is detected by contacting said nucleic acid molecule with a nucleic acid probe that hybridises to said nucleic acid molecule under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation.

24. A method according to any one of paragraphs 16 to 23, wherein said disease is an auto-immune, viral or acute liver disease, including alcoholic liver failure, or inflammatory disease.

25. Use of a polypeptide according to any one of paragraphs 1 to 3 as an antagonist of cytokine expression and/or secretion.

26. A pharmaceutical composition comprising a polypeptide according to any one of paragraphs 1 to 3, a nucleic acid molecule according to any one of paragraphs 4 to 7, a vector according to paragraph 8, a host cell according to paragraph 9, a ligand according to paragraph 10 or paragraph 11, or a compound according to any one of paragraphs 12 to 14.

27. A vaccine composition comprising a polypeptide according to any one of paragraphs 1 to 3 or a nucleic acid molecule according to any one of paragraphs 4 to 7.

28. Use of a polypeptide according to any one of paragraphs 1 to 3, a nucleic acid molecule according to any one of paragraphs 10 to 11, a vector according to paragraph 8, a host cell according to paragraph 9, a ligand according to paragraph 10 or paragraph 11, or a compound according to any one of paragraphs 12 to 14 or a pharmaceutical composition of paragraph 26, in the manufacture of a medicament for the treatment of an auto-immune disease, viral or acute liver disease, including alcoholic liver failure, or inflammatory disease.

29. A method of treating a disease in a patient, comprising administering to the patient a polypeptide according to any one of paragraphs 1 to 3, a nucleic acid molecule according to any one of paragraphs 4 to 7, a vector according to paragraph 8, a host cell according to paragraph 9, a ligand according to paragraph 10 or paragraph 11, or a compound according to any one of paragraphs 12 to 14 or a pharmaceutical composition of paragraph 30.

30. A method according to paragraph 29, wherein, for diseases in which the expression of the natural gene or the activity of the polypeptide is lower in a diseased patient when compared to the level of expression or activity in a healthy patient, the polypeptide, nucleic acid molecule, vector, ligand, compound or composition administered to the patient is an agonist.

31. A method according to paragraph 29, wherein, for diseases in which the expression of the natural gene or activity of the polypeptide is higher in a diseased patient when compared to the level of expression or activity in a healthy patient, the polypeptide, nucleic acid molecule, vector, ligand, compound or composition administered to the patient is an antagonist.

32. A method of monitoring the therapeutic treatment of disease in a patient, comprising monitoring over a period of time the level of expression or activity of a polypeptide according to any one of paragraphs 1 to 3, or the level of expression of a nucleic acid molecule according to any one of paragraphs 4 to 7 in tissue from said patient, wherein altering said level of expression or activity over the period of time towards a control level is indicative of regression of said disease.

33. A method for the identification of a compound that is effective in the treatment and/or diagnosis of disease, comprising contacting a polypeptide according to any one of paragraphs 1 to 3, or a nucleic acid molecule according to any one of paragraphs 4 to 7 with one or more compounds suspected of possessing binding affinity for said polypeptide or nucleic acid molecule, and selecting a compound that binds specifically to said nucleic acid molecule or polypeptide.

34. A kit useful for diagnosing disease comprising a first container containing a nucleic acid probe that hybridises under stringent conditions with a nucleic acid molecule according to any one of paragraphs 4 to 7; a second container containing primers useful for amplifying said nucleic acid molecule; and instructions for using the probe and primers for facilitating the diagnosis of disease.
35. The kit of paragraph 34, further comprising a third container holding an agent for digesting unhybridised RNA.
36. A kit comprising an array of nucleic acid molecules, at least one of which is a nucleic acid molecule according to any one of paragraphs 4 to 7.
37. A kit comprising one or more antibodies that bind to a polypeptide as recited in any one of paragraphs 1 to 7, and a reagent useful for the detection of a binding reaction between said antibody and said polypeptide.
38. A transgenic or knockout non-human animal that has been transformed to express higher, lower or absent levels of a polypeptide according to any one of paragraphs 1 to 3.
39. A method for screening for a compound effective to treat disease, by contacting a non-human transgenic animal according to paragraph 38 with a candidate compound and determining the effect of the compound on the disease of the animal.

Sequence Information

Note: for amino acids encoded by exon-exon junctions, the amino acid will be assigned to the more 5' exon.

```
SEQ ID NO 1: (INSP052 Nucleotide sequence exon1)
   1 ATGAAGAGAG AAAGGGGAGC CCTGTCCAGA GCCTCCAGGG CCCTGCGCCT TGCTCCTTTT

61 GTCTACCTTC TTCTGATCCA GACAG

SEQ ID NO 2: (INSP052 polypeptide sequence of Exon 1)
   1 MKRERGALSR ASRALRLAPF VYLLLIQTD SEQ Id NO 3: (INSP052 Nucleotide sequence exon2)
   1 ACCCCCTGGA GGGGGTGAAC ATCACCAGCC CCGTGCGCCT GATCCATGGC ACCGTGGGGA

61 AGTCGGCTCT GCTTTCTGTG CAGTACAGCA GTACCAGCAG CGACAGGCCT GTAGTGAAGT

121 GGCAGCTGAA GCGGGACAAG CCAGTGACCG TGGTGCAGTC CATTGGCACA GAGGTCATCG

181 GCACCCTGCG GCCTGACTAT CGAGACCGTA TCCGACTCTT TGAAAATGGC TCCCTGCTTC

241 TCAGCGACCT GCAGCTGGCC GATGAGGGCA CCTATGAGGT CGAGATCTCC ATCACCGACG

301 ACACCTTCAC TGGGGAGAAG ACCATCAACC TTACTGTAGA TG

SEQ ID NO 4: (INSP052 Protein Sequence of Exon 2)
   1 PLEGVNITSP VRLIHGTVGK SALLSVQYSS TSSDRPVVKW QLKRDKPVTV VQSIGTEVIG

61 TLRPDYRDRI RLFENGSLLL SDLQLADEGT YEVEISITDD TFTGEKTINL TVDV

SEQ ID NO 5: (INSP052 Nucleotide sequence Exon3)
   1 TGCCCATTTC GAGGCCACAG GTGTTGGTGG CTTCAACCAC TGTGCTGGAG CTCAGCGAGG

61 CCTTCACCTT GAACTGCTCA CATGAGAATG GCACCAAGCC CAGCTACACC TGGCTGAAGG

121 ATGGCAAGCC CCTCCTCAAT GACTCGAGAA TGCTCCTGTC CCCCGACCAA AAGGTGCTCA

181 CCATCACCCG CGTGCTCATG GAGGATGACG ACCTGTACAG CTGCATGGTG GAGAACCCCA

241 TCAGCCAGGG CCGCAGCCTG CCTGTCAAGA TCACCGTATA CA

SEQ ID NO 7: (INSP052 Polypeptide sequence of Exon 3)
   1 PISRPQVLVA STTVLELSEA FTLNCSHENG TKPSYTWLKD GKPLLNDSRM LLSPDQKVLT

61 ITRVLMEDDD LYSCMVENPI SQGRSLPVKI TVYR

SEQ ID NO 7: (INSP052 Nucleotide Sequence Exon 4)
   1 GAAGAAGCTC CCTTTACATC ATCTTGTCTA CAGGAGGCAT CTTCCTCCTT GTGACCTTGG

61 TGACAGTCTG TGCCTGCTGG AAACCCTCCA AAAG

SEQ ID NO 8: (INSP052 Polypeptide sequence of Exon 4)
   1 RSSLYIILST GGIFLLVTLV TVCACWKPSK R SEQ ID NO 9: (INSP052 Nucleotide Sequence Exon 5)
   1 GAAACAGAAG AAGCTAGAAA AGCAAAACTC CCTGGAATAC ATGGATCAGA ATGATGACCG

61 CCTGAAACCA GAAG

SEQ ID NO 10: (INSP052 Polypeptide Sequence Exon 5)
   1 KQKKLEKQNS LEYMDQNDDR LKPEA
```

-continued

SEQ ID NO 11: (INSP052 Nucleotide Sequence Exon 6)
```
  1 CAGACACCCT CCCTCGAAGT GGTGAGCAGG AACGGAAGAA CCCCATGGCA CTCTATATCC

61 TGAAGGACAA G
```

SEQ ID NO 12: (INSP052 Polypeptide Sequence Exon 6)
```
  1 DTLPRSGEQE RKNPMALYIL KDK
```

SEQ ID NO 13: (INSP052 Nucleotide Sequence Exon 7)
```
  1 GACTCCCCGG AGACCGAGGA GAACCCGGCC CCGGAGCCTC GAAGCGCGAC GGAGCCCGGC

61 CCGCCCGGCT ACTCCGTGTC TCCCGCCGTG CCCGGCCGCT CGCCGGGGCT GCCCATCCGC

121 TCTGCCCGCC GCTACCCGCG CTCCCCAGCG CGCTCCCCAG CCACCGGCCG GACACACTCG

181 TCGCCGCCCA GGGCCCCGAG CTCGCCCGGC CGCTCGCGCA GCGCCTCGCG CACACTGCGG

241 ACTGCGGGCG TGCACATAAT CCGCGAGCAA GACGAGGCCG GCCCGGTGGA GATCAGCGCC

301 TGA
```

SEQ ID NO 14: (INSP052 Polypeptide sequence for exon 7)
```
  1 DSPETEENPA PEPRSATEPG PPGYSVSPAV PGRSPGLPIR SARRYPRSPA RSPATGRTHS

61 SPPRAPSSPG RSRSASRTLR TAGVHIIREQ DEAGPVEISA
```

SEQ ID NO :15 (INSP052 Combined Nucleotide sequence
exons 1, 2, 3, 4, 5, 6 and 7)
```
   1 ATGAAGAGAG AAAGGGGAGC CCTGTCCAGA GCCTCCAGGG CCCTGCGCCT TGCTCCTTTT

61 GTCTACCTTC TTCTGATCCA GACAGACCCC CTGGAGGGGG TGAACATCAC CAGCCCCGTG

121 CGCCTGATCC ATGGCACCGT GGGGAAGTCG GCTCTGCTTT CTGTGCAGTA CAGCAGTACC

181 AGCAGCGACA GGCCTGTAGT GAAGTGGCAG CTGAAGCGGG ACAAGCCAGT GACCGTGGTG

241 CAGTCCATTG GCACAGAGGT CATCGGCACC CTGCGGCCTG ACTATCGAGA CCGTATCCGA

301 CTCTTTGAAA ATGGCTCCCT GCTTCTCAGC GACCTGCAGC TGGCCGATGA GGGCACCTAT

361 GAGGTCGAGA TCTCCATCAC CGACGACACC TTCACTGGGG AGAAGACCAT CAACCTTACT

421 GTAGATGTGC CCATTTCGAG GCCACAGGTG TTGGTGGCTT CAACCACTGT GCTGGAGCTC

481 AGCGAGGCCT TCACCTTGAA CTGCTCACAT GAGAATGGCA CCAAGCCCAG CTACACCTGG

541 CTGAAGGATG GCAAGCCCCT CCTCAATGAC TCGAGAATGC TCCTGTCCCC CGACCAAAAG

601 GTGCTCACCA TCACCCGCGT GCTCATGGAG GATGACGACC TGTACAGCTG CATGGTGGAG

661 AACCCCATCA GCCAGGGCCG CAGCCTGCCT GTCAAGATCA CCGTATACAG AAGAAGCTCC

721 CTTTACATCA TCTTGTCTAC AGGAGGCATC TTCCTCCTTG TGACCTTGGT GACAGTCTGT

781 GCCTGCTGGA AACCCTCCAA AGGAAACAG AAGAAGCTAG AAAAGCAAAA CTCCCTGGAA

841 TACATGGATC AGAATGATGA CCGCCTGAAA CCAGAAGCAG ACACCCTCCC TCGAAGTGGT

901 GAGCAGGAAC GGAAGAACCC CATGGCACTC TATATCCTGA AGGACAAGGA CTCCCCGGAG

961 ACCGAGGAGA ACCCGGCCCC GGAGCCTCGA AGCGCGACGG AGCCCGGCCC GCCCGGCTAC

1021 TCCGTGTCTC CCGCCGTGCC CGGCCGCTCG CCGGGGCTGC CCATCCGCTC TGCCCGCCGC

1081 TACCCGCGCT CCCCAGCGCG CTCCCCAGCC ACCGGCCGGA CACACTCGTC GCCGCCCAGG

1141 GCCCCGAGCT CGCCCGGCCG CTCGCGCAGC GCCTCGCGCA CACTGCGGAC TGCGGGCGTG

1201 CACATAATCC GCGAGCAAGA CGAGGCCGGC CCGGTGGAGA TCAGCGCCTG A
```

SEQ ID NO:16 (INSP052 Combined polypeptide sequence for
exons 1, 2, 3, 4, 5, 6 and 7.)
```
  1 MKRERGALSR ASRALRLAPF VYLLLIQTDP LEGVNITSPV RLIHGTVGKS ALLSVQYSST

61 SSDRPVVKWQ LKRDKPVTVV QSIGTEVIGT LRPDYRDRIR LFENGSLLLS DLQLADEGTY

121 EVEISITDDT FTGEKTINLT VDVPISRPQV LVASTTVLEL SEAFTLNCSH ENGTKPSYTW

181 LKDGKPLLND SRMLLSPDQK VLTITRVLME DDDLYSCMVE NPISQGRSLP VKITVYRRSS
```

```
241 LYIILSTGGI FLLVTLVTVC ACWKPSKRKQ KKLEKQNSLE YMDQNDDRLK PEADTLPRSG

301 EQERKNPMAL YILKDKDSPE TEENPAPEPR SATEPGPPGY SVSPAVPGRS PGLPIRSARR

361 YPRSPARSPA TGRTHSSPPR APSSPGRSRS ASRTLRTAGV HIIREQDEAG PVEISA
SEQ ID NO:17 (INSP055 Mouse virtual cDNA)
   1 ATGAAGAGAG AAAGGGGAGC CCTGTCAAGA GCCTCCAGGG CTCTGCGCCT CTCTCCTTTT

61 GTCTACCTGC TTCTCATCCA GCCAGTCCCC CTGGAGGGGG TGAACATCAC CAGCCCAGTA

121 CGTCTGATCC ACGGCACAGT GGGGAAGTCG GCCCTGCTTT CCGTGCAGTA CAGTAGCACC

181 AGCAGCGACA AGCCCGTGGT GAAGTGGCAG CTGAAGCGTG ACAAGCCAGT GACCGTGGTG

241 CAGTCTATAG GCACAGAGGT CATTGGCACT CTGCGGCCTG ACTATCGAGA CCGTATCCGG

301 CTCTTTGAAA ATGGCTCCTT GCTTCTCAGC GACCTGCAGC TGGCGGATGA GGGAACCTAT

361 GAAGTGGAGA TTTCCATCAC TGACGACACC TTCACCGGGG AGAAGACCAT CAACCTCACC

421 GTGGATGTGC CCATTTCAAG GCCGCAGGTA TTAGTGGCTT CAACCACTGT GCTGGAGCTC

481 AGTGAGGCCT TCACCCTCAA CTGCTCCCAT GAGAATGGCA CCAAGCCTAG CTACACGTGG

541 CTGAAGGATG GCAAACCCCT CCTCAATGAC TCCCGAATGC TCCTGTCCCC TGACCAAAAG

601 GTGCTCACCA TCACCCGAGT ACTCATGGAA GATGACGACC TGTACAGCTG TGTGGTGGAG

661 AACCCCATCA GCCAGGTCCG CAGCCTGCCT GTCAAGATCA CTGTGTATAG AAGAAGCTCC

721 CTCTATATCA TCTTGTCTAC AGGAGGCATC TTCCTCCTTG TGACCCTGGT GACAGTTTGT

781 GCCTGCTGGA AACCCTCAAA AAAGTCTAGG AAGAAGAGGA AGTTGGAGAA GCAAAACTCC

841 TTGGAATACA TGGATCAGAA TGATGACCGC CTAAAATCAG AAGCAGATAC CCTACCCCGA

901 AGTGGAGAAC AGGAGCGGAA GAACCCAATG GCACTCTATA TCCTGAAGGA TAAGGATTCC

961 TCAGAGCCAG ATGAAAACCC TGCTACAGAG CCACGGAGCA CCACAGAACC CGGTCCCCCT

1021 GGCTACTCCG TGTCGCCGCC CGTGCCCGGC CGCTCTCCGG GGCTTCCCAT CCGCTCAGCC

1081 CGCCGCTACC CGCGCTCCCC AGCACGTTCC CCTGCCACTG GCCGGACGCA CACGTCGCCA

1141 CCGCGGGCCC CGAGCTCGCC AGGCCGCTCG CGCAGCTCTT CGCGCTCACT GCGGACTGCA

1201 GGCGTGCAGA GAATCCGGGA GCAGGACGAG TCAGGGCAGG TGGAGATCAG TGCCTGA
SEQ ID NO:18 (INSP055 Mouse Predicted Protein)
   1 MKRERGALSR ASRALRLSPF VYLLLIQPVP LEGVNITSPV RLIHGTVGKS ALLSVQYSST

61 SSDKPVVKWQ LKRDKPVTVV QSIGTEVIGT LRPDYRDRIR LFENGSLLLS DLQLADEGTY

121 EVEISITDDT FTGEKTINLT VDVPISRPQV LVASTTVLEL SEAFTLNCSH ENGTKPSYTW

181 LKDGKPLLND SRMLLSPDQK VLTITRVLME DDDLYSCVVE NPISQVRSLP VKITVYRRSS

241 LYIILSTGGI FLLVTLVTVC ACWKPSKKSR KKRKLEKQNS LEYMDQNDDR LKSEADTLPR

301 SGEQERKNPM ALYILKDKDS SEPDENPATE PRSTTEPGPP GYSVSPPVPG RSPGLPIRSA

361 RRYPRSPARS PATGRTHTSP PRAPSSPGRS RSSSRSLRTA GVQRIREQDE SGQVEISA
SEQ ID NO:19 (nucleic acid sequence coding for
extracellular domain of INSP052)
   1 ATGAAGAGAG AAAGGGGAGC CCTGTCCAGA GCCTCCAGGG CCCTGCGCCT TGCTCCTTTT

61 GTCTACCTTC TTCTGATCCA GACAGACCCC CTGGAGGGGG TGAACATCAC CAGCCCCGTG

121 CGCCTGATCC ATGGCACCGT GGGGAAGTCG GCTCTGCTTT CTGTGCAGTA CAGCAGTACC

181 AGCAGCGACA GGCCTGTAGT GAAGTGGCAG CTGAAGCGGG ACAAGCCAGT GACCGTGGTG

241 CAGTCCATTG GCACAGAGGT CATCGGCACC CTGCGGCCTG ACTATCGAGA CCGTATCCGA

301 CTCTTTGAAA ATGGCTCCCT GCTTCTCAGC GACCTGCAGC TGGCCGATGA GGGCACCTAT

361 GAGGTCGAGA TCTCCATCAC CGACGACACC TTCACTGGGG AGAAGACCAT CAACCTTACT
```

-continued

```
421 GTAGATGTGC CCATTTCGAG GCCACAGGTG TTGGTGGCTT CAACCACTGT GCTGGAGCTC

481 AGCGAGGCCT TCACCTTGAA CTGCTCACAT GAGAATGGCA CCAAGCCCAG CTACACCTGG

541 CTGAAGGATG GCAAGCCCCT CCTCAATGAC TCGAGAATGC TCCTGTCCCC CGACCAAAAG

601 GTGCTCACCA TCACCCGCGT GCTCATGGAG GATGACGACC TGTACAGCTG CATGGTGGAG

661 AACCCCATCA GCCAGGGCCG CAGCCTGCCT GTCAAGATCA CCGTATACAG AAGAAGCTCC
```

SEQ ID NO:20 (extracellular domain of INSP052)
```
  1 MKRERGALSR ASRALRLAPF VYLLLIQTDP LEGVNITSPV RLIH-
    GTVGKS ALLSVQYSST

61 SSDRPVVKWQ LKRDKPVTVV QSIGTEVIGT LRPDYRDRIR
    LFENGSLLLS DLQLADEGTY

121 EVEISITDDT FTGEKTINLT VDVPISRPQV LVASTTVLEL SEAF-
    TLNCSH ENGTKPSYTW

181 LKDGKPLLND SRMLLSPDQK VLTITRVLME DDDLYSCMVE
    NPISQGRSLP VKITVYRRSS
```

SEQ ID NO:21 (nucleic acid sequence coding for the
extracellular domain of mature INSP052)
G TGAACATCAC CAGCCCCGTG

CGCCTGATCC ATGGCACCGT GGGGAAGTCG GCTCTGCTTT CTGTGCAGTA CAGCAGTACC

AGCAGCGACA GGCCTGTAGT GAAGTGGCAG CTGAAGCGGG ACAAGCCAGT GACCGTGGTG

CAGTCCATTG GCACAGAGGT CATCGGCACC CTGCGGCCTG ACTATCGAGA CCGTATCCGA

CTCTTTGAAA ATGGCTCCCT GCTTCTCAGC GACCTGCAGC TGGCCGATGA GGGCACCTAT

GAGGTCGAGA TCTCCATCAC CGACGACACC TTCACTGGGG AGAAGACCAT CAACCTTACT

GTAGATGTGC CCATTTCGAG GCCACAGGTG TTGGTGGCTT CAACCACTGT GCTGGAGCTC

AGCGAGGCCT TCACCTTGAA CTGCTCACAT GAGAATGGCA CCAAGCCCAG CTACACCTGG

CTGAAGGATG GCAAGCCCCT CCTCAATGAC TCGAGAATGC TCCTGTCCCC CGACCAAAAG

GTGCTCACCA TCACCCGCGT GCTCATGGAG GATGACGACC TGTACAGCTG CATGGTGGAG

AACCCCATCA GCCAGGGCCG CAGCCTGCCT GTCAAGATCA CCGTATACAG AAGAAGCTCC

SEQ ID NO:22 (extracellular domain of mature INSP052)
VNITSPV RLIHGTVGKS ALLSVQYSST

SSDRPVVKWQ LKRDKPVTVV QSIGTEVIGT LRPDYRDRIR LFENGSLLLS DLQLADEGTY

EVEISITDDT FTGEKTINLT VDVPISRPQV LVASTTVLEL SEAFTLNCSH ENGTKPSYTW

LKDGKPLLND SRMLLSPDQK VLTITRVLME DDDLYSCMVE NPISQGRSLP VKITVYRRSS

SEQ Id NO 23: (Nucleotide sequence encoding the
mature INSP052 exon2)
GTGAAC ATCACCAGCC CCGTGCGCCT GATCCATGGC ACCGTGGGGA

AGTCGGCTCT GCTTTCTGTG CAGTACAGCA GTACCAGCAG CGACAGGCCT GTAGTGAAGT

GGCAGCTGAA GCGGGACAAG CCAGTGACCG TGGTGCAGTC CATTGGCACA GAGGTCATCG

GCACCCTGCG GCCTGACTAT CGAGACCGTA TCCGACTCTT TGAAAATGGC TCCCTGCTTC

TCAGCGACCT GCAGCTGGCC GATGAGGGCA CCTATGAGGT CGAGATCTCC ATCACCGACG

ACACCTTCAC TGGGGAGAAG ACCATCAACC TTACTGTAGA TG

SEQ ID NO 24: (Protein Sequence of Mature INSP052 Exon 2)
  1 VNITSP VRLIHGTVGK SALLSVQYSS TSSDRPVVKW QLKRDKPVTV VQSIGTEVIG

61 TLRPDYRDRI RLFENGSLLL SDLQLADEGT YEVEISITDD TFTGEKTINL TVDV

SEQ ID NO :25 (nucleotide sequence encoding the mature
INSP052 polypeptide)
G TGAACATCAC CAGCCCCGTG

CGCCTGATCC ATGGCACCGT GGGGAAGTCG GCTCTGCTTT CTGTGCAGTA CAGCAGTACC

-continued

```
AGCAGCGACA GGCCTGTAGT GAAGTGGCAG CTGAAGCGGG ACAAGCCAGT GACCGTGGTG

CAGTCCATTG GCACAGAGGT CATCGGCACC CTGCGGCCTG ACTATCGAGA CCGTATCCGA

CTCTTTGAAA ATGGCTCCCT GCTTCTCAGC GACCTGCAGC TGGCCGATGA GGGCACCTAT

GAGGTCGAGA TCTCCATCAC CGACGACACC TTCACTGGGG AGAAGACCAT CAACCTTACT

GTAGATGTGC CCATTTCGAG GCCACAGGTG TTGGTGGCTT CAACCACTGT GCTGGAGCTC

AGCGAGGCCT TCACCTTGAA CTGCTCACAT GAGAATGGCA CCAAGCCCAG CTACACCTGG

CTGAAGGATG GCAAGCCCCT CCTCAATGAC TCGAGAATGC TCCTGTCCCC CGACCAAAAG

GTGCTCACCA TCACCCGCGT GCTCATGGAG GATGACGACC TGTACAGCTG CATGGTGGAG

AACCCCATCA GCCAGGGCCG CAGCCTGCCT GTCAAGATCA CCGTATACAG AAGAAGCTCC

CTTTACATCA TCTTGTCTAC AGGAGGCATC TTCCTCCTTG TGACCTTGGT GACAGTCTGT

GCCTGCTGGA AACCCTCCAA AAGGAAACAG AAGAAGCTAG AAAAGCAAAA CTCCCTGGAA

TACATGGATC AGAATGATGA CCGCCTGAAA CCAGAAGCAG ACACCCTCCC TCGAAGTGGT

GAGCAGGAAC GGAAGAACCC CATGGCACTC TATATCCTGA AGGACAAGGA CTCCCCGGAG

ACCGAGGAGA ACCGGCCCCC GGAGCCTCGA AGCGCGACGG AGCCCGGCCC GCCCGGCTAC

TCCGTGTCTC CCGCCGTGCC CGGCCGCTCG CCGGGGCTGC CCATCCGCTC TGCCCGCCGC

TACCCGCGCT CCCCAGCGCG CTCCCCAGCC ACCGGCCGGA CACACTCGTC GCCGCCCAGG

GCCCCGAGCT CGCCCGGCCG CTCGCGCAGC GCCTCGCGCA CACTGCGGAC TGCGGGCGTG

CACATAATCC GCGAGCAAGA CGAGGCCGGC CCGCTGGAGA TCAGCGCCTG A
```

SEQ ID NO:26 (INSP052 mature polypeptide sequence)
VNITSPV RLIHGTVGKS ALLSVQYSST

SSDRPVVKWQ LKRDKPVTVV QSIGTEVIGT LRPDYRDRIR LFENGSLLLS DLQLADEGTY

EVEISITDDT FTGEKTINLT VDVPISRPQV LVASTTVLEL SEAFTLNCSH ENGTKPSYTW

LKDGKPLLND SRMLLSPDQK VLTITRVLME DDDLYSCMVE NPISQGRSLP VKITVYRRSS

LYIILSTGGI FLLVTLVTVC ACWKPSKRKQ KKLEKQNSLE YMDQNDDRLK PEADTLPRSG

EQERKNPMAL YILKDKDSPE TEENPAPEPR SATEPGPPGY SVSPAVPGRS PGLPIRSARR

YPRSPARSPA TGRTHSSPPR APSSPGRSRS ASRTLRTAGV HIIREQDEAG PVEISA

---

The invention claimed is:

1. An isolated polypeptide, which comprises the amino acid sequence as recited in SEQ ID NO:16 or SEQ ID NO:26, wherein the polypeptide functions as an antagonist of cytokine expression and/or secretion of a cytokine selected from the group consisting of TNF-α, IL-4 IL-2, IL-6, IL-5, and IL-10.

2. An isolated ligand which binds specifically to, and which inhibits the activity of a polypeptide of claim 1.

3. An isolated ligand according to claim 2, which is an antibody.

4. A An isolated compound that either increases or decreases the level of expression or activity of a polypeptide according to claim 1, compared to the level of expression or activity of the polypeptide in the absence of the compound.

5. An isolated polypeptide according to claim 1 for use in therapy of an inflammatory or autoimmune liver disease.

6. An isolated compound according to claim 4 wherein said compound increases the level of expression or activity of a polypeptide of claim 1 for use in therapy of an inflammatory or autoimmune liver disease.

7. An isolated polypeptide, which consists of the amino acid sequence as recited in SEQ ID NO:16, SEQ ID NO:26, SEQ ID NO:20; or SEQ ID NO:22, wherein the polypeptide functions as an antagonist of cytokine expression and/or secretion of a cytokine selected from the group consisting of TNF-α, IL-4 and IL-2, IL-6, IL-5, and IL-10.

8. An isolated ligand which binds specifically to, and which inhibits the activity of a polypeptide of claim 7.

9. An isolated ligand according to claim 8, which is an antibody.

10. An isolated compound that either increases or decreases the level of expression or activity of a polypeptide according to claim 7, compared to the level of expression or activity of the polypeptide in the absence of the compound.

11. An isolated polypeptide according to claim 7 for use in therapy of an inflammatory or autoimmune liver disease.

12. An isolated compound according to claim 10 wherein said compound increases the level of expression or activity of a polypeptide of claim 7 for use in therapy of an inflammatory or autoimmune liver disease.

13. An isolated polypeptide according to claim 1 or claim 7 fused to a heterologous polypeptide.

14. An isolated ligand which binds specifically to, and which inhibits the activity of a polypeptide of claim 13.

15. An isolated ligand according to claim 14, which is an antibody.

16. An isolated compound that either increases or decreases the level of expression or activity of a polypeptide according to claim 13, compared to the level of expression or activity of the polypeptide in the absence of the compound.

17. An isolated polypeptide according to claim 13 for use in therapy of an inflammatory or autoimmune liver disease.

18. An isolated compound according to claim 16 wherein said compound increases the level of expression or activity of a polypeptide of claim 13, for use in therapy of an inflammatory or autoimmune liver disease.

* * * * *